(12) United States Patent
Dialer et al.

(10) Patent No.: US 10,059,683 B2
(45) Date of Patent: Aug. 28, 2018

(54) PROCESS FOR THE PRODUCTION OF CANNABIDIOL AND DELTA-9-TETRAHYDROCANNABINOL

(71) Applicant: NORAMCO, INC., Athens, GA (US)

(72) Inventors: Lukas Dialer, Schaffhausen (CH); Denis Petrovic, Schaffhausen (CH); Ulrich Weigl, Schaffhausen (CH)

(73) Assignee: Noramco, Inc., Athens, GA (US)

( * ) Notice: Subject to any disclaimer, the term of this patent is extended or adjusted under 35 U.S.C. 154(b) by 0 days.

(21) Appl. No.: 15/199,528

(22) Filed: Jun. 30, 2016

(65) Prior Publication Data

US 2017/0008868 A1    Jan. 12, 2017

Related U.S. Application Data

(60) Provisional application No. 62/191,097, filed on Jul. 10, 2015.

(51) Int. Cl.
| | |
|---|---|
| *C07D 311/80* | (2006.01) |
| *C07C 37/14* | (2006.01) |
| *C07D 205/04* | (2006.01) |
| *C07C 37/11* | (2006.01) |
| *C07D 311/78* | (2006.01) |
| *C07D 311/04* | (2006.01) |

(52) U.S. Cl.
CPC ............ *C07D 311/78* (2013.01); *C07C 37/11* (2013.01); *C07C 37/14* (2013.01); *C07D 205/04* (2013.01); *C07D 311/04* (2013.01); *C07D 311/80* (2013.01)

(58) Field of Classification Search
CPC ........ C07C 37/11; C07C 37/14; C07D 311/80
See application file for complete search history.

(56) References Cited

U.S. PATENT DOCUMENTS

| 3,562,312 A | 2/1971 | Eschenmoser et al. |
| 5,227,537 A | 7/1993 | Stoss et al. |
| 7,674,922 B2 | 3/2010 | Burdick et al. |

FOREIGN PATENT DOCUMENTS

| WO | WO-01/03690 A1 | 1/2001 |

OTHER PUBLICATIONS

Compton, D.R., et al., "Synthesis and pharmacological evaluation of ether and related analogues of delta 8-, delta 9-, and delta 9,11-tetrahydrocannabinol," J. Med. Chem., 1991, vol. 34, No. 11, pp. 3310-3316.
Crombie, L., et al., "Synthesis of cannabinoid methyl esters and acids," J. Chem. Research, 1977, vol. 114, pp. 1301-1345.

(Continued)

*Primary Examiner* — Valerie Rodriguez-Garcia
(74) *Attorney, Agent, or Firm* — Alston & Bird LLP

(57) ABSTRACT

The present disclosure relates to the preparation of a cannabidiol compound or a derivative thereof. The cannabidiol compound or derivatives thereof can be prepared by an acid-catalyzed reaction of a suitably selected and substituted di-halo-olivetol or derivative thereof with a suitably selected and substituted cyclic alkene to produce a dihalo-cannabidiol compound or derivative thereof. The dihalo-cannabidiol compound or derivative thereof can be produced in high yield, high stereospecificity, or both. It can then be converted under reducing conditions to a cannabidiol compound or derivatives thereof.

21 Claims, 8 Drawing Sheets

(56) References Cited

OTHER PUBLICATIONS

Glaser, R., et al., "2-Methyl- and 4-Methyl-Delta8-Tetrahydrocannabinol: Correlation of Spatial Distinction with Cannabinoid Receptor Binding," Heterocycles Communication, Special Issue, Japanese Institute of Heterocyclic Chemistry, Dec. 31, 1994, vol. 39, No. 2, pp. 867-877.

Sokolovs, I., et al., "Copper-catalyzed intermolecular C-H amination of (hetero)arenes via transient unsymmetrical $\lambda^3$-iodanes," J. Am. Chem. Soc., 2014, vol. 136, pp. 6920-6928.

Srebnik, M., et al., "Halogenation of Phenols and Phenyl Ethers with Potassium Halides in the Presence of 18-Crown-6 on Oxidation with m-Chloroperbenzoic Acid," Journal of the American Chemical Society, Perkin Transactions I, 1987, pp. 1423-1427.

PROCESS FOR THE PRODUCTION OF CANNABIDIOL AND DELTA-9-TETRAHYDROCANNABINOL

CROSS-REFERENCE TO RELATED APPLICATIONS

This application claims the benefit of and priority to U.S. Provisional Patent Application No. 62/191,097, filed on Jul. 10, 2015, the entire content of which is incorporated herein by reference.

FIELD OF THE INVENTION

The present disclosure relates to the preparation of a cannabidiol compound or a derivative thereof. The cannabidiol compound or derivative thereof can be prepared by an acid-catalyzed reaction of a suitably selected and substituted di-halo-olivetol or derivative thereof with a suitably selected and substituted cyclic alkene to produce a dihalo-cannabidiol compound or derivative thereof. The dihalo-cannabidiol compound or derivative thereof can be produced in high yield, high stereospecificity, or both. It can then be converted under reducing conditions to a cannabidiol compound or derivatives thereof.

BACKGROUND OF THE INVENTION

More than 100 phytocannabinoids have been isolated to date. See Pertwee, et al. "Hand book of *Cannabis*," Oxford University Press, First Edition 2014, ISBN 978-0-19-966268-5. Phytocannabinoids are cannabinoids that originate from nature and can be found in the *cannabis* plant. These compounds have been investigated based, in part, on their availability from a natural source. The term "cannabinoids" generally refers to not only the chemical substances isolated from *C. sativa* L exhibiting the typical C21 terpenophilic skeleton, but also to their derivatives and transformation products.

In addition to the historical and anecdotal medicinal use of cannabinoids, the FDA has approved cannabinoid based products, such as Marinol™ and a number of other regulatory agencies have approved Sativex™. Many other cannabinoids are being investigated by the mainstream pharmaceutical industry for various indications. Examples of cannabinoids either approved for clinical use or in clinical trials include Epidiolex™ (e.g., cannabidiol) for Dravet Syndrome and Lennox-Gastaut Syndrome; cannabidivarin for epilepsy; and tetrahydrocannabidivarin for diabetes.

Many different routes to produce cannabinoids and related compounds have been reported. One route involves variations on the Lewis-acid catalyzed Friedel Crafts alkylation of olivetol with menthadienol. For example, U.S. Pat. No. 5,227,537 describes a reaction of equimolar quantities of olivetol and menthadienol in the presence of p-toluenesulfonic acid catalyst which resulted in a 44% yield of cannabidiol after purification by column chromatography. U.S. Pat. No. 7,674,922 describes a similar reaction using a Lewis acid catalyst instead of p-toluenesulfonic acid which results in the formation of significant amounts of the unwanted cannabidiol isomer along with cannabidiol. The reaction route described in the '922 patent resulted in a 47% yield of the desired cannabidiol, a 17.9% yield of the abn cannabidiol and 23% of unreacted olivetol.

In addition, U.S. Pat. No. 3,562,312 describes improved selectivity for the formation of cannabidiol by reacting 6-carbethoxyolivetol with a slight excess of menthadienol in methylene chloride in the presence of dimethylformamide, dineopentylacetal as catalyst. This route resulted in a 42% yield of cannabidiol-carboxylic acid ethyl ester after purification by chromatography.

Another route for the preparation of cannabidiols involves the use of carboxylic acid esters as protecting/directing groups on olivetol analogues. See, e.g., Crombie, L. et al., in *J. Chem. Research (S)* 114, (M), pp 1301-1345 (1977). In a first step, alkylresorcyl esters (e.g., 6-alkyl-2,4-di-hydroxy-benzoic esters) are condensed with unsaturated hydrocarbons, alcohols, ketones, or derivatives thereof such as enol esters, enol ethers and ketals, in high yields to give the corresponding 3-substituted 6-alkyl-2,4-dihydroxybenzoic esters. These routes of preparation have been referred to as acid-catalyzed terpenylation. In a second step, the intermediates with an ester function obtained in the first step are subjected to a decarboxylating hydrolysis, which forms the ester-free cannabinoids.

For example, improvements in selectivity have been achieved by protecting the 4 position of the olivetol related compounds with a carboxylic acid ester. The '922 patent describes the preparation of ethyl cannabidiolate in 82% yield and 93.3% (AUC) purity. After NaOH hydrolysis, however, the route resulted in a 57.5% yield and 99.8% purity (AUC). The '922 patent also describes the need to purify the cannabidiols formed, e.g., Δ-9-tetrahydrocannabinol, by esterification of the free hydroxyl followed by purification of the cannabidiol ester, e.g., Δ-9-tetrahydrocannabinol ester. Purification was performed by crystallization followed by hydrolysis of the ester to the Δ-9-tetrahydrocannabinol. Such steps were required to achieve a purity necessary for pharmaceutical use.

The prior art demonstrates the difficulties of manufacturing cannabidiol compounds or derivatives thereof, e.g., Δ-9-tetrahydrocannabinol, in high yield, high stereospecificity, or both. The causes of these difficulties can include the non-crystalline nature of the materials which renders them difficult or impossible to separate and purify without chromatography. Also, the aromatic portion of the cannabidiol molecule is sensitive to oxidation. And, in one specific example, the thermodynamic stability of the Δ-9-unsaturation relative to Δ-8-unsaturation favors the formation of Δ-8 derivatives.

The present disclosure relates to the preparation of a cannabidiol compound or a derivative thereof using a simple synthesis route to produce a cannabidiol compound or derivative thereof in high yield, high stereospecificity, or both.

SUMMARY OF THE INVENTION

The present disclosure relates to the preparation of a cannabidiol compound or a derivative thereof. The cannabidiol compound or derivative thereof can be prepared by an acid-catalyzed reaction of a suitably selected and substituted di-halo-olivetol or derivative thereof with a suitably selected and substituted cyclic alkene (e.g., a cyclic alkene containing a 1-methyl-1-ethenyl substituent) to produce a dihalo-cannabidiol compound or derivative thereof. The dihalo-cannabidiol compound or derivative thereof can be produced in high yield, high stereospecificity, or both. It can then be converted under reducing conditions to a cannabidiol compound or derivative thereof.

The present disclosure also relates to the preparation of a Δ-9-tetrahydrocannabinol compound or derivative thereof. The Δ-9-tetrahydrocannabinol compound or derivative thereof can be prepared by an acid-catalyzed reaction of a suitably selected and substituted di-halo-olivetol or derivative thereof with a suitably selected and substituted cyclic alkene to produce a dihalo-cannabidiol compound or derivative thereof. The dihalo-cannabidiol compound or derivative thereof can be produced in high yield, high stereospecificity, or both. It can then be reacted with a Lewis acid catalyst to produce a dihalo-Δ-9-tetrahydrocannabinol compound or derivative thereof. The dihalo-Δ-9-tetrahydrocannabinol compound or derivative thereof can then be converted under reducing conditions to a Δ-9-tetrahydrocannabinol compound or derivative thereof. Alternatively, the reduction and cyclization steps can be performed in reverse order.

In one embodiment, the present disclosure relates to a process for the preparation of a compound of formula (I)

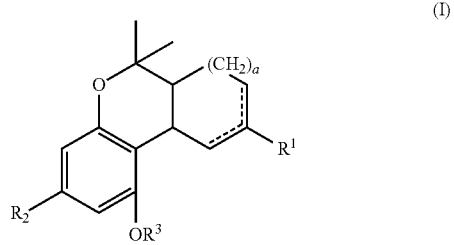

(I)

wherein a is an integer from 0 to 3;

$R^1$ and $R^2$ are each independently selected from the group consisting of H, OH, protected hydroxyl, alkyl, alkenyl, alkynyl, acyl, aryl, heteroaryl, cycloalkyl or heterocycle; wherein the alkyl, alkenyl, alkynyl or acyl is optionally substituted with one or more substituents independently selected from the group consisting of halogen, —OH, alkyl, —O-alkyl, $NR^AR^B$, —S-alkyl, —SO-alkyl, —SO$_2$-alkyl, alkenyl, alkynyl, aryl, heteroaryl, cycloalkyl or heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —SO$_2$-alkyl; wherein $R^C$ and $R^D$ are each independently selected from hydrogen and $C_{1-4}$ alkyl;

$R^3$ is selected from the group consisting of H, alkyl, acyl, —SO$_2$-alkyl, —SO$_2$-aryl and —SO$_2$-heteroaryl; wherein the alkyl is optionally substituted with one or more substituents independently selected from the group consisting of halogen, —OH, alkyl, —O-alkyl, $NR^ER^F$, —S-alkyl, —SO-alkyl, —SO$_2$-alkyl, aryl and heteroaryl; and wherein $R^E$ and $R^F$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, $NR^GR^H$, —S-alkyl, —SO-alkyl and —SO$_2$-alkyl; wherein $R^G$ and $R^H$ are each independently selected from hydrogen and $C_{1-4}$ alkyl;

each ------- represents a single or double bond; provided that both ------- groups are not double bonds, and wherein denoted, dash marks indicate the points of attachment, or a pharmaceutically acceptable salt or ester thereof;

the process including reacting a compound of formula (II), wherein each X is independently selected from the group consisting of Br, F, I and Cl, with a compound of formula (III) wherein $R^0$ is H or OH, in the presence of a protic or first Lewis acid catalyst to form a compound of formula (IV);

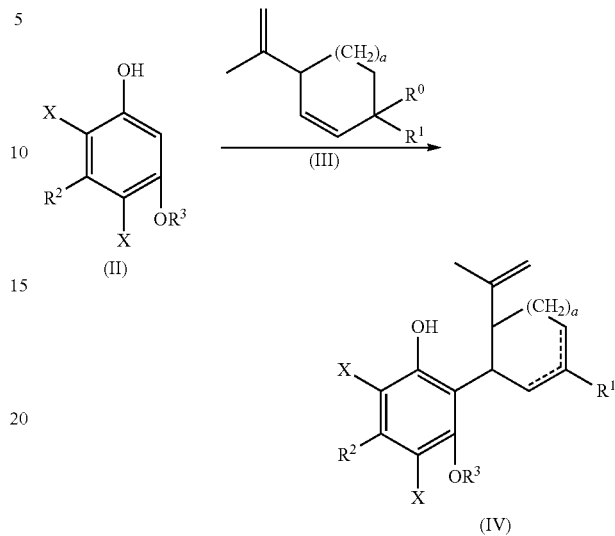

cyclizing the compound of formula (IV) by reacting the compound of formula (IV) with a second Lewis acid catalyst to form a compound of formula (V); and

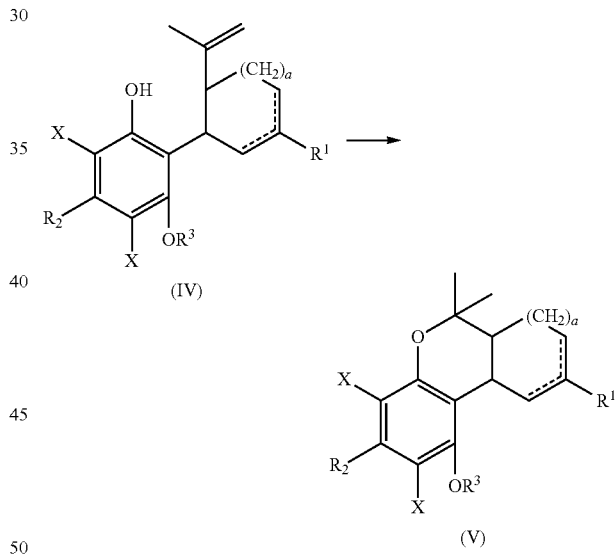

reacting the compound of formula (V) with a reducing agent to form the compound of formula (I)

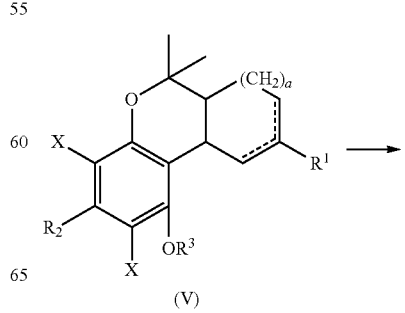

-continued

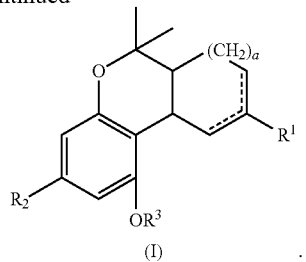

(I)

In another embodiment, the present disclosure relates to a process for the preparation of a compound of formula (I)

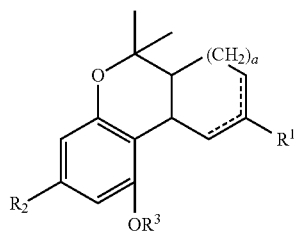

(I)

wherein a is an integer from 0 to 3;

$R^1$ and $R^2$ are each independently selected from the group consisting of H, OH, protected hydroxyl, alkyl, alkenyl, alkynyl, acyl, aryl, heteroaryl, cycloalkyl or heterocycle;

wherein the alkyl, alkenyl, alkynyl or acyl is optionally substituted with one or more substituents independently selected from the group consisting of halogen, —OH, alkyl, —O-alkyl, $NR^A R^B$, —S-alkyl, —SO-alkyl, —$SO_2$-alkyl, alkenyl, alkynyl, aryl, heteroaryl, cycloalkyl or heterocycle; wherein $R^A$ and $R^B$ are each independently selected from hydrogen and $C_{1-4}$ alkyl;

wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^C R^D$, —S-alkyl, —SO-alkyl and —$SO_2$-alkyl; wherein $R^C$ and $R^D$ are each independently selected from hydrogen and $C_{1-4}$ alkyl;

$R^3$ is selected from the group consisting of H, alkyl, acyl, —$SO_2$-alkyl, —$SO_2$-aryl and —$SO_2$-heteroaryl; wherein the alkyl is optionally substituted with one or more substituents independently selected from the group consisting of halogen, —OH, alkyl, —O-alkyl, $NR^E R^F$, —S-alkyl, —SO-alkyl, —$SO_2$-alkyl, aryl and heteroaryl; and wherein $R^E$ and $R^F$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, $NR^G R^H$, —S-alkyl, —SO-alkyl and —$SO_2$-alkyl; wherein $R^G$ and $R^H$ are each independently selected from hydrogen and $C_{1-4}$ alkyl;

each ------- represents a single or double bond; provided that both ------- groups are not double bonds, and wherein denoted, dash marks indicate the points of attachment;

or a pharmaceutically acceptable salt or ester thereof;

the process including reacting a compound of formula (II), wherein each X is independently selected from the group consisting of Br, F, I and Cl, with a compound of formula (III) wherein $R^O$ is H or OH in the presence of a protic or first Lewis acid catalyst to form a compound of formula (IV);

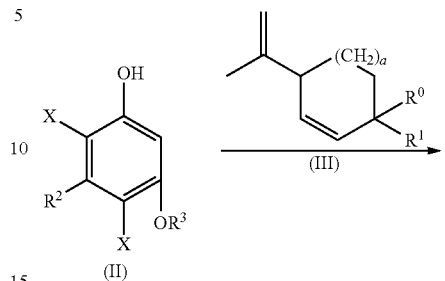

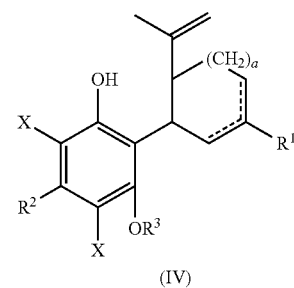

(IV)

reacting the compound of formula (IV) with a reducing agent to form a compound of formula (VI); and

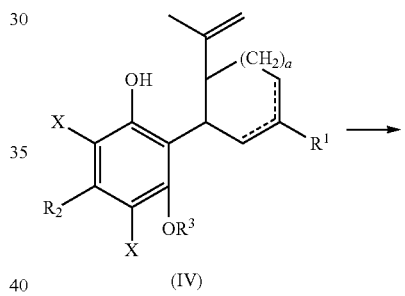

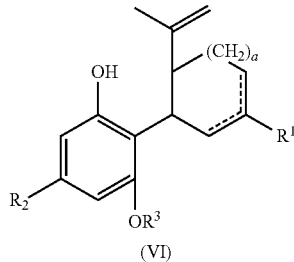

(VI)

cyclizing the compound of formula (VI) by reacting the compound of formula (VI) with a second Lewis acid catalyst to form the compound of formula (I).

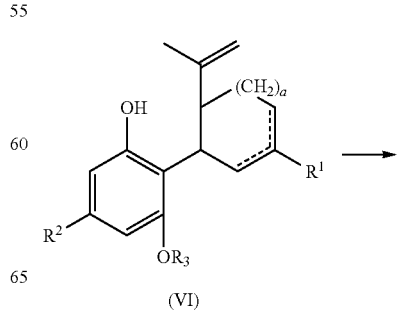

(VI)

-continued

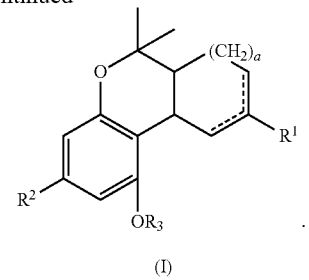

(I)

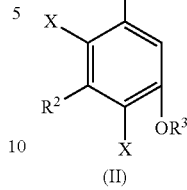

(II)

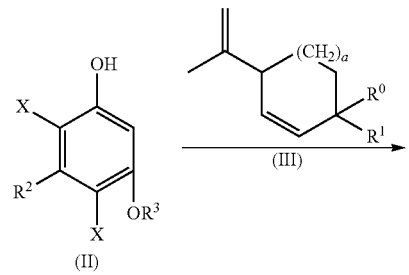

(III)

In another embodiment, the present disclosure relates to a process for the preparation of a compound of formula (VI)

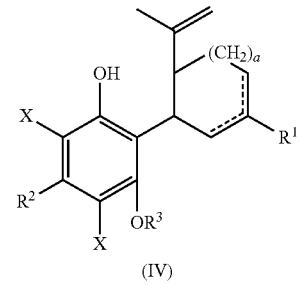

(IV)

reacting the compound of formula (IV) with a reducing agent to form the compound of formula (VI)

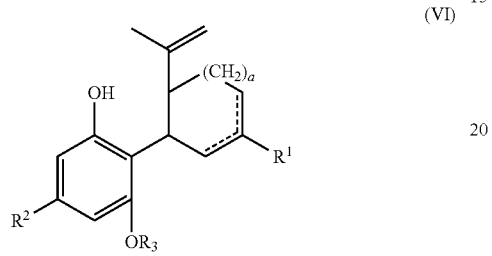

(VI)

wherein a is an integer from 0 to 3;

R$^1$ and R$^2$ are each independently selected from the group consisting of H, OH, protected hydroxyl, alkyl, alkenyl, alkynyl, acyl, aryl, heteroaryl, cycloalkyl or heterocycle;

wherein the alkyl, alkenyl, alkynyl or acyl is optionally substituted with one or more substituents independently selected from the group consisting of halogen, —OH, alkyl, —O-alkyl, NR$^A$R$^B$, —S-alkyl, —SO-alkyl, —SO$_2$-alkyl, alkenyl, alkynyl, aryl, heteroaryl, cycloalkyl or heterocycle; wherein R$^A$ and R$^B$ are each independently selected from hydrogen and C$_{1-4}$ alkyl;

wherein the aryl or heteroaryl, whether alone or as part of a substituent group, is optionally substituted with one or more substituents independently selected from the group consisting of halogen, —OH, alkyl, —O-alkyl, —COOH, —C(O)—C$_{1-4}$ alkyl, —C(O)O—C$_{1-4}$ alkyl, NR$^C$R$^D$, —S-alkyl, —SO-alkyl and —SO$_2$-alkyl; wherein R$^C$ and R$^D$ are each independently selected from hydrogen and C$_{1-4}$ alkyl;

R$^3$ is selected from the group consisting of H, alkyl, acyl, —SO$_2$-alkyl, —SO$_2$-aryl and —SO$_2$-heteroaryl; wherein the alkyl is optionally substituted with one or more substituents independently selected from the group consisting of halogen, —OH, alkyl, —O-alkyl, NR$^E$R$^F$, —S-alkyl, —SO-alkyl, —SO$_2$-alkyl, aryl and heteroaryl; and wherein R$^E$ and R$^F$ are each independently selected from hydrogen and C$_{1-4}$ alkyl; wherein the aryl or heteroaryl, whether alone or as part of a substituent group, is optionally substituted with one or more substituents independently selected from the group consisting of halogen, —OH, alkyl, —O-alkyl, NR$^G$R$^H$, —S-alkyl, —SO-alkyl and —SO$_2$-alkyl; wherein R$^G$ and R$^H$ are each independently selected from hydrogen and C$_{1-4}$ alkyl;

each ====== represents a single or double bond; provided that both ====== groups are not double bonds, and wherein denoted, dash marks indicate the points of attachment;

or a pharmaceutically acceptable salt or ester thereof;

the process including reacting a compound of formula (II), wherein each X is independently selected from the group consisting of Br, F, I and Cl, with a compound of formula (III) wherein R$^0$ is H or OH, in the presence of a protic or first Lewis acid catalyst to form a compound of formula (IV); and

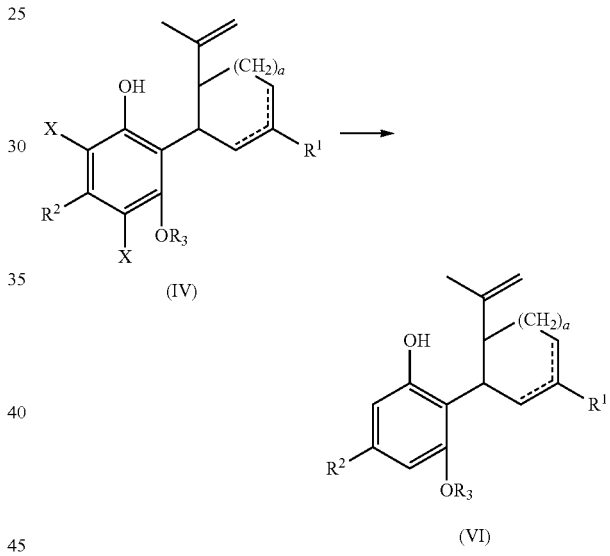

In another embodiment, the present disclosure relates to a process for the preparation of a compound of formula (XI)

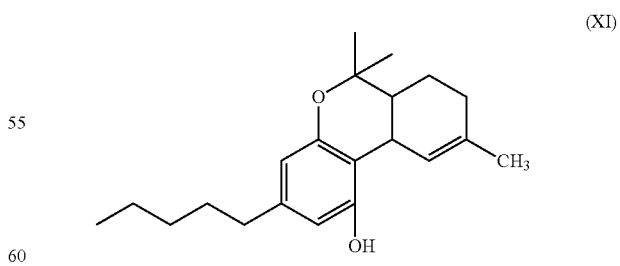

(XI)

or a pharmaceutically acceptable salt or ester thereof;

the process including reacting a compound of formula (XII), wherein each X is independently selected from Br, F, I or Cl, with a compound of formula (XIII) in the presence of a protic or first Lewis acid catalyst to form a compound of formula (XIV);

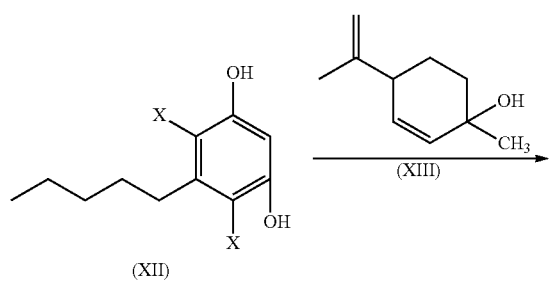

(XII)  (XIII)

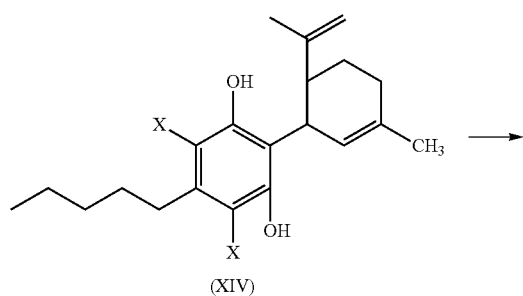

(XIV)

cyclizing the compound of formula (XIV) by reacting the compound of formula (XIV) with a second Lewis acid catalyst to form a compound of formula (XV); and

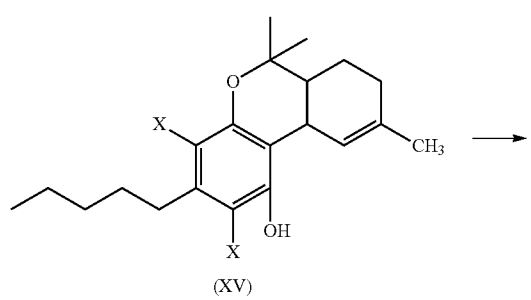

(XV)

reacting the compound of formula (XV) with a reducing agent to form the compound of formula (XI)

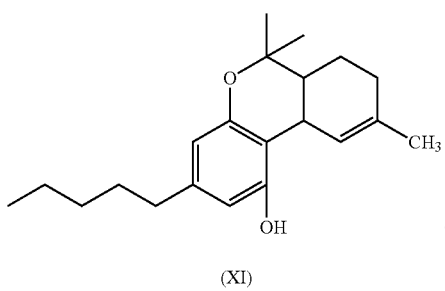

(XI)

In another embodiment, the present disclosure relates to a process for the preparation of a compound of formula (XI)

(XI)

or a pharmaceutically acceptable salt or ester thereof;

the process including reacting a compound of formula (XII), wherein each X is independently selected from Br, F, I or Cl, with a compound of formula (XIII) in the presence of a protic or first Lewis acid catalyst to for a compound of formula (XIV)

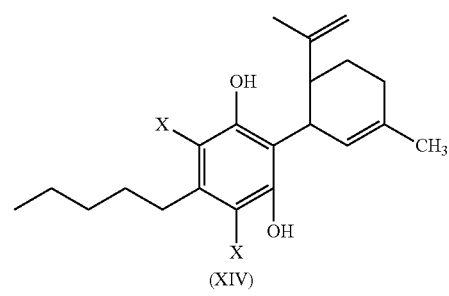

(XII)  (XIII)

(XIV)

reacting the compound of formula (XIV) with a reducing agent to for a compound of formula (XVI); and

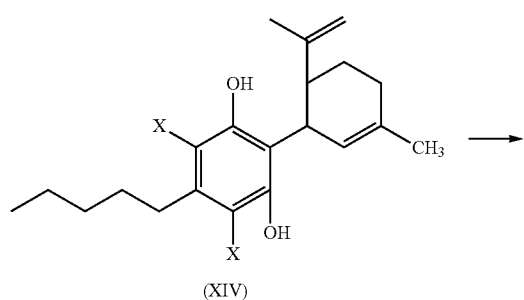

(XIV)

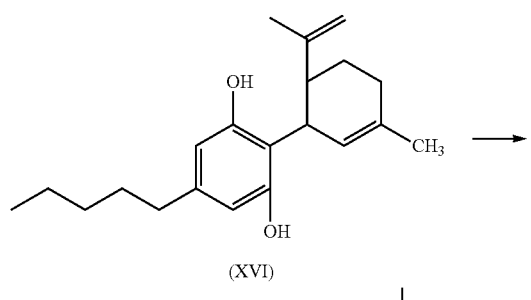

(XVI)

cyclizing the compound of formula (XVI) by reacting the compound of formula (XVI) with a second Lewis acid catalyst to form the compound of formula (XI)

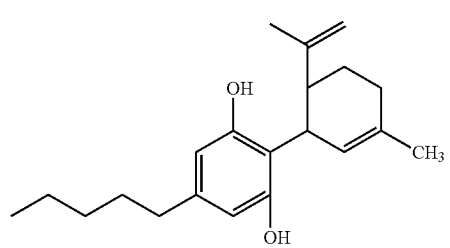

(XI)

In another embodiment, the present disclosure relates to a process for the preparation of a compound of formula (XVI)

(XVI)

or a pharmaceutically acceptable salt or ester thereof;

the process including reacting a compound of formula (XII), wherein each X is independently selected from Br, F, I or Cl, with a compound of formula (XIII) in the presence of a protic or first Lewis acid catalyst to form a compound of formula (XIV); and

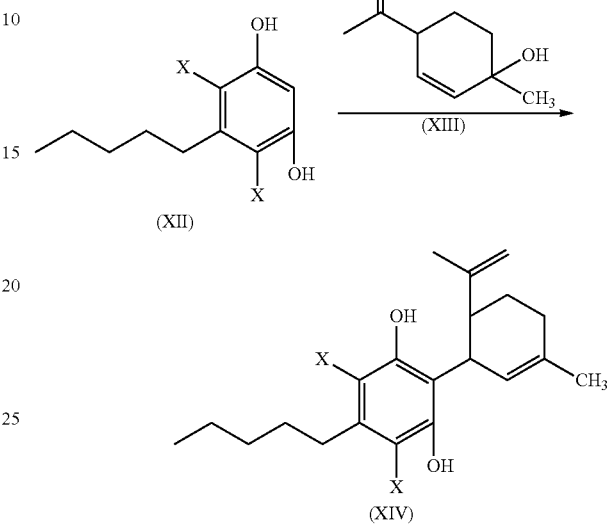

(XII)    (XIII)

(XIV)

reacting the compound of formula (XIV) with a reducing agent to form the compound of formula (XVI)

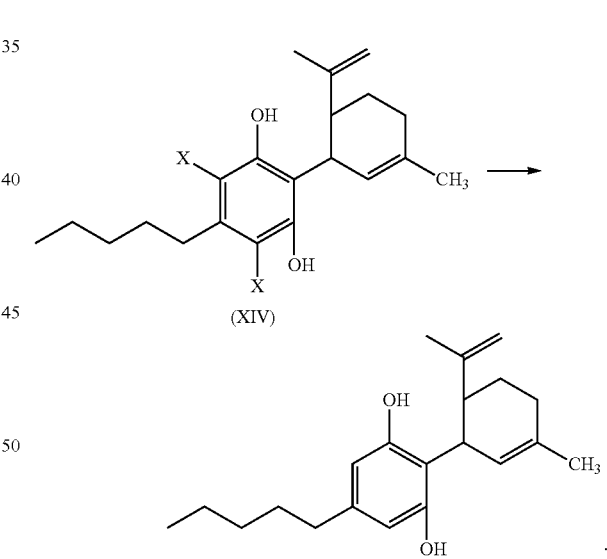

(XIV)

(XVI)

In the processes described above, the formed compounds can be a cannabidiol or related compound. In particular, the compound of formula (I) can be ethyl cannabidiolate, delta-9-tetrahydrocannabidiol or delta-8-tetrahydrocannabidiol. In particular, the compound of formula (IV) can be cannabidiol, cannabidivarin or 1-(3-(((1'R,2'R)-2,6-dihydroxy-5'-methyl-2'-(prop-1-en-2-yl)-1',2',3',4'-tetrahydro-[1,1'-biphenyl]-4-yl)methyl)azetidin-1-yl)ethan-1-one (depicted below)

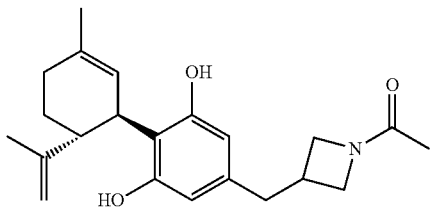

(XX)

The processes of the present disclosure provide a number of advantages over current methods. As described in the prior art, the Lewis acid catalyzed condensation of olivetol or olivetolate esters with menthadienol to prepare cannabidiol or cannabidiolate esters suffers from poor selectivity resulting low yields and mixtures of isomers requiring tedious purification procedures. For example, the use of boron trifluoride etherate results in uncontrolled conversion of cannabidiol and the cyclization of Δ-9-tetrahydrocannabinol to Δ-8-tetrahydrocannabinol. In the present disclosure, one or both of the 4 and 6 positions of olivetol or derivatives thereof can be blocked with a halogen selected from the group consisting of Br, F, I and Cl. In particular, both positions can be blocked with a halogen selected from the group consisting of Br, F, I and Cl. In one embodiment, both positions can be blocked with a Br. In another embodiment, both positions can be blocked with a F. In yet another embodiment, both positions can be blocked with a Cl. The position can be blocked to control the conversion and prevent the formation of unwanted cannabidiol isomers, such as the abn cannabidiol. In addition, the process can be designed, such as by using excess equivalents of an alkene relative to a halogen substituted olivetol or derivatives thereof to form the corresponding halogen substituted cannabidiol or derivative thereof in a high yield, high selectivity or both. In some embodiments, deficient amount can be used for economical purposes. The halogen substituted cannabidiol can also remain stable and not undergo uncontrolled conversion to one or more cyclized products. The halogen substituted cannabidiol or derivative thereof can also be easily converted to a cannabidiol or derivative thereof by reacting with a suitably selected reducing agent, under mild conditions, to yield the desired product in high yield, high purity or both.

The processes of the present disclosure can achieve high yield, high purity or both without the need to use organoaluminum Lewis acid catalysts. The processes of the present disclosure can use a wide selection of catalysts including boron trifluoride etherate and aluminum trichloride. The processes of the present disclosure can achieve high yield, high purity cannabinoid or derivative, or both without the need for purification by formation of a polar ester group, crystallization of the resulting ester, and/or hydrolysis to purified cannabidiol or related derivative, or related purification. The processes of the present disclosure do not require additional derivatization of the isolated cannabidiol or related derivative, e.g., Δ-9-tetrahydrocannabinol, prior to pharmaceutical use.

BRIEF DESCRIPTION OF THE DRAWINGS

The foregoing and other advantages provided by the present disclosure will be more fully understood from the following description of exemplary embodiments when read together with the accompanying drawings, in which.

DETAILED DESCRIPTION OF THE INVENTION

Figure 1:
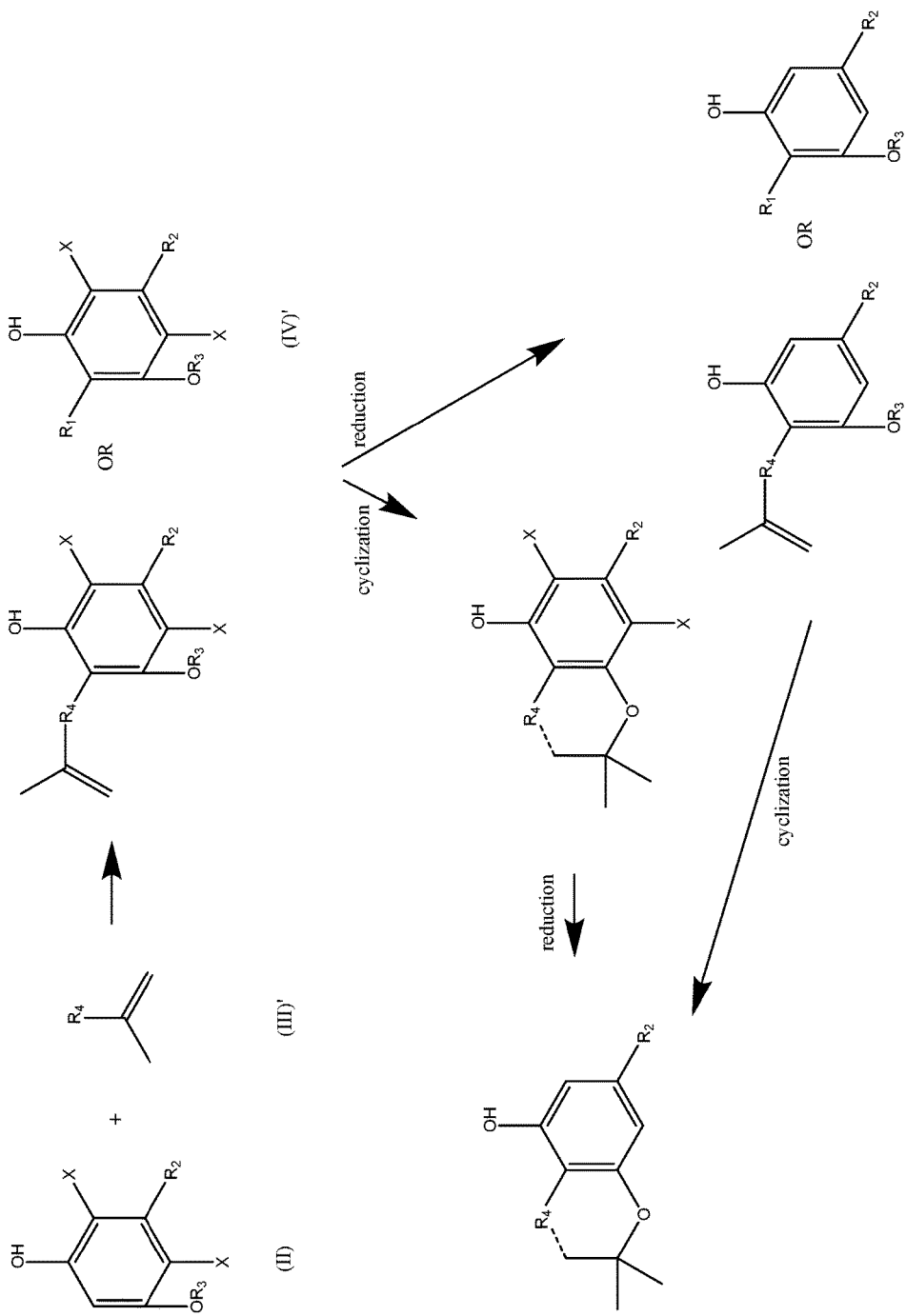
FIG. 1 shows exemplary synthetic pathways of the present disclosure.
Figure 2:
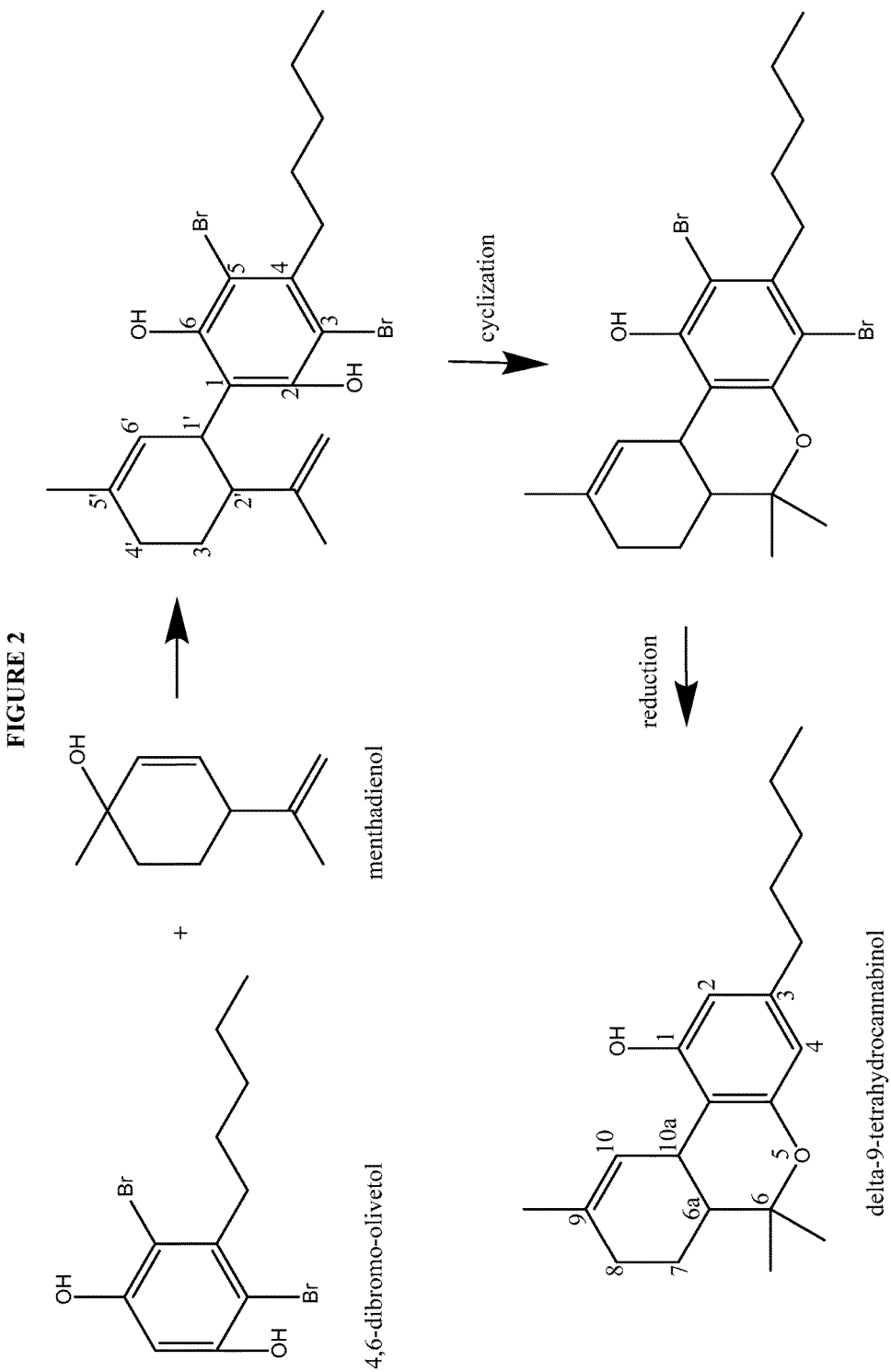
FIG. 2 shows an exemplary synthesis of delta-9-tetrahydrocannabidiol.
Figure 3:
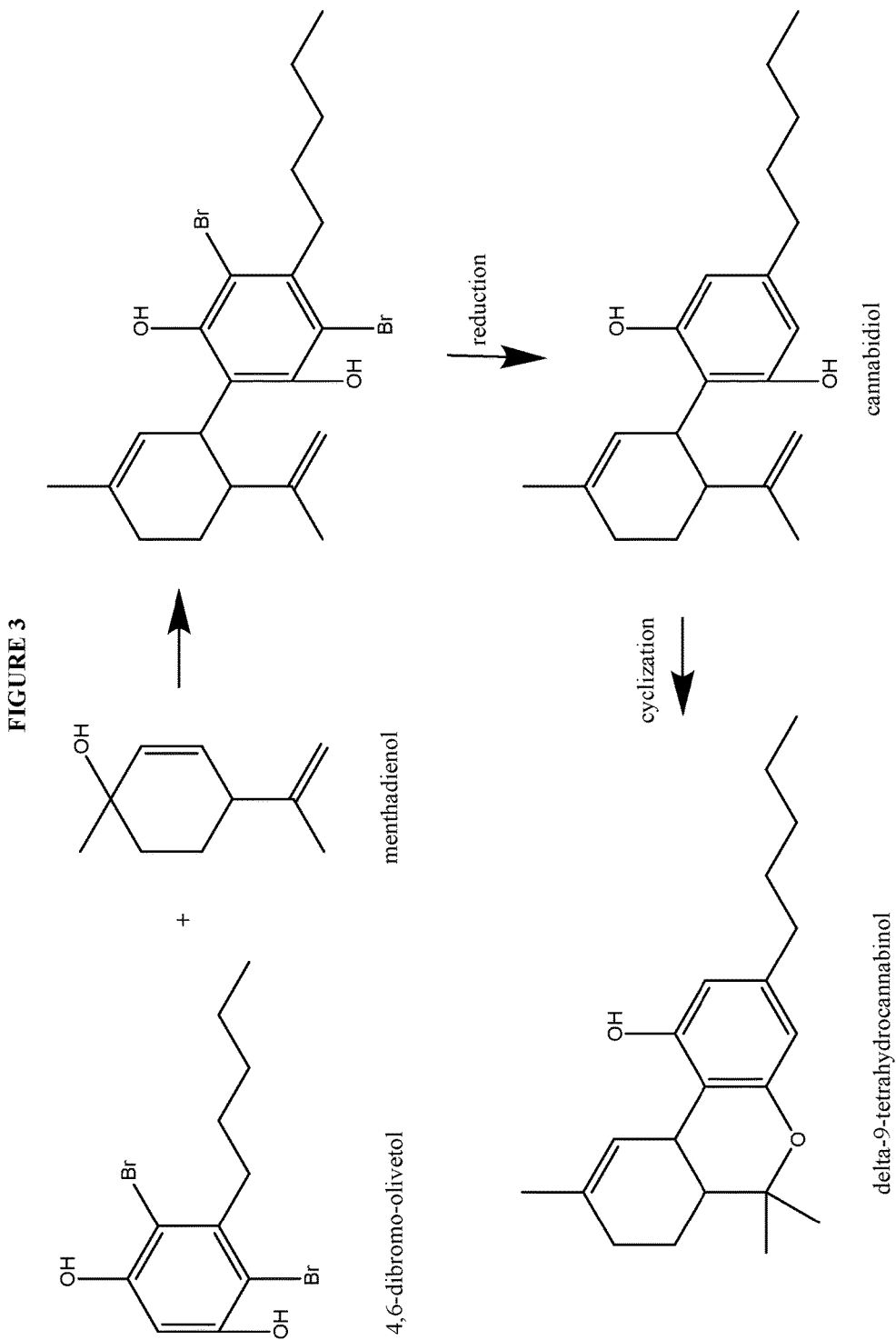
FIG. 3 shows another exemplary synthesis of delta-9-tetrahydrocannabidiol.

The present disclosure relates to processes for the preparation of a cannabidiol compound or derivatives thereof. For example, the present disclosure relates to processes for the preparation of cannabidiol, Δ-9-tetrahydrocannabinol, cannabidiolic acid, Δ-9-tetrahydrocannabinolic acid, intermediate compounds thereof and derivative compounds thereof.

In an embodiment, the present disclosure is directed to process(es) for the preparation of a compound of formula (I) or pharmaceutically acceptable salt or ester thereof.

In one embodiment, the present disclosure relates to a process for the preparation of a compound of formula (I)

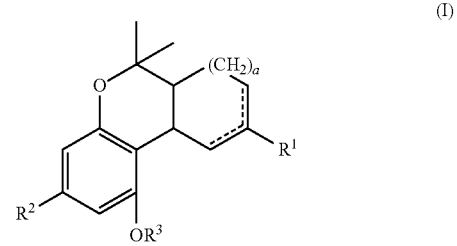

(I)

wherein a is an integer from 0 to 3 (e.g., forming a 5, 6, 7 or 8 membered ring);

$R^1$ and $R^2$ are each independently selected from the group consisting of H, OH, protected hydroxyl, alkyl, alkenyl, alkynyl, acyl, aryl, heteroaryl, cycloalkyl or heterocycle;

wherein the alkyl, alkenyl, alkynyl or acyl is optionally substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl or heterocycle;

wherein $R^A$ and $R^B$ are each independently selected from hydrogen and $C_{1-4}$ alkyl;

wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl;

$R^3$ is selected from the group consisting of H, alkyl, acyl, —$SO_2$-alkyl, —$SO_2$-aryl and —$SO_2$-heteroaryl; wherein the alkyl is optionally substituted with one or more substituents independently selected from the group consisting of halogen, —OH, alkyl, —O-alkyl, $NR^E R^F$, —S-alkyl, —SO-alkyl, —$SO_2$-alkyl, aryl and heteroaryl; and wherein $R^E$ and $R^F$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, $NR^G R^H$, —S-alkyl, —SO-alkyl and —$SO_2$-alkyl; wherein $R^G$ and $R^H$ are each independently selected from hydrogen and $C_{1-4}$ alkyl;

each ══════ represents a single or double bond; provided that both ══════ groups are not double bonds, and wherein denoted, dash marks indicate the points of attachment;

or a pharmaceutically acceptable salt or ester thereof;

the process including reacting a compound of formula (II), wherein each X is independently selected from the group consisting of Br, F, I and Cl, with a compound of formula (III) wherein $R^0$ is H or OH (or as otherwise defined herein), in the presence of a protic or first Lewis acid catalyst to form a compound of formula (IV);

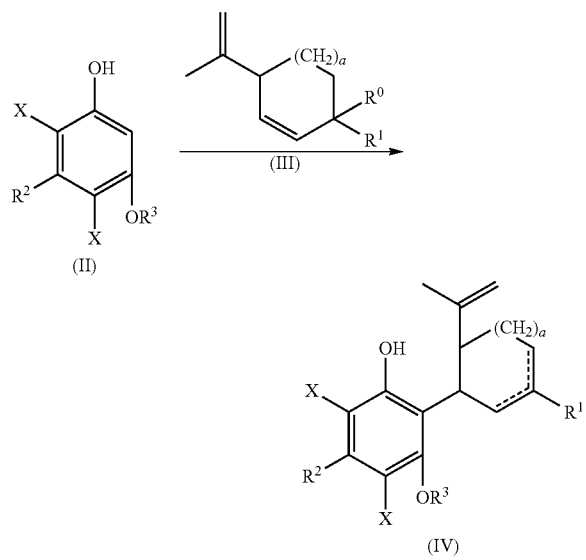

cyclizing the compound of formula (IV) by reacting the compound of formula (IV) with a second Lewis acid catalyst to form a compound of formula (V); and

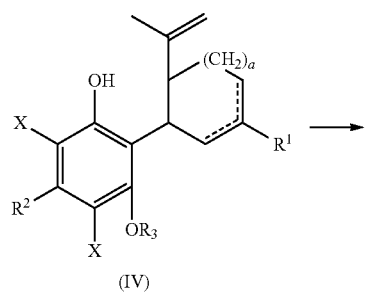

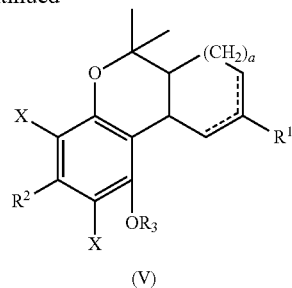

reacting the compound of formula (V) with a reducing agent to form the compound of formula (I)

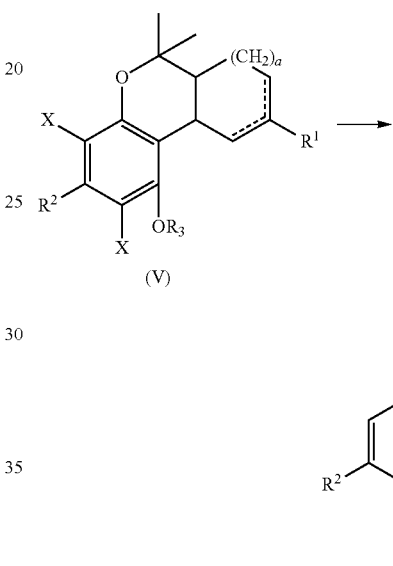

In some embodiments, $R^0$ can be selected from the group consisting of H, OH, protected hydroxyl, alkyl, alkenyl, alkynyl, acyl, aryl, heteroaryl, cycloalkyl or heterocycle;

wherein the alkyl, alkenyl, alkynyl or acyl is optionally substituted with one or more substituents independently selected from the group consisting of halogen, —OH, alkyl, —O-alkyl, $NR^I R^J$, —S-alkyl, —SO-alkyl, —$SO_2$-alkyl, alkenyl, alkynyl, aryl, heteroaryl, cycloalkyl or heterocycle; wherein $R^I$ and $R^J$ are each independently selected from hydrogen and $C_{1-4}$ alkyl;

wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^L R^M$, —S-alkyl, —SO-alkyl and —$SO_2$-alkyl; wherein $R^L$ and $R^M$ are each independently selected from hydrogen and $C_{1-4}$ alkyl.

In other embodiments, $R^0$ and $R^1$ are each independently selected from the group consisting of hydrogen and alkyl; wherein the alkyl is optionally substituted with one or more substituents independently selected from the group consisting of alkyl, alkenyl, alkynyl and aryl.

In some embodiments, $R^2$ is selected from the group consisting of H, OH, protected hydroxyl, alkyl, alkenyl, alkynyl, acyl, aryl, heteroaryl, cycloalkyl or heterocycle;

wherein the alkyl, alkenyl, alkynyl or acyl is optionally substituted with one or more substituents independently selected from the group consisting of halogen, —OH, alkyl, —O-alkyl, $NR^A R^B$, —S-alkyl, —SO-alkyl, —$SO_2$-alkyl, alkenyl, alkynyl, aryl, heteroaryl, cycloalkyl or heterocycle; wherein $R^A$ and $R^B$ are each independently selected from hydrogen and $C_{1-4}$ alkyl;

wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^C R^D$, —S-alkyl, —SO-alkyl and —$SO_2$-alkyl; wherein $R^C$ and $R^D$ are each independently selected from hydrogen and $C_{1-4}$ alkyl.

In one embodiment, the R groups, e.g., $R^A$ and $R^B$, $R^C$ and $R^D$, etc., and the nitrogen atom to which they are bound can optionally form a 4 to 6 membered, saturated, partially unsaturated or aromatic ring structure; wherein the 4 to 6 membered, saturated, partially unsaturated or aromatic ring structure is optionally substituted with one, two or more substituents independently selected from the group consisting of —COOH, C(O)—$C_{1-4}$ alkyl and —C(O)O—$C_{1-4}$ alkyl.

FIG. 1 shows exemplary synthetic pathways of the present disclosure. The substituents, e.g., R groups, are defined herein. As shown in FIG. 1, the $R_4$ group can be selected from the group consisting of a substituted or unsubstituted alkyl, substituted or unsubstituted alkenyl, substituted or unsubstituted alkynyl, substituted or unsubstituted acyl, substituted or unsubstituted aryl, substituted or unsubstituted cycloalkyl, substituted or unsubstituted cycloalkenyl, substituted or unsubstituted heterocycle or substituted or unsubstituted heteroaryl.

As used herein the term "alkyl", whether alone or as part of a substituent group, refers to a saturated $C_1$-$C_n$ carbon chain, wherein the carbon chain may be straight or branched; wherein n can be 2, 3, 4, 5, 6, 7, 8, 9 or 10. Suitable examples include, but are not limited to methyl, ethyl, propyl, isopropyl, butyl, isobutyl, sec-butyl, t-butyl, n-pentyl and n-hexyl.

As used herein the term "alkenyl", whether alone or as part of a substituent group, refers to a $C_2$-$C_n$ carbon chain, wherein the carbon chain may be straight or branched, wherein the carbon chain contains at least one carbon-carbon double bond, and wherein n can be 3, 4, 5, 6, 7, 8, 9 or 10.

As used herein the term "alkynyl", whether alone or as part of a substitutent group, refers to a $C_2$-$C_n$, wherein the carbon chain may be straight or branched, wherein the carbon chain contains at least one carbon-carbon triple bond, and wherein n can be 3, 4, 5, 6, 7, 8, 9 or 10.

As used herein the term "aryl", whether alone or as part of a substituent group, refers to an unsubstituted carbocylic aromatic ring comprising between 6 to 14 carbon atoms. Suitable examples include, but are not limited to, phenyl and naphthyl.

As used herein the term "protected hydroxyl" refers to a hydroxyl group substituted with a suitably selected oxygen protecting group. More particularly, a "protected hydroxyl" refers to a substituent group of the formula —$OPG^1$ wherein $PG^1$ is a suitably selected oxygen protecting group. During any of the processes for preparation of the compounds of the present disclosure it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

As used herein the term "oxygen protecting group" refers to a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM and THP. Other suitable oxygen protecting groups may be found in texts such as T. W. Greene & P. G. M. Wuts, Protective Groups in Organic Synthesis, John Wiley & Sons, 1991.

As used herein the term "nitrogen protecting group" refers to a group which may be attached to a nitrogen atom to protect said nitrogen atom from participating in a reaction and which may be readily removed following the reaction. Suitable nitrogen protecting groups include, but are not limited to, carbamates—groups of the formula —C(O)O—R wherein R can be methyl, ethyl, t-butyl, benzyl, phenylethyl, $CH_2$=CH—$CH_2$—, and the like; amides—groups of the formula —C(O)—R' wherein R' can be methyl, phenyl, trifluoromethyl, and the like; N-sulfonyl derivatives—groups of the formula —$SO_2$—R" wherein R" can be tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, Protective Groups in Organic Synthesis, John Wiley & Sons, 1991.

As used herein the term "acyl" refers to a group of the formula —CO—$C_n$ wherein $C_n$ represent a straight or branched alkyl chain wherein n can be 1, 2, 3, 4, 5, 6, 7, 8, 9 or 10.

As used herein the term "heteroaryl" refers to any five or six membered monocyclic aromatic ring structure containing at least one heteroatom selected from the group consisting of O, N and S, and optionally containing one to three additional heteroatoms independently selected from the group consisting of O, N and S; or a nine or ten membered bicyclic aromatic ring structure containing at least one heteroatom selected from the group consisting of O, N and S, and optionally containing one to four additional heteroatoms independently selected from the group consisting of O, N and S. The heteroaryl group may be attached at any heteroatom or carbon atom of the ring such that the result is a stable structure. Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl and pteridinyl.

As used herein the term "cycloalkyl" refers to any monocyclic ring containing from four to six carbon atoms, or a bicyclic ring containing from eight to ten carbon atoms. The cycloalkyl group may be attached at any carbon atom of the ring such that the result is a stable structure. Examples of suitable cycloalkyl groups include, but are not limited to, cyclopropyl, cyclobutyl, cyclopentyl and cyclohexyl.

As used herein the term "heterocycle" refers to any four to six membered monocyclic ring structure containing at least one heteroatom selected from the group consisting of O, N and S, and optionally containing one to three additional heteroatoms independently selected from the group consisting of O, N and S; or an eight to ten membered bicyclic ring structure containing at least one heteroatom selected from the group consisting of O, N and S, and optionally containing one to four additional heteroatoms independently selected from the group consisting of O, N and S. The heterocycle group may be attached at any heteroatom or carbon atom of the ring such that the result is a stable structure. Examples of suitable heterocycle groups include, but are not limited to, azetidine, azete, oxetane, oxete, thietane, thiete, diazetidine, diazete, dioxetane, dioxete, dithietane, dithiete, pyrrolidine, pyrrole, tetrahydrofuran, furan, thiolane, thiophene, piperidine, oxane, thiane, pyridine, pyran and thiopyran.

The groups of the present disclosure can be unsubstituted or substituted, as herein defined. In addition, the substituted groups can be substituted with one or more groups such as a $C_1$-$C_6$ alkyl, $C_{1-4}$ alkyl, —O—$C_{1-4}$ alkyl, hydroxyl, amino, ($C_{1-4}$ alkyl)amino, di($C_{1-4}$ alkyl)amino, —S—($C_{1-4}$ alkyl), —SO—($C_{1-4}$ alkyl), —SO$_2$—($C_{1-4}$ alkyl), halogen, aryl, heteroaryl, and the like.

With reference to substituents, the term "independently" means that when more than one of such substituents is possible, such substituents may be the same or different from each other.

The compounds of the present disclosure can contain at least one hydroxyl group. These at least one hydroxyl group may form an ester with inorganic or organic acid. In particular, pharmaceutically acceptable acids. The ester(s) may form chiral carbons. The present disclosure is directed toward all stereo-chemical forms of the compounds of the present disclosure, including those formed by the formation of one or more ester groups.

In one embodiment, "a" can be 0, 1 or 2. In particular, "a" can be 1 or 2. More particular, "a" can be 1.

In another embodiment, $R^1$ can be $C_{1-12}$ alkyl or $C_{1-12}$ alkenyl. In particular, $R^1$ can be $C_{1-4}$ alkyl. More particular, $R^1$ can be a methyl group.

In another embodiment, $R^2$ is a $C_{1-12}$ alkyl optionally substituted with a cycloalkyl or heterocycle. The substituted cycloalkyl or heterocycle can be optionally substituted with a —COOH, —C(O)—$C_{1-4}$ alkyl, or —C(O)O—$C_{1-4}$ alkyl group. In particular, $R^2$ can be a methyl, ethyl, n-propyl, n-butyl, n-pentyl, n-hexyl, n-heptyl, n-octyl, 2-methyloctan-2-yl group or

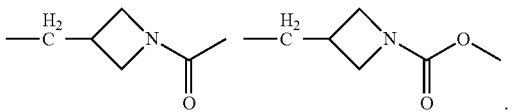

In one embodiment, $R^2$ can be a n-propyl group. In another embodiment, $R^2$ can be n-pentyl group. In another embodiment, $R^2$ can be

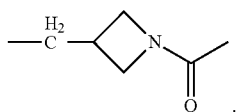

In another embodiment, $R^3$ is hydrogen or a $C_{1-4}$ alkyl. In particular, $R^3$ can be a hydrogen or a methyl group. More particular, $R^3$ can be hydrogen.

In yet another embodiment, "a" can be 1, $R^1$ can be a methyl group, $R^2$ can be a n-pentyl group and $R^3$ can be hydrogen.

Examples of compounds of formula (I) include ethyl cannabidiolate, delta-9-tetrahydrocannabidiol and delta-8-tetrahydrocannabidiol.

Examples of compounds of formula (II) include 4,6-dibromo-olivetol or 4,6-dibromo-divarinol.

Examples of compounds of formula (III) include menthadienol, 1-hydroxymethyl-4(1-methylethenyl)-cyclohex-2-ene-1-ol, and cyclohex-2-enol. In one embodiment, the coupling of dibromo-olivetol, and related compounds as provided in the present disclosure, can be performed using a cyclic olefin containing a double bond and a hydroxy-group at a conjugated position. Examples of compounds of formula (III) can also include a cyclic olefin containing a double bond and a hydroxy-group at a conjugated position.

In one embodiment, a suitably substituted compound of formula (II) being a known compound or compound prepared by known methods, wherein each X is independently selected from the group consisting of Br, F, I and Cl, particularly both X substituents are the same and are selected from the group consisting of Br, F, I and Cl, more particularly Br, F or Cl, or more particularly Br or F, or even more particularly Br, can be reacted with a suitably substituted compound of formula (III) being a known compound or compound prepared by known methods, wherein $R^0$ is H or a suitably selected leaving group such as OH, Cl, Br, F, I, tosylate, mesylate, acetate, and the like, in particular OH. The reaction can occur in the presence of a suitably selected protic or Lewis acid catalyst, for example p-toluene sulfonic acid, trifluoromethanesulfonic acid, trifluoroacetic acid, acetic acid, sulfuric acid, iron(II) chloride, scandium(III) triflate, zinc chloride, aluminum chloride, and the like. The reaction can occur neat or in a suitably selected solvent or mixture of solvents, for example methylene chloride, chloroform, 1,2-dichloroethane, cyclohexane, toluene, acetonitrile, tert-butyl methyl ether, or combinations thereof, and the like. The reaction can form a compound of formula (IV).

The compound of formula (IV) can be cyclized by reacting with a second suitably selected Lewis acid catalyst, for example $BF_3$ diethyl etherate, $BF_3$*AcOH, tri-isobutyl aluminum, and the like. The cyclization can also be performed using protic acids, such as p-toluene sulfonic acid. The cyclization reaction can occur in a suitably selected solvent or mixture of solvents, for example, methylene chloride, chlorobenzene, acetone, 1,2-dichloroethanen-heptane, acetonitrile, toluene, and the like. The cyclization reaction can form a compound of formula (V).

The compound of formula (V) can be reacted to remove the X substituent groups, more particularly, the compound of formula (V) can be reacted with a suitably selected reducing agent, for example, sodium sulfite, potassium sulfite, palladium/carbon in combination with hydrogen, and the like; in the presence of a suitably selected base, such as sodium hydroxide, triethylamine, sodium carbonate, tripotassium phosphate, potassium tert-butoxide, and the like. The reduction reaction can occur in a suitably selected polar solvent or mixture of polar solvents, or mixture of apolar and polar solvents, for example, methanol or a mixture of methanol and water, acetonitrile, ethanol, acetone, isopropanol, n-butanol, dichloromethane, tetrahydrofuran, tert-butyl methyl ether or a mixture of organic solvent and water, and the like. The polar solvent or mixture of polar solvents can also be selected from the group consisting of acetonitrile, methylene chloride, or combinations thereof, and the like. The reduction reaction can form the compound of formula (I).

The dihalo-compound, e.g., formula (II), can be contained in non-aqueous solvents or a mixture of solvents such as dichloromethane, toluene, tert-butyl methyl, n-heptane, and the like. The non-aqueous solvent can also contain a desiccating agent. The desiccating agent can be added to remove adventitious moisture from the reaction mixture. The amount of desiccating agent in the dihalo-compound solution can be up to about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30% (g of desiccating agent/mL of solvent). These values can be used to define a range, such as about 1 and about 10%, or about 10 and about 20%.

In one embodiment, the amount of desiccating agent can be about 5% to about 20% g/mL of anhydrous $MgSO_4$ per mL DCM. For example, a lower amount can be used, e.g., 5% g/mL, if the reagents are anhydrous, e.g., $MgSO_4$, dibromo-Olivetol, pTSA. A higher amount can be used, e.g., 20% g/mL, if the reagents are mono-hydrates, e.g., dibromo-Olivetol and pTSA mono-hydrates. In one embodiment, the amount can be about 14.5% g/mL. In some embodiments, the amount of desiccating agent can be 0% if the compound, e.g., menthadienol, is present in excess amounts, such as greater than about 3 eq.

The amount of desiccating agent per starting material can also be expressed as a molar ratio of desiccating agent to starting material. The amount can be about 1:1, 1.5:1, 2:1, 2.5:1, 3:1, 3.5:1, 4:1, 4.5:1 or about 5:1. These values can be used to define a range, such as about 1.5:1 to about 3.5:1. In one embodiment, the ratio is about 2.8:1.

The desiccating agent can be any agent or compound that does not interfere with the reaction and can remove moisture from the reaction mixture. The desiccating agent can be selected from the group consisting of an anhydrous inorganic salt, molecular sieve, activated charcoal, silica gel, or combinations thereof. In one embodiment, the desiccating agent is anhydrous magnesium sulfate.

The reaction between compounds of formula (III) and formula (II) can be carried out with the relative amounts of compounds of formula (III) and formula (II) of about 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4 or 5.5 equivalents of formula (III) to formula (II). These values can be used to define a range, such as about 0.5 and about 5 equivalents, or about 0.5 and about 3.5 equivalents or about 1.1 to about 1.7 equivalents.

The compound of formula (III) can be added to the compound of formula (II), or a solution containing formula (II), slowly. The compound of formula (III) can be added to the compound of formula (II), or a solution containing formula (II), over 0.1, 0.2, 0.3, 0.4, 0.5, 1, 1.5, 2, 2.5, 3, 3.5, 4, 4.5, 5, 5.5, 6, 7, 8, 9, 10, 11, 12, 16, 20 or about 24 hours. These values can be used to define a range, such about 2 to about 12 hours, or about 4 to about 8 hours. The compound can be added in increments or portions over the time period. For example, the compound can be added over 7 hours as follows: t=0: 0.65 eq; t=1 h: +0.65 eq; t=4 h: +0.3 eq and optionally t=7 h: +0.1 eq.

After addition, the reaction mixture can be stirred for an additional time. The reaction mixture can be stirred for an additional 0.1, 0.2, 0.3, 0.4, 0.5, 0.6, 0.7, 0.8, 0.9, 1, 2, 3, 4, 5, 6, 7, 8, 9, 10, 12, 16, 20, 24, 36 or 48 hours. These values can be used to define a range, such as about 1 to about 3 hours, or about 6 to about 48 hours, or about 12 to about 24 hours, or about 14 to about 18 hours.

One skilled in the art will recognize that the reaction or process step(s) as herein described can proceed for a sufficient period of time until the reaction is complete, as determined by any method known to one skilled in the art, for example, chromatography (e.g., HPLC). In this context a "completed reaction or process step" shall mean that the reaction mixture contains a significantly diminished amount of the starting material(s)/reagent(s)/intermediate(s) and a significantly reduced amount of the desired product(s), as compared to the amounts of each present at the beginning of the reaction.

During the addition, during the additional stir time or both, the reaction mixture can be held at a specific temperature or held within a range of temperatures. The reaction mixture can be held at −80° C., −70° C., −60° C., −50° C., −40° C., −30° C., −20° C., −10° C., 0° C., 10° C., 20° C., 30° C., 40° C., 50° C., 60° C., 70° C., 80° C., 90° C., 100° C., 110° C. or about 120° C. These values can be used to define a range, such as about −40° C. to about 40° C., or about −35° C. to about −25° C., or about −0° C. to about 50° C.

The reaction between compounds of formula (III) and formula (II) can be carried out in the presence of a protic or Lewis acid catalyst. The protic acid can be an alkyl sulfonic acid or an aryl sulfonic acid wherein the alkyl group can be a $C_1$-$C_{10}$ alkyl, and the aryl group can be a phenyl. The protic acid can be an alkyl-phenyl sulfuric acid or fluorosulfonic acid or hydrohalic acid where the halogen is F, Cl, Br or I. In one embodiment, the protic acid is p-toluenesulfonic acid, acetic acid, sulfuric acid, trifluoroacetic acid, scandium triflate, oxalic acid, benzoic acid, phosphoric acid, formic acid or combinations thereof.

The Lewis acid catalyst can be of the general formula MY wherein M can be boron, aluminum, scandium, titanium, yttrium, zirconium, lanthanum, lithium, hafnium, or zinc and Y can be F, Cl, Br, I, trifluoroacetate (triflate), alkoxide or combinations thereof. The Lewis acid catalyst can be selected from the group consisting of zinc triflate, ytterbium triflate, yttrium triflate, scandium triflate and combinations thereof. In one embodiment, the Lewis acid catalyst is a triflate, such as zinc triflate or scandium triflate.

The amount of the protic or Lewis acid catalyst, e.g., p-toluenesulfonic acid, in the reaction between compounds of formula (III) and formula (II) can be about 0.5 mol %, 1 mol %, 2 mol %, 3 mol %, 4 mol %, 5 mol %, 6 mol %, 7 mol %, 8 mol %, 9 mol %, 10 mol %, 20 mol %, 30 mol %, 40 mol %, 50 mol %, 60 mol %, 70 mol %, 80 mol %, 90 mol %, 100 mol %, or about 120 mol % with respect to the compound of formula (II). These values can be used to define a range, such as about 4 mol % to about 6 mol %, 20 mol % to about 80 mol %, or about 40 mol % to about 60 mol %.

The reaction between compounds of formula (III) and formula (II) can be carried out in an organic solvent. The organic solvent can be aprotic. The organic solvent can be selected from the group consisting of methylene chloride, chloroform, trichloroethylene, methylene bromide, bromoform, hexane, heptane, toluene, xylene, and combinations thereof.

The compound of formula (IV) can be cyclized to form a compound of formula (V) in the presence of a Lewis acid catalyst, protic acid, or combinations thereof.

The Lewis acid catalyst can be of the general formula MY wherein M can be boron, aluminum, scandium, titanium, yttrium, zirconium, lanthanum, lithium, hafnium or zinc, and Y can be can be F, Cl, Br, I, trifluoroacetate (triflate), alkoxide or combinations thereof. The Lewis acid catalyst can be selected from the group consisting of zinc triflate, ytterbium triflate, yttrium triflate, scandium triflate and combinations thereof. In one embodiment, the Lewis acid catalyst is a triflate, such as zinc triflate or scandium triflate.

The amount of Lewis acid catalyst in the cyclization reaction can be about 0.5 mol %, 1 mol %, 2 mol %, 5 mol %, 10 mol %, 20 mol %, 30 mol %, 40 mol %, 50 mol %, 60 mol %, 70 mol %, 80 mol %, 90 mol %, 100 mol %, or about 120 mol % with respect to the compound of formula (IV). These values can be used to define a range, such as about 0.5 mol % to about 10 mol %.

The cyclization reaction can be carried out in carried out in a suitably selected organic solvent or mixture of organic solvents. The organic solvent can be selected from the group consisting of a hydrocarbon, aromatic hydrocarbon, halogenated hydrocarbon, ether, ester, amide, nitrile, carbonate, alcohol, carbon dioxide, and mixtures thereof. In one embodiment, the organic solvent is dichloromethane.

The temperature of the cyclization reaction can be held at a specific temperature or held within a range of temperatures. The reaction mixture can be held at −40° C., −30° C., −20° C., −10° C., 0° C., 10° C., 20° C., 30° C., 40° C., 50° C., 60° C., 70° C., 80° C., 90° C., 100° C., 110° C. or about 120° C. These values can be used to define a range, such as about −20° C. to about 50° C., or about 0° C. to about 30° C.

The compound of formula (V) can be reacted with a reducing agent to form the compound of formula (I). The compound of formula (V) can be dissolved in a polar solvent and can be treated with a reducing agent in the presence of a base to produce the compound of formula (I).

The polar solvent can be water, alcohol, or combinations thereof, e.g., a water-alcohol mixture. The alcohol can be selected from the list consisting of methanol, ethanol, 1-propanol, 2-propanol, 1-butanol, 2-butanol, 2-methyl-1-propanol and 2-methyl-2-propanol. In one embodiment, the solvent is methanol.

As used herein, the term "reducing agent" refers to an agent having the ability to add one or more electrons to an atom, ion or molecule. The reducing agent can be a sulfur-containing compound, or Pd/C in the presence of hydrogen. The sulfur containing compound can be a sulfur-containing reducing agent having the ability to reduce C—X bonds of a compound of formula (IV) to C—H bonds.

The sulfur-containing compound can be a sulfur-containing inorganic acid or salt thereof, including, for example, hydrosulfuric acid ($H_2S$), sulfurous acid ($H_2SO_3$), thiosulfurous acid ($H_2SO_2O_2$), dithionous acid ($H_2S_2O_4$), disulfurous acid ($H_2S_2O_5$), dithionic acid ($H_2S_2O_2$), trithionic acid ($H_2S_3O_6$) and salts thereof. The sulfur-containing inorganic salt can be an alkali metal salt or an alkaline earth metal salt. For example, the salt can be a monovalent or divalent cation selected from $Li^+$, $Na^+$, $K^+$, $Rb^+$, $Cs^+$, $Fr^+$, $Be^{2+}$, $Mg^{2+}$, $Ca^{2+}$, $Sr^{2+}$, $Ba^{2+}$, or $Ra^{2+}$. In one embodiment, the salt can be selected from the group consisting of $Li^+$, $Na^+$, $K^+$, $Mg^{2+}$, $Ca^{2+}$ and combinations thereof.

The sulfur-containing inorganic salt can also be an ammonium salt ($NH_4^+$) or a quaternary ammonium salt. For example, the sulfur-containing inorganic acid salt can be a tetraalkylated ammonium salt, e.g., a quaternary ammonium salt substituted with four alkyl groups. The alkyl groups can be a $C_1$-$C_{18}$. The tetraalkylated ammonium salts can be a tetramethylammonium salt, a tetraethylammonium salt, a tetrapropylammonium salt, a tetrabutylammonium salt, or combinations thereof.

The sulfur-containing inorganic acid or salt thereof can also be one which dissociates into a bisulfite ion ($HSO_3^-$) and/or a sulfite ion ($SO_3^{2-}$) in the reaction mixture. Sulfurous acid ($H_2SO_3$) can generally exist as a solution of $SO_2$ (commonly about 6%) in water. The pKa of sulfurous acid ($H_2SO_3$) is about 1.78 and its ionization expression is: $H_2O+SO_2 \leftrightarrow H_2SO_3 \leftrightarrow H^+ + HSO_3^- \leftrightarrow H^+ + SO_3^{2-}$. In one embodiment, the sulfur-containing compound is sodium sulfite.

The molar ratio amount of sulfur-containing compound to the compound of formula (IV) in the reduction reaction mixture can be about 0.8:1, 1:1, 1.5:1, 2:1, 3:1, 4:1, 5:1 or greater. These values can define a range, such as about 2:1 to about 4:1, or about 2.5:1 to about 3.5:1. In one embodiment, the ratio is about 3:1.

The base can be an organic or weak inorganic base. In one embodiment, the base can be an organic base, e.g., a tertiary amine. The base can be selected from the group consisting of trimethylamine, triethylamine, tripropylamine, diisopropylmethylamine, N-methylmorpholine, triethanolamine and combinations thereof. In one embodiment, the base is triethylamine. In another embodiment, the base can be a weak inorganic base, e.g., a carbonate or bicarbonate salt. The base can be a carbonate or bicarbonate salt selected from the group consisting of $Li^+$, $Na^+$, $K^+$, $Mg^{2+}$, $Ca^{2+}$ and combinations thereof.

The molar ratio amount of base to the compound of formula (IV) in the reduction reaction mixture can be about 0:1, 1:1, 1.5:1, 2:1, 3:1, 4:1, 5:1, 6:1, 7:1, 8:1 or greater. These values can define a range, such as about 3.5:1 to about 4.5:1, or about 4:1 to about 6:1. In one embodiment, the ratio is about 4:1.

The reduction reaction can be carried out at a reflux temperature, including a temperature elevated by high pressure, of the solvent or solvent mixture for a duration of about 1, 2, 3, 4, 5, 6, 7, 8, 9, 10, 12, 16, 20, 24, 28, 30, 32, 36 or about 48 hours; or any amount of time required to reach a desired endpoint (wherein the desired endpoint can be determined by for example, a percent conversion of starting material or an intermediate material). In some embodiments, the conversion of the di-halogen to the mono-halogen proceeds faster than the conversion of the mono-halogen to the fully dehalogenated product. These values can define a range, such as about 10 to about 30 hours. In one embodiment, the reduction reaction can be carried out at reflux in a methanol-water mixture for a duration of about 16 hours to about 24 hours, or about 20 to about 28 hours.

The reflux temperature can be at 20° C., Room Temperature, 30° C., 40° C., 50° C., 60° C., 65° C., 70° C., 75° C., 80° C., 85° C., 90° C., 95° C., 100° C., 110° C. or about 120° C. These values can be used to define a range, such as about 20° C. to about 100° C., or about RT to about 50° C., or about 60° C. to about 85° C., or about 72° C. to about 76° C. In some embodiments, subsequent distillation can be performed. The distillation can be performed at the same temperatures listed above, e.g., 85° C.

The reflux pressure can be at atmospheric pressure. In some embodiments, the reflex can be done at a pressure of about 100, 200, 300, 400, 500, 600, 700, 800, 900, 1000, 1500, 2000, 2500, 3000, 3500, or about 4000 mbar. These values can be used to define a range, such as about 900 to about 3000 mbar.

The reaction products, e.g., the reduction reaction products, of the present disclosure can further be purified by chromatography, countercurrent extraction, distillation, or combinations thereof. The reaction products of the present disclosure can also be purified by crystallization.

In another embodiment, the present disclosure relates to a process for the preparation of a compound of formula (I) including reacting a compound of formula (II) with a compound of formula (III) in the presence of a protic or first Lewis acid catalyst to form a compound of formula (IV), as described above. The compound of formula (IV) can then be reacted with a reducing agent to form a compound of formula (VI).

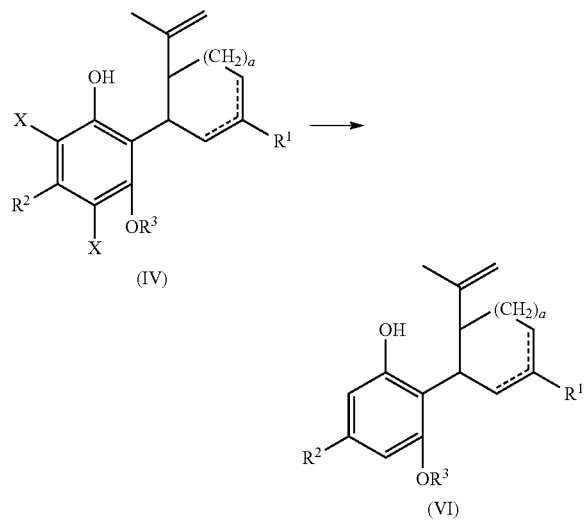

(IV)

(VI)

The compound of formula (IV) can be dissolved in a polar solvent and can be treated with a reducing agent in the presence of a base to produce the compound of formula (VI). The reduction reaction, conditions, components, parameters, etc. are similar to the reaction of a compound of formula (V) reacting with a reducing agent to form the compound of formula (I), as described above.

The compound of formula (VI) can then be reacted with a second Lewis acid catalyst to form the compound of formula (I).

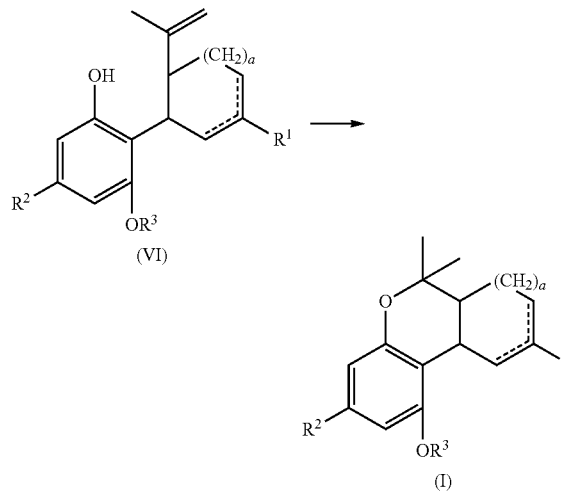

(VI)

(I)

The cyclization reaction, conditions, components, parameters, etc. are similar to the cyclization reaction of a compound of formula (IV) in the presence of a Lewis acid catalyst to form a compound of formula (V), as described above.

In one embodiment, a suitably substituted compound of formula (II) being a known compound or compound prepared by known methods, wherein each X is independently selected from the group consisting of Br, F, I and Cl, particularly both X substituent groups are the same and are selected from the group consisting of Br, F, I and Cl, more particularly Br F or Cl, or more particularly Br or F, or even more particularly Br, is reacted with a suitably substituted compound of formula (III), being a known compound or compound prepared by known methods, wherein $R^0$ is H or a suitably selected leaving group such as OH, Cl, Br, F, I, tosylate, mesylate, acetate, and the like, particularly OH, in the presence of a suitably selected protic or Lewis acid catalyst, for example p-toluene sulfonic acid. The reaction can occur in a suitably selected solvent or mixture of solvents, for example methylene chloride. The reaction can form a compound of formula (IV).

The compound of formula (IV) can be reacted to remove the X substituent groups, more particularly, the compound of formula (IV) can be reacted with a suitably selected reducing agent, for example sodium sulfite. The reaction can occur in a suitably selected polar solvent or mixture of polar solvents, for example methanol or a mixture of methanol and water. The reaction can form a compound of formula (VI).

The compound of formula (VI) can be cyclized by reacting with a suitably selected second Lewis acid catalyst, for example $BF_3$, in a suitably selected solvent or mixture of solvents, for example methylene chloride. The cyclization reaction can form a compound of formula (I).

In different embodiments, the processes of the present disclosure can be used to form compounds of the various formulas provided that either the first, second or both Lewis acid catalyst(s) is not an organo-aluminum Lewis acid catalyst.

In another embodiment, the present disclosure relates to a process for the preparation of a compound of formula (VI)

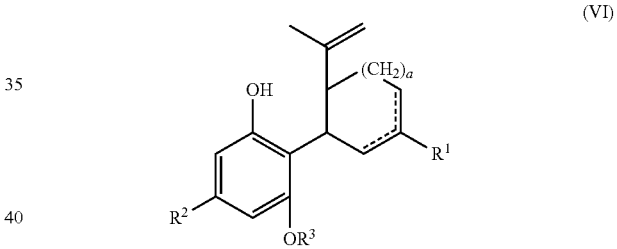

(VI)

wherein a, $R^1$, $R^2$, $R^3$ and ═══════ are defined above, unless otherwise specified below, or a pharmaceutically acceptable salt or ester thereof. The process includes reacting a compound of formula (II), wherein each X is independently selected from the group consisting of Br, F, I and Cl, with a compound of formula (III) wherein $R^0$ is H or OH (or as otherwise defined herein) in the presence of a protic or first Lewis acid catalyst to form a compound of formula (IV), as described above. The compound of formula (IV) can then be reacted with a reducing agent to form a compound of formula (VI).

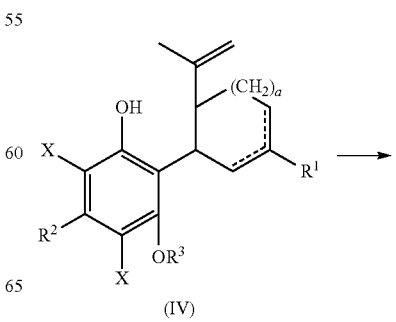

(IV)

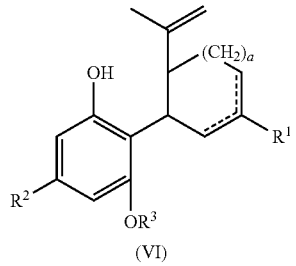

(VI)

The compound of formula (IV) can be dissolved in a polar solvent and can be treated with a reducing agent in the presence of a base to produce the compound of formula (VI). The reduction reaction, conditions, components, parameters, etc. are similar to the reaction of a compound of formula (V) reacting with a reducing agent to form the compound of formula (I), as described above.

In one embodiment, "a" can be 0, 1 or 2. In particular, "a" can be 1 or 2. More particular, "a" can be 1.

In another embodiment, $R^1$ can be $C_{1-12}$ alkyl or $C_{1-12}$ alkenyl. In particular, $R^1$ can be $C_{1-4}$ alkyl. More particular, $R^1$ can be a methyl group.

In another embodiment, $R^2$ can be a $C_{1-12}$ alkyl optionally substituted with a cycloalkyl or heterocycle. The substituted cycloalkyl or heterocycle can be optionally substituted with a —COOH, —C(O)—$C_{1-4}$ alkyl, or —C(O)O—$C_{1-4}$ alkyl group. In particular, $R^2$ can be a methyl, ethyl, n-propyl, n-butyl, n-pentyl, n-hexyl, n-heptyl, n-octyl, 2-methyloctan-2-yl group or

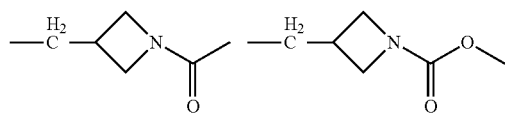

In one embodiment, $R^2$ can be a n-propyl group. In another embodiment, $R^2$ can be n-pentyl group. In another embodiment, $R^2$ can be

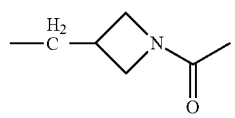

In another embodiment, $R^3$ can be hydrogen or a $C_{1-4}$ alkyl. In particular, $R^3$ can be a hydrogen or a methyl group. More particular, $R^3$ can be hydrogen.

In yet another embodiment, "a" can be 1, $R^1$ can be a methyl group, $R^2$ can be a n-propyl or n-pentyl group and $R^3$ can be hydrogen.

Examples of compounds of formula (VI) include cannabidiol, cannabidivarin and

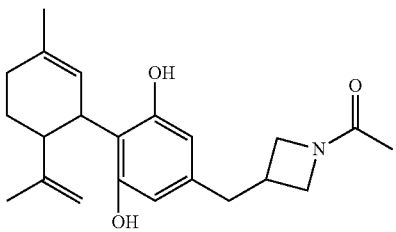

(XX)

In another embodiment, the present disclosure relates to a process for the preparation of a compound of formula (XI) (delta-9-tetrahydrocannabidiol)

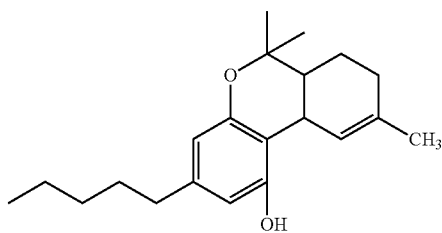

(XI)

or a pharmaceutically acceptable salt or ester thereof;
the process can include reacting a compound of formula (XII), wherein each X is independently selected from Br, F, I or Cl, with a compound of formula (XIII) (menthadienol) in the presence of a protic or first Lewis acid catalyst to form a compound of formula (XIV).

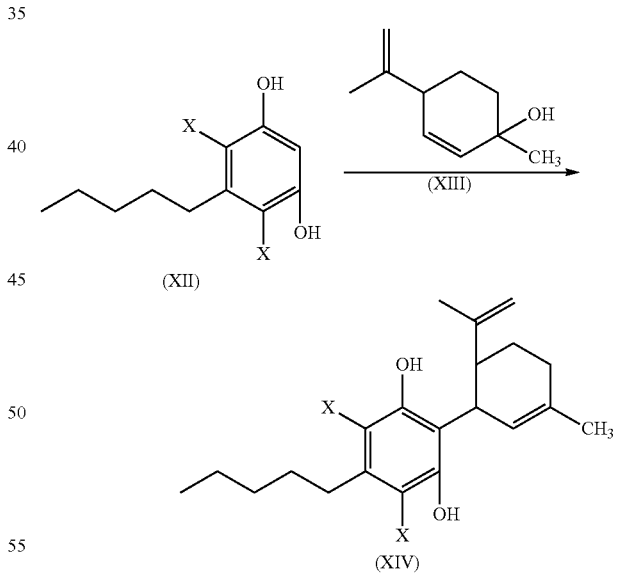

The reaction, conditions, components, parameters, etc. of the reaction of formula (XII) with a compound of formula (XIII) in the presence of a protic or first Lewis acid catalyst to form a compound of formula (XIV) are similar to the reaction of a compound of formula (II) reacting with a compound of formula (III) to form the compound of formula (IV), as described above.

The compound of formula (XIV) can then be cyclized by reacting the compound of formula (XIV) with a second Lewis acid catalyst to form a compound of formula (XV).

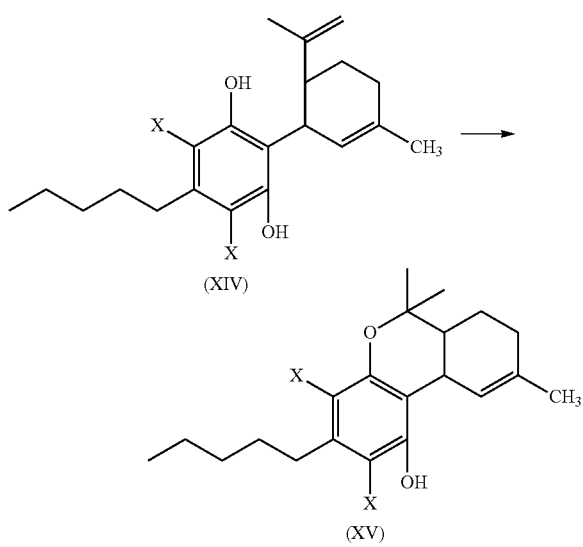

(XIV)

(XV)

The cyclization reaction, conditions, components, parameters, etc. of the reaction of formula (XIV) with a second Lewis acid catalyst to form a compound of formula (XV) are similar to the cyclization reaction of a compound of formula (IV) in the presence of a Lewis acid catalyst to form a compound of formula (V), as described above.

The compound of formula (XV) can then be reacted with a reducing agent to form the compound of formula (XI).

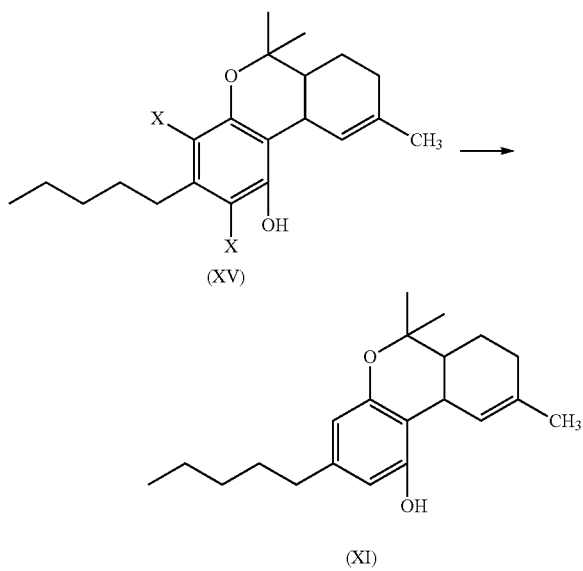

(XV)

(XI)

The compound of formula (XV) can be dissolved in a polar solvent and can be treated with a reducing agent in the presence of a base to produce the compound of formula (XI). The reduction reaction, conditions, components, parameters, etc. of formula (XV) with a reducing agent to form a compound of formula (XI) are similar to the reaction of a compound of formula (V) reacting with a reducing agent to form the compound of formula (I), as described above.

In one embodiment, a suitably substituted compound of formula (XII), being a known compound or compound prepared by known methods, wherein each X is independently selected from the group consisting of Br, F, I and Cl; particularly both X substituent groups are the same and are selected from the group consisting of Br, F, I and Cl, more particularly Br, F or Cl, or more particularly Br or F, or even more particularly Br, can be reacted with a suitably substituted compound of formula (XIII), being a known compound or compound prepared by known methods, wherein $R^0$ is H or a suitably selected leaving group such as OH, Cl, Br, F, I, tosylate, mesylate, acetate, and the like, particularly OH, in the presence of a suitably selected protic or Lewis acid catalyst, for example p-toluene sulfonic acid. The reaction can occur in a suitably selected solvent or mixture of solvents, for example methylene chloride. The reaction can form a compound of formula (XIV).

The compound of formula (XIV) can then be cyclized by reacting with a suitably selected second Lewis acid catalyst, for example $BF_3$, in a suitably selected solvent or mixture of solvent for example methylene chloride. The cyclization reaction can form a compound of formula (XV).

The compound of formula (XV) can be reacted to remove the X substituent groups, more particularly, the compound of formula (XV) can be reacted with a suitably selected reducing agent, for example sodium sulfite; in a suitably selected solvent or mixture of solvents, for example methanol or a mixture of methanol and water. The reaction can form the compound of formula (XI).

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. "R" and "S" represent the configuration of substituents around one or more chiral carbon atoms.

"Racemate" or "racemic mixture" means a compound of equimolar quantities of two enantiomers, wherein such mixtures exhibit no optical activity, i.e., they do not rotate the plane of polarized light.

The compounds of the present disclosure may be prepared as individual enantiomers by either enantio-specific synthesis or resolved from an enantiomerically enriched mixture. When the stereochemistry of a disclosed compound is named or depicted, the named or depicted stereoisomer can be at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

In another embodiment, the present disclosure can produce the compounds of interest, e.g., compounds of formula (I), (VI), (XI), (XVI), etc., in high stereospecificity, from the starting materials, e.g., compounds of formula (II), etc. The stereospecificity of the processes of the present disclosure can be greater than about 60% ee, 75% ee, 80% ee, 85% ee, 90% ee, 95% ee, 97% ee, 98% ee, 99% ee. These values can define a range, such as about 90% ee and about 99% ee.

Compounds that can be produced by the process of the present disclosure can include (−)-trans-cannabidiol, (−)-trans-Δ-9-tetrahydrocannabinol, (−)-trans-cannabidiolic acid, (−)-trans-Δ-9-tetrahydrocannabinolic acid, intermediate compounds thereof, derivative compounds thereof, as well as the corresponding (+) enantiomer, and racemates.

The following table lists some of these compounds.

| | Structure | Chemical name (IUPAC) |
|---|---|---|
| (−)-CBD | 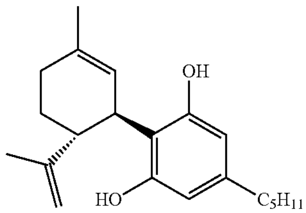 | (1'R,2'R)-5'-methyl-4-pentyl-2'-(prop-1-en-2-yl)-1',2',3',4'-tetrahydro-[1,1'-biphenyl]-2,6-diol |
| (+)-CBD | 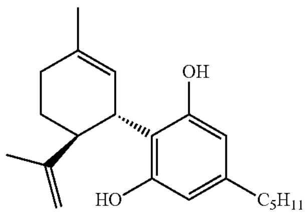 | (1'S,2'S)-5'-methyl-4-pentyl-2'-(prop-1-en-2-yl)-1',2',3',4'-tetrahydro-[1,1'-biphenyl]-2,6-diol |
| (−)-Δ6-CBD | 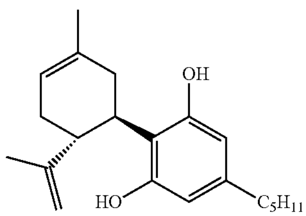 | (1'R,2'R)-5'-methyl-4-pentyl-2'-(prop-1-en-2-yl)-1',2',3',6'-tetrahydro-[1,1'-biphenyl]-2,6-diol |
| (+)-Δ6-CBD | 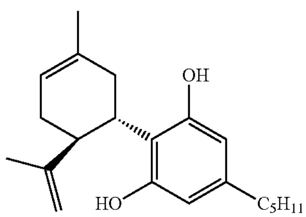 | (1'S,2'S)-5'-methyl-4-pentyl-2'-(prop-1-en-2-yl)-1',2',3',6'-tetrahydro-[1,1'-biphenyl]-2,6-diol |
| (−)-Δ9-THC | 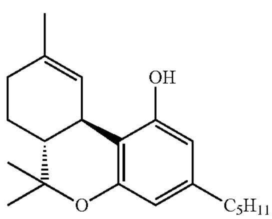 | (6aR,10aR)-6,6,9-trimethyl-3-pentyl-6a,7,8,10a-tetrahydro-6H-benzo[c]chromen-1-ol |
| (+)-Δ9-THC | 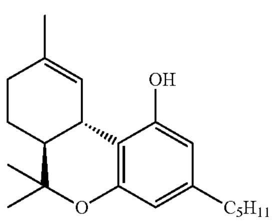 | (6aS,10aS)-6,6,9-trimethyl-3-pentyl-6a,7,8,10a-tetrahydro-6H-benzo[c]chromen-1-ol |
| (−)-Δ8-THC | 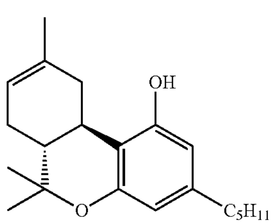 | (6aR,10aR)-6,6,9-trimethyl-3-pentyl-6a,7,10,10a-tetrahydro-6H-benzo[c]chromen-1-ol |

| Structure | Chemical name (IUPAC) |
|---|---|
| (+)-Δ8-THC | (6aS,10aS)-6,6,9-trimethyl-3-pentyl-6a,7,10,10a-tetrahydro-6H-benzo[c]chromen-1-ol |
| (−)-(I) | |
| (+)-(I) | |
| (−)-(VI) | |
| (+)-(VI) | |

In another embodiment, the present disclosure relates to a process for the preparation of a compound of formula (XI) (delta-9-tetrahydrocannabidiol)

or a pharmaceutically acceptable salt or ester thereof;

the process can include reacting a compound of formula (XII), wherein each X is independently selected from Br, F, I or Cl, with a compound of formula (XIII) (menthadienol) in the presence of a protic or first Lewis acid catalyst to for a compound of formula (XIV).

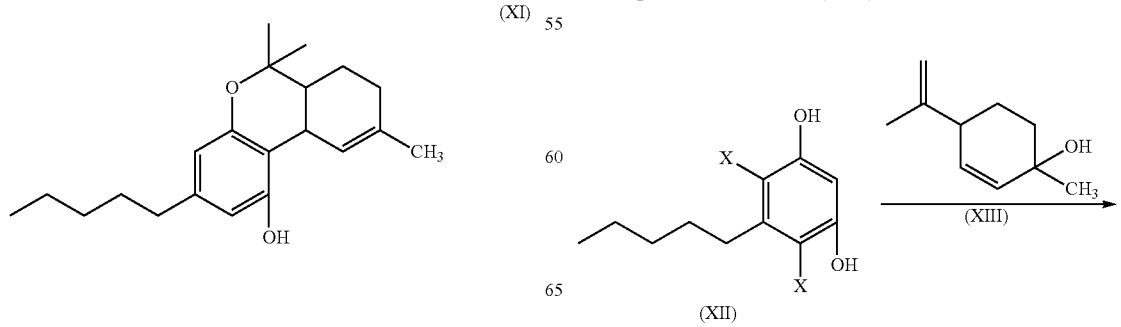

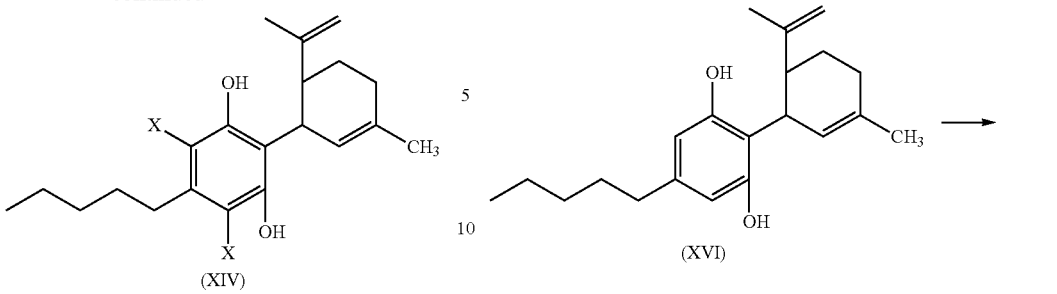

(XIV)

The reaction, conditions, components, parameters, etc. of the reaction of formula (XII) with a compound of formula (XIII) in the presence of a protic or first Lewis acid catalyst to form a compound of formula (XIV) are similar to the reaction of a compound of formula (II) reacting with a compound of formula (III) to form the compound of formula (IV), as described above.

The compound of formula (XIV) can then be reacted with a reducing agent to form the compound of formula (XVI).

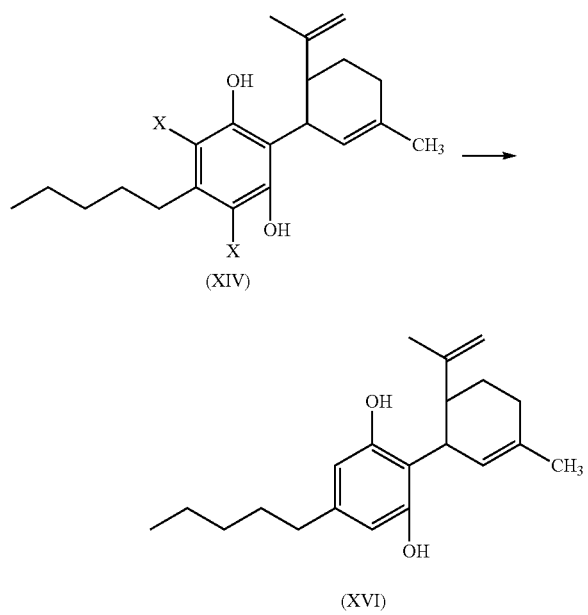

The compound of formula (XIV) can be dissolved in a polar solvent and can be treated with a reducing agent in the presence of a base to produce the compound of formula (XVI). The reduction reaction, conditions, components, parameters, etc. of formula (XIV) with a reducing agent to form a compound of formula (XVI) are similar to the reaction of a compound of formula (V) reacting with a reducing agent to form the compound of formula (I), as described above.

The compound of formula (XVI) can then be cyclized by reacting the compound of formula (XVI) with a second Lewis acid catalyst to form a compound of formula (XI).

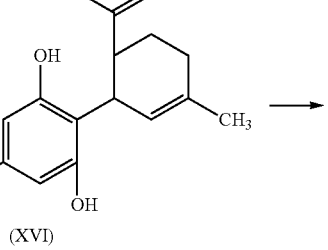

(XVI)

(XI)

The cyclization reaction, conditions, components, parameters, etc. of the reaction of formula (XVI) with a second Lewis acid catalyst to form a compound of formula (XI) are similar to the cyclization reaction of a compound of formula (IV) in the presence of a Lewis acid catalyst to form a compound of formula (V), as described above.

In another embodiment, a suitably substituted compound of formula (XII), being a known compound or compound prepared by known methods, wherein each X is independently selected from the group consisting of Br, F, I and Cl; particularly both X substituent groups are the same and are selected from the group consisting of Br, F, I and Cl, more particularly Br, F or Cl, or more particularly Br or F, or even more particularly Br, is reacted with a suitably substituted compound of formula (XIII), being a known compound or compound prepared by known methods, wherein $R^0$ is H or a suitably selected leaving group such as OH, Cl, Br, F, I, tosylate, mesylate, acetate, and the like, preferably OH, in the presence of a suitably selected protic or Lewis acid catalyst, for example p-toluene sulfonic acid. The reaction can occur in a suitably selected solvent or mixture of solvents, for example methylene chloride. The reaction can form a compound of formula (XIV).

The compound of formula (XIV) can be reacted to remove the X substituent groups, more particularly, the compound of formula (XIV) can be reacted with a suitably selected reducing agent, for example sodium sulfite. The reaction can occur in a suitably selected solvent or mixture of solvents, for example methanol or a mixture of methanol and water. The reaction can form a compound of formula (XVI).

The compound of formula (XVI) can be cyclized by reacting with a suitably selected second Lewis acid catalyst, for example $BF_3$, in a suitably selected solvent or mixture of solvent, for example methylene chloride. The cyclization reaction can form the compound of formula (XI).

In another embodiment, the present disclosure relates to a process for the preparation of a compound of formula (XVI) (cannabidiol)

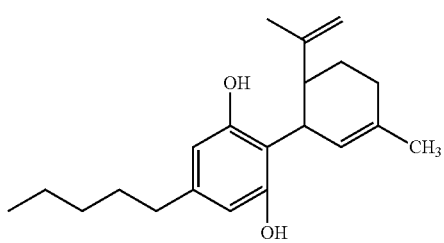

(XVI)

or a pharmaceutically acceptable salt or ester thereof;

the process can include reacting a compound of formula (XII), wherein each X is independently selected from Br, F, I or Cl, with a compound of formula (XIII) (menthadienol) in the presence of a protic or first Lewis acid catalyst to form a compound of formula (XIV).

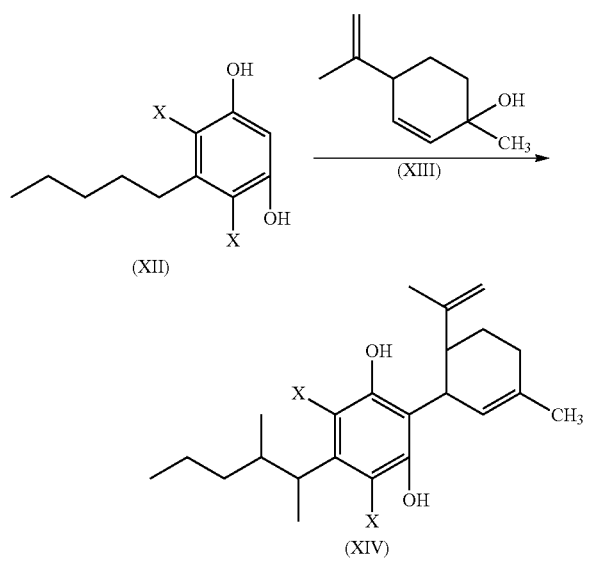

The reaction, conditions, components, parameters, etc. of the reaction of formula (XII) with a compound of formula (XIII) in the presence of a protic or first Lewis acid catalyst to form a compound of formula (XIV) are similar to the reaction of a compound of formula (II) reacting with a compound of formula (III) to form the compound of formula (IV), as described above.

The compound of formula (XIV) can then be reacted with a reducing agent to form the compound of formula (XVI).

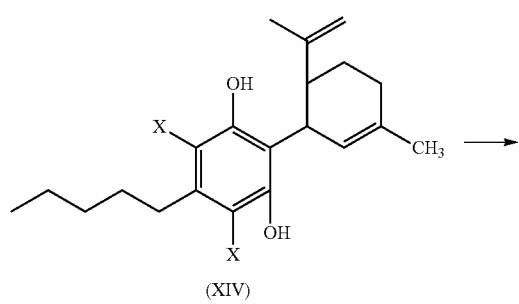

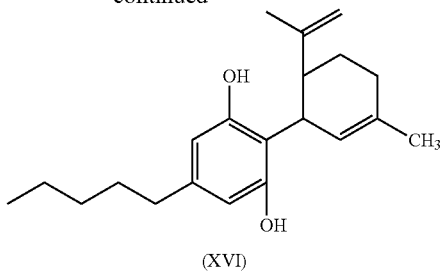

-continued (XVI)

The compound of formula (XIV) can be dissolved in a polar solvent and can be treated with a reducing agent in the presence of a base to produce the compound of formula (XVI). The reduction reaction, conditions, components, parameters, etc. are similar to the reaction of a compound of formula (V) reacting with a reducing agent to form the compound of formula (I), as described above.

In another embodiment, the present disclosure relates to a process for the preparation of a compound of formula (XX)

(XX)

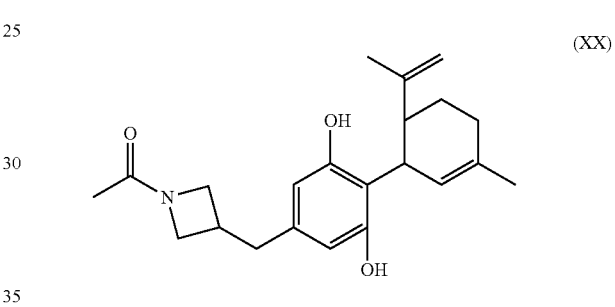

or a pharmaceutically acceptable salt or ester thereof, the process can include reacting a compound of formula (XXI), wherein each X is independently selected from Br, F, I or Cl, with a compound of formula (XIII) in the presence of a protic or first Lewis acid catalyst to form a compound of formula (XXII); and

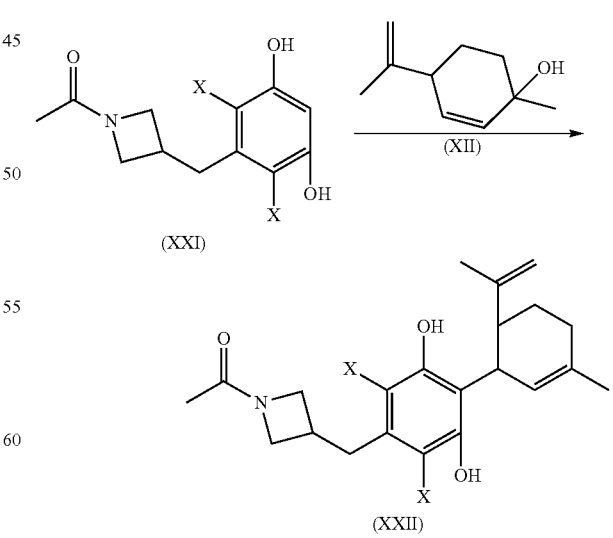

reacting the compound of formula (XXII) with a reducing agent to form the compound of formula (XX)

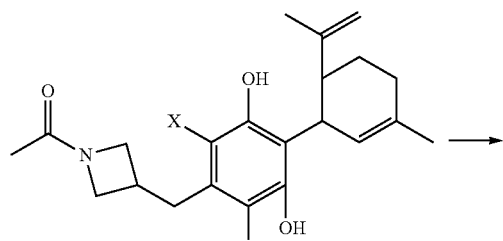

(XXII)

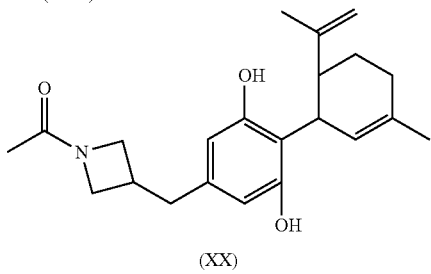

(XX)

The compound of formula (XXII) can be dissolved in a polar solvent and can be treated with a reducing agent in the presence of a base to produce the compound of formula (XX). The reduction reaction, conditions, components, parameters, etc. are similar to the reaction of a compound of formula (V) reacting with a reducing agent to form the compound of formula (I), as described above.

The present disclosure can produce the compounds of interest, e.g., compounds of formula (I), (VI), (XI), (XVI), etc., in high yield, from the starting materials, e.g., compounds of formula (II). The yield of the process of the present disclosure can be greater than about 60%, 61%, 62%, 63%, 64%, 65%, 66%, 67%, 68%, 69%, 70%, 71%, 72%, 73%, 74%, 75%, 76%, 77%, 78%, 79%, 80%, 80%, 81%, 82%, 83%, 84%, 85%, 86%, 87%, 88%, 89%, 90%, 91%, 92%, 93%, 94%, 95%, 96%, 97%, 98% or 99%. These values can define a range, such as about 60% to about 85%, or about 90% to about 99%.

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1—Synthesis of Cannabidiol from 4,6-dibromo-Olivetol

Cannabidiol, or (1'R,2'R)-5'-methyl-4"-pentyl-2'-(prop-1-en-2-yl)-1',2',3',4'-tetrahydro-[1,1"-biphenyl]-2",6'-diol, was prepared according to the present disclosure.

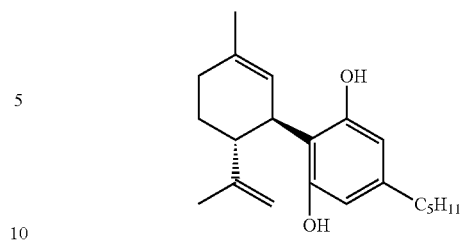

Under a $N_2$ atmosphere, 4,6-dibromo-olivetol (20.08 g, 59.40 mmol), magnesium sulfate (20.00 g, 164.5 mmol, 2.77 equiv.) and para toluene sulfonic acid monohydrate (5.76 g, 29.8 mmol, 0.50 equiv.) were suspended in $CH_2Cl_2$ (187.4 g) and cooled to between about −15 to −20° C. To this white suspension a clear solution of menthadienol (11.72 g, 76.99 mmol, 1.30 equiv.) in $CH_2Cl_2$ (55.13 g) was added dropwise over 6 hours. After stirring overnight at −15° C., the suspension was quenched with water (200.6 g). $NaHCO_3$ (5.01 g, 59.6 mmol, 1.00 equiv.) was added in portions and the mixture was stirred for about 10 to 30 min at room temperature. The layers were separated and the aqueous layer was re-extracted with $CH_2Cl_2$ (50.1 g). The organic layer was concentrated to dryness (in vacuum).

The remaining viscous oil was dissolved in methanol (200 g). This solution was combined with a solution of $Na_2SO_3$ (22.3 g, 177 mmol, 3 equiv.) in water (200 g). To the remaining white suspension, N,N-diethylethanamine (29.9 g, 295 mmol, 5.00 equiv.) was added and the suspension was heated to reflux and stirred for 20 hours. After re-cooling of the reaction mixture to room temperature, conc. HCl (37 wt %) (16.2 g, 164 mmol, 2.78 equiv.) was added dropwise within 20 to 30 min to a pH value of 6.5 (at 20° C.). N-heptane (80 g) was then added. The yellowish emulsion was stirred for about 20 min at 30° C. The layers were separated. The aqueous layer was re-extracted with n-heptane (50 g). The combined organic layers were dried over $Na_2SO_4$, filtered and concentrated to have a ratio of cannabidiol to n-heptane of 1:4. The solution was seeded and cooled to −15° C. over about 2 to 3 hours. The product was isolated and washed with n-heptane.

The remaining white solid (m=16.0 g), was re-dissolved in n-heptane (64 g) at 40° C., cooled to 0° C. and stirred for 1 to 2 h at 0° C. The product was isolated, washed with n-heptane and dried in vacuum at 40-50° C. The obtained white crystalline powder (m=14.7 g, 79%) was analyzed by UPLC with 99.96 area %.

Example 2—Variation of the Chain Length ($C_3H_7$ and $C_5H_{11}$)

Figure 4:
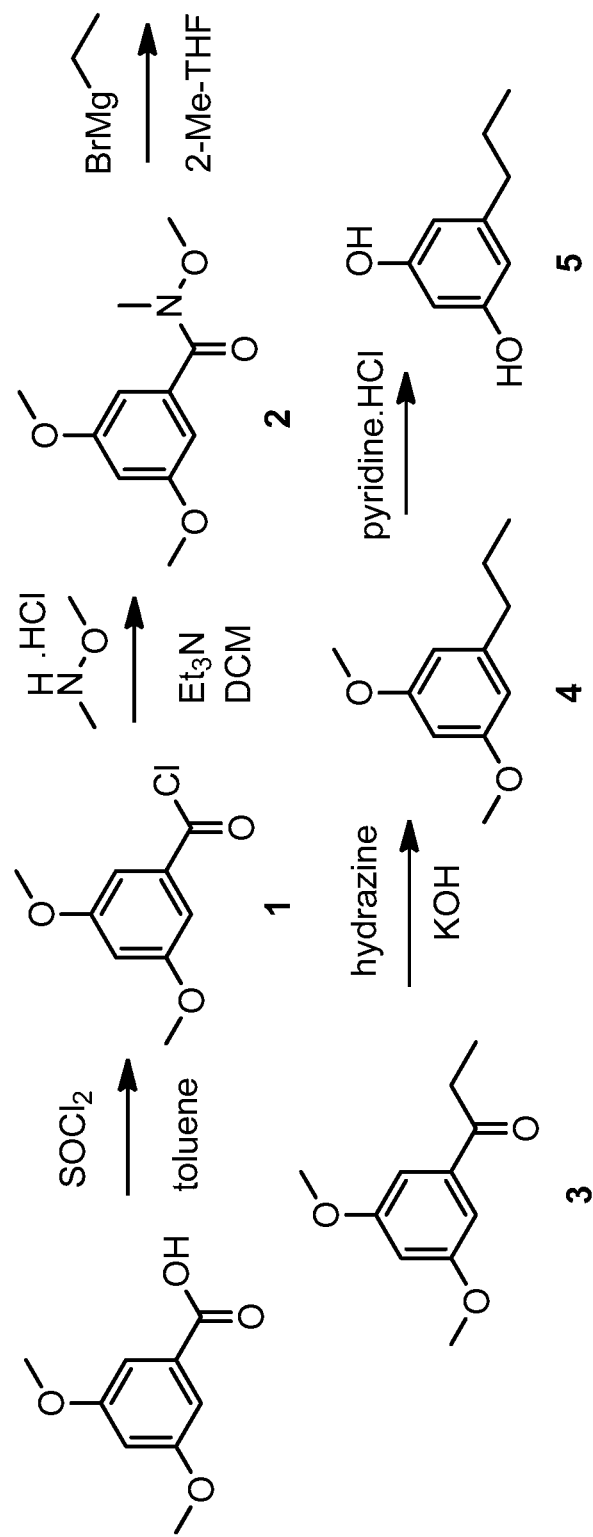
FIG. 4 shows an exemplary synthesis of a $C_3$-olivetol analogue starting from 3,5-dimethoxybenzoic acid.

Synthesis of C3-Olivetol Analogue:

The C3-analog of olivetol was synthesized, starting from commercially available 3,5-dimethoxybenzoic acid as shown in FIG. 4. The synthesis of 3,5-dimethoxybenzoyl chloride [1] was first tested on a 1 g scale by the treatment of 3,5-dimethoxybenzoic acid with 1.2 eq. of $SOCl_2$ in toluene at 100° C. The reaction proceeded smoothly and after 1 hour, a complete conversion was observed on LC-MS. The solvents were evaporated and the product was stripped twice with toluene to remove the excess $SOCl_2$ to yield 1.15 g of [1] (quantitative yield), which was used as such in further experiments. Repetition of the reaction on 95 g scale was performed and yielded a second batch of [1] (110 g, quantitative yield).

Synthesis of 3,5-dimethoxybenzoyl chloride [1]

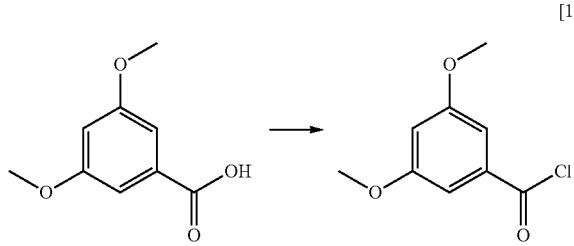

To a suspension of 3,5-dimethoxybenzoic acid (95 g, 521 mmol) in toluene (dry, 950 mL) was added thionyl chloride (74.4 g, 626 mmol, 45.4 ml) and a catalytic amount of DMF (0.2 mL). The mixture was heated to 100° C. and stirred for 6 hours. A clear solution was formed. The mixture was allowed to cool to room temperature and all volatiles evaporated in vacuo using a rotary evaporator. The mixture was stripped twice with fresh toluene (2×100 mL). Yield: 110 g of a brown oil (105% yield).

The preparation of N,3,5-trimethoxy-N-methylbenzamide [2] was first investigated on a 1.10 g scale. To a stirred mixture of [1] (1.10 g) and N,O-dimethyl-hydroxylamine HCl in DCM was added triethylamine (3 eq.) at 0° C. The mixture was allowed to warm to room temperature and stirred over the weekend. Analysis with LC-MS showed complete and clean formation of [2]. Aqueous work-up yielded 0.95 g of a brown oil and subsequent analysis with $^1$H-NMR confirmed the structure. Repetition on 110 g scale was performed and yielded a second batch of [2] (123 g, quantitative yield).

Synthesis of N,3,5-trimethoxy-N-methylbenzamide [2]

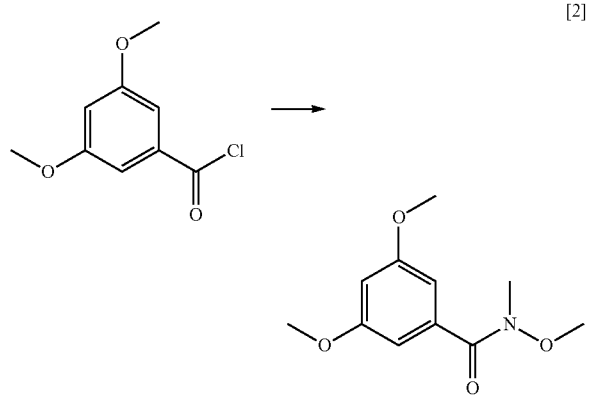

To a cold (0° C.) mixture of 3,5-dimethoxybenzoyl chloride (105 g, 523 mmol) and N,O-dimethylhydroxylamine hydrochloride (61.3 g, 628 mmol) in dichloromethane (1000 mL) was slowly added triethylamine (159 g, 1570 mmol, 218 mL). During the addition, a thick suspension was formed (triethylamine HCl), which hindered proper stirring. Extra DCM (200 mL) was added and the mixture was stirred overnight. The reaction mixture was washed twice with 50% diluted aqueous brine (2×500 mL) and dried the organic phase on $Na_2SO_4$. Evaporated all volatiles in vacuo using a rotary evaporator. Yield: 122.5 g of a brown oil (104% yield).

With [2] available, the Grignard reaction towards 1-(3,5-dimethoxyphenyl)propan-1-one [3] was investigated on 0.5 g scale. At 0° C., a solution of the [2] in 2-Me-THF was added drop-wise to a solution of ethyl magnesium bromide in 2-Me-THF in 5 minutes. After 3 hours, LC-MS showed the formation of two new main products (at 1.74 and 2.11 min) as well as remaining starting material (at 1.86 min). The peak at 2.11 minutes showed the correct mass for [3] while the peak at 1.74 minutes showed a mass of 196 in positive mode in the mass trace. The mixture was allowed to warm to room temperature and stirred overnight. Subsequent analysis with LC-MS showed no further conversion. Aqueous work-up yielded 1.15 g of a brown oil which was purified by column chromatography.

All components were separated and both of the newly formed products were characterized by LC-MS and $^1$H-NMR. In this manner, a batch of [3] (0.11 g of a colorless oil) was obtained and the structure was confirmed. Of the unknown side product, 0.04 g was isolated as a white solid. Both the observed mass in LC-MS and the $^1$H-NMR spectrum indicated that this compound was an amide. The $^1$H-NMR spectrum and appearance are in agreement with the literature (*J. Am. Chem. Soc.*, 2014, 136, 6920-6928). The formation of this side product can be explained by deprotonation of the methoxy-group of the Weinreb amide by the basic Grignard reagent, leading to demethoxylation.

With all reaction products known, repetition on a 0.36 g scale was performed wherein solution of the [2] in 2-Me-THF was added dropwise to a solution of ethyl magnesium bromide (1.1 eq.) in 2-Me-THF at 0° C. After stirring for 2 hours, LC-MS showed a very similar pattern to the previous experiment with 47 area % [3], 24 area % of the 3,5-dimethoxy-N-methylbenzamide and 27 area % remaining starting material. A second aliquot of ethyl magnesium bromide (1.1 eq.) was added and the mixture was allowed to warm to room temperature overnight. Subsequent analysis with LC-MS showed a complete consumption of [2] and the formation of a 1:1 mixture of [3] and 3,5-dimethoxy-N-methylbenzamide. Unfortunately, the initial selectivity towards [3] observed in the earlier sample was no longer found.

The Grignard reaction towards [3] was continued without further optimization and to remove the formed amide side product by column chromatography. Thus, on 120 g scale, [2] was treated with ethyl magnesium bromide at 0° C. No problems were encountered and [3] was formed as expected in a 59:36 ratio with the 3,5-dimethoxy-N-methylbenzamide. Aqueous work-up yielded 97 g of a brown oil which was purified by column chromatography using silica and heptane:ethyl acetate (4:1) as eluent to yield 47 g of [3] as a colourless oil in 45% yield. The oil crystallized upon standing and analysis with LC-MS showed that the purity was 97%.

Synthesis of 1-(3,5-dimethoxyphenyl)propan-1-one [3]

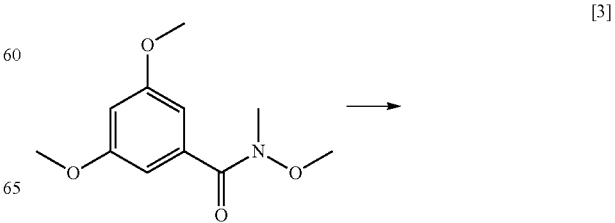

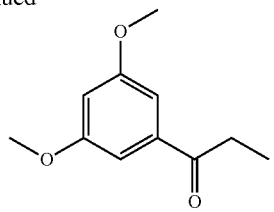

To a cold (0° C.) solution of N,3,5-trimethoxy-N-methylbenzamide (120 g, 533 mmol) in 2-Me-THF (1000 mL) was slowly added ca. 3.2 M solution of ethylmagnesium bromide in 2-Me-THF (608 mmol, 190 mL) in 4 hours. After stirring for an additional 30 minutes, LC-MS showed partial conversion. Slowly ca. 3.2 M solution of ethylmagnesium bromide (64.0 mmol, 20 mL) was added. The mixture was stirred for another 30 minutes, then allowed to slowly warm to room temperature and stirred overnight. The reaction mixture was poured into 1M aq. HCl (800 mL). The layers were separated and the aqueous phase was extracted with ethyl acetate (250 mL). The combined organic layers were washed with brine (250 mL), then dried on $Na_2SO_4$. All volatiles were evaporated in vacuo using a rotary evaporator. Un-purified Product yield: 97 g of a brownish oil containing a white solid. The isolated product was purified by gravity column chromatography (silica; eluent: heptane/ethyl acetate=4:1). Yield: 47 g of a colorless oil (45% yield). The oil crystallized spontaneously upon standing for 2 days. LC-MS: purity 98%, [M+H]=195.

With this material available, a Wolf-Kishner reduction towards 1,3-dimethoxy-5-propylbenzene [4] was performed on 0.5 g scale. [3] was treated with 2 equivalents of hydrazine in refluxing ethanol as described for this compound in *J. Med. Chem.*, 1991, 34 (11), p 3310-3316. After 5 hours, a nearly complete conversion into the desired imine intermediate was observed with LC-MS. All volatiles were evaporated using a rotary evaporator and the resulting oil was heated to 230° C. in the presence of KOH (7.5 eq.) in the melt. After heating for 1 hour, the mixture was cooled to room temperature overnight. Upon cooling, a white solid (KOH) with a slightly yellow oil on top was formed. A sample of the oil was analysed with LC-MS which showed a complete conversion and exclusive formation of [4].

The oil was separated from the solids by decanting. The oil was dissolved in ethyl acetate and washed with 1M aq. HCl. After drying over $Na_2SO_4$ and evaporation of the solvents, a yellow oil was obtained (0.23 g, 49%). Analysis with ¹H-NMR confirmed the structure. Repetition of the reaction on 46 g scale was performed and a complete conversion was achieved. After aqueous work-up, [4] was obtained as a yellow oil in moderate yield (21.1 g, 49%) and acceptable purity (93% according to LC-MS) without any additional purification.

Summary of 1,3-dimethoxy-5-propylbenzene [4]

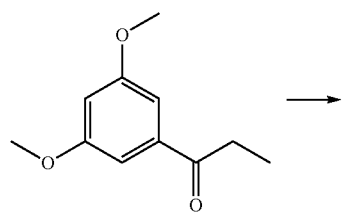

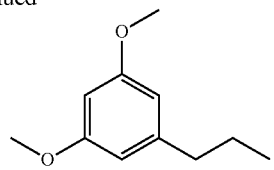

A mixture of 1-(3,5-dimethoxyphenyl)propan-1-one (46 g, 237 mmol) and hydrazine monohydrate (23.71 g, 474 mmol, 23.07 ml) in ethanol (2.5 ml) was heated to reflux and stirred for 6 hours. All volatiles were in vacuo using a rotary evaporator to yield a yellow oil. Potassium hydroxide (100 g, 1776 mmol) was added and heated the resulting mixture to 230° C. for 30 minutes. The mixture was allowed to cool to room temperature, dissolved in water (250 mL) and then extracted three times with diethyl ether (3×100 mL). The combined organic layers were dried on $Na_2SO_4$ and all volatiles were evaporated in vacuo using a rotary evaporator. Yield: 21.1 g of a yellow oil (49% yield). LC-MS: purity 93%, [M+H]=181. ¹H-NMR δ (CDCl₃): 6.35 (d, J=2.2 Hz, 2H), 6.30 (t, J=2.2 Hz, 1H), 3.78 (s, 6H), 2.53 (t, J=7.5 Hz, 2H), 1.63 (sextet, J=7.4 Hz, 2H), 0.94 (t, J=7.3 Hz, 3H).

With [4] available, a 0.5 g scale test reaction for the bis-demethylation (based on *Molecules*, 2014, 19, 13526-13540) was performed by heating [4] in a melt at 200° C. with pyridine HCl for 3 hours. A complete conversion was observed on LC-MS and the desired mass was found in the MS trace. After aqueous work-up, 5-propylbenzene-1,3-diol [5] was isolated as a yellow oil in moderate yield (0.25 g, 59%) but in good purity (94% according to LC-MS) without any additional purification. Repetition on 21 g scale was performed, but the reaction could not be driven to completion, with 11% of [4] remaining after prolonged heating. After aqueous work-up, [5] (16.5 g) was obtained with a purity of only 73% (according to LC-MS). Purification using an automated Releris® chromatography system (120 g silica cartridge, heptane:ethyl acetate as eluent) yielded [5] as a yellow oil in moderate yield (11.6 g, 65%) but high purity (96% according to LC-MS). The oil spontaneously crystallized upon standing. The structure of the [5], the C3-olivetol analogue, was confirmed by ¹H-NMR. The preparation of a [5], the C3-olivetol analogue, starting from commercially available 3,5-dimethoxybenzoic acid, was performed successfully.

Synthesis of 5-propylbenzene-1,3-diol [5]

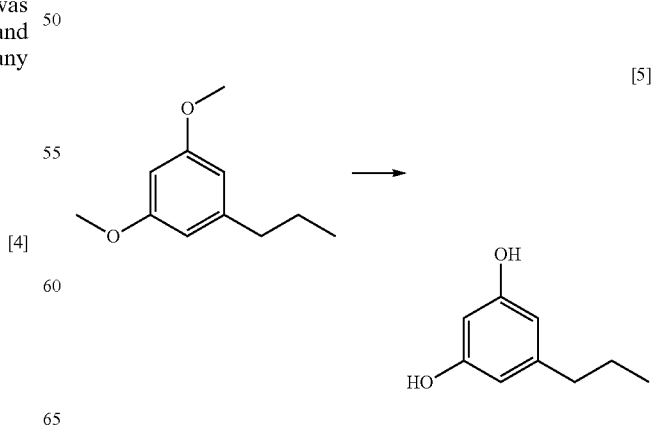

A mixture of 1,3-dimethoxy-5-propylbenzene (21 g, 117 mmol) and pyridine hydrochloride (67.3 g, 583 mmol) was heated to 200° C. for 4 hours, then allowed to cool to room temperature overnight. Water (100 mL) was added and the mixture was extracted three times with diethyl ether (3×100 mL). The combined organic phase was dried on $Na_2SO_4$ and all volatiles evaporated in vacuo using a rotary evaporator. Un-purified Product yield: 16.5 g brown oil. The brown oil was purified by column chromatography (120 g silica; eluent: heptane/ethyl acetate; gradient: t=0 min. 20% ethyl acetate, t=35 min. 50% ethyl acetate). Yield: 11.6 g of a yellow oil (65% yield). The oil slowly crystallized upon standing. LC-MS: purity 96%, [M+H]=153. $^1$H-NMR δ (CDCl$_3$): 6.25 (d, J=2.2 Hz, 2H), 6.18 (t, J=2.2 Hz, 1H), 5.44 (broad s, 2H), 2.45 (t, J=7.4 Hz, 2H), 1.58 (sextet, J=7.4 Hz, 2H), 0.91 (t, J=7.3 Hz, 3H).

Example 3—Generality of Di-Halo Protection of Olivetol

The use of bromide, chloride and iodide was investigated as providing di-halo protection to 5-propylbenzene-1,3-diol [5], the C3-olivetol analogue.

Figure 5:
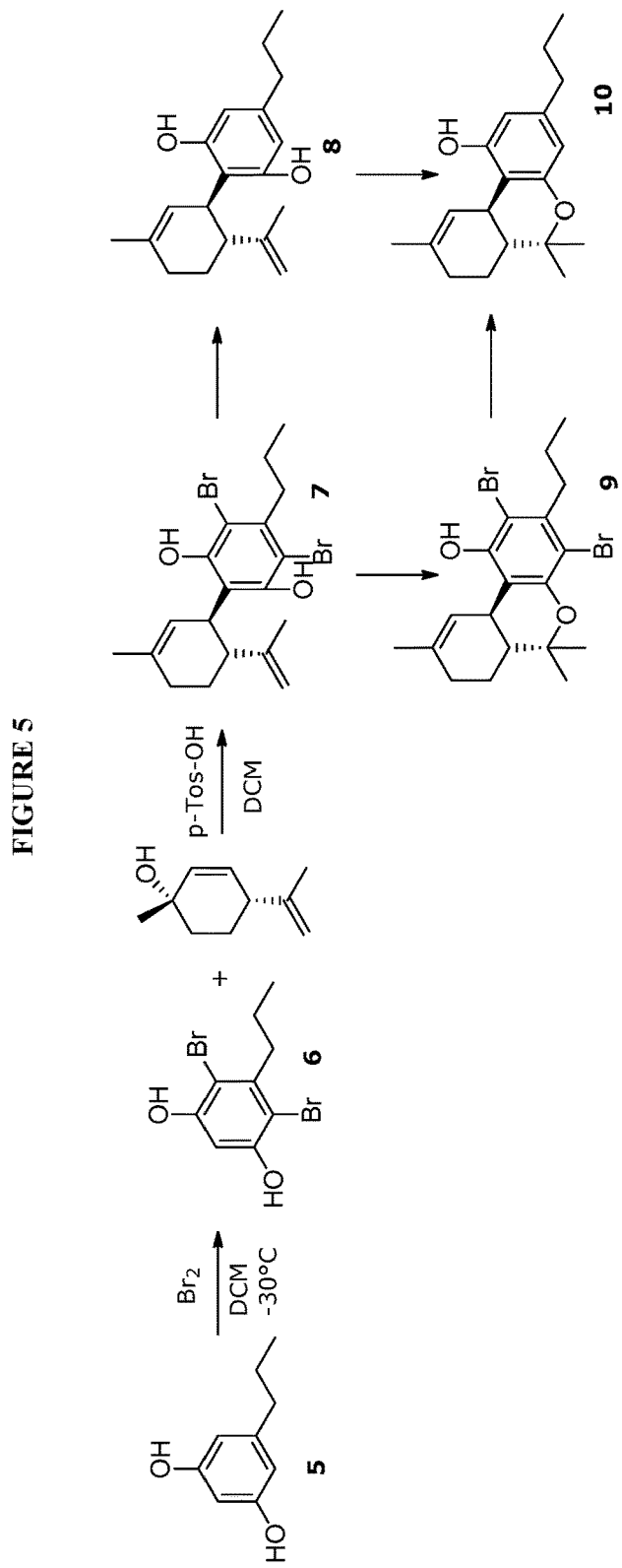
FIG. 5 shows exemplary synthetic pathways for the C3-cannabidiol and C3-tetrahydrocannabinol analogues using bromide protective groups.

Adding Bromide as Protection Group:

The bromination of [5] towards 4,6-dibromo-5-propyl-benzene-1,3-diol [6] was performed as shown in FIG. 5. At −30° C., a solution of 0.25 g of [5] in 6 ml DCM was treated with 2.0 eq. of bromine. During cooling of the initial starting material solution, a sticky oil had formed at the bottom of the flask which hindered proper stirring. Also, the bromine was added using a syringe. The low temperature inside the reaction flask caused the bromine to solidify in the needle and blocked it. In a subsequent experiment, a bigger stirring magnet was used and the bromine was added as a solution in DCM using a dropping funnel in 10 minutes. After stirring for an additional 10 minutes, the reaction mixture was poured into a cold aqueous sodium thiosulfate solution. A cloudy DCM layer was formed. Addition of ethyl acetate did not remove the cloudiness. Addition of diethyl ether resulted in two clear layers. The layers were separated, the aqueous phase extracted once with diethyl ether. After evaporation of the solvents, [6] was obtained as an off white solid in moderate yield (0.40 g, 79%) but in good purity (94%, according to LC-MS). The mass of the [6] was also found in the mass trace with no mono- or tri-bromo compound detected. The structure was confirmed by $^1$H-NMR and further analysis with HMBC-NMR only showed interactions between the aromatic proton and aromatic carbons and not between any aliphatic carbons, thereby confirming the structure.

Repetition of the bromination on 1 g scale was performed using a mechanical top stirrer. After work-up, a second amount of [6] was obtained in moderate yield (1.67 g, 82%) and analysis by LC-MS showed that the purity was 93%. Repetition on 10 g scale gave complete conversion but two impurities were observed in the LC-MS chromatogram in larger amounts than in earlier experiments. Nevertheless, this material was used as such in the subsequent coupling with menthadienol towards compound [7].

Synthesis of 4,6-dibromo-5-propylbenzene-1,3-diol [6]

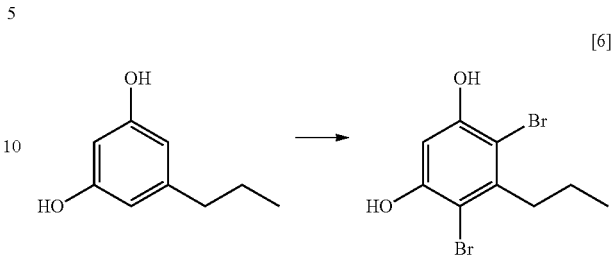

A solution of 5-propylbenzene-1,3-diol (1 g, 6.57 mmol) in dichloromethane (20 ml) was cooled to −50° C. Initially, a suspension was formed but upon further cooling, the starting material precipitated as a sticky oil. Additional DCM (~5 mL) was added to allow for proper stirring. Then, a solution of bromine (2.111 g, 1.32 mmol, 0.679 ml) in dichloromethane (20 ml) was added drop wise in 15 minutes using a dosing funnel and the resulting mixture was stirred for 15 minutes. The temperature was kept below −50° C. during the reaction and subsequent stirring. The reaction mixture was poured into a cold (0° C.) solution of sodium thiosulfate (0.519 g, 3.29 mmol) in water (20 ml) and stirred vigorously until any bromine color had disappeared. During stirring, a suspension was formed in the DCM phase. The biphasic system was extracted with diethyl ether (50 mL) and the layers were separated. The aqueous phase was extracted once more with diethyl ether (50 mL) and the combined organic layers were dried on $Na_2SO_4$ and all volatiles were evaporated in vacuo using a rotary evaporator. Yield: 1.67 g off-white solids (82% yield). LC-MS: purity 96%, [M+H]=309. $^1$H-NMR δ (400 MHz, CDCl$_3$): 10.20 (s, 2H), 6.57 (s, 1H), 3.36 (s, 1H), 2.93-2.78 (m, 2H), 2.56-2.44 (m, 2H), 1.57-1.41 (m, 2H), 0.97 (t, J=7.3 Hz, 3H).

The coupling with menthadienol towards (1'R,2'R)-3,5-dibromo-5'-methyl-2'-(prop-1-en-2-yl)-4-propyl-1',2',3',4'-tetrahydro-[1,1'-biphenyl]-2,6-diol [7] was first tested on a 1.6 g scale, prior to the 10 g scale reaction. [6] was treated with menthadienol (1.0 eq.) at −30° C. in the presence of MgSO$_4$ and p-toluenesulfonic acid in DCM. Conversion into a new product with the correct mass was observed with LC-MS and by the addition of extra menthadienol in two portions (0.25 and 0.125 equivalents respectively), the reaction was driven to completion. After subsequent aqueous work-up and stirring in methanol to precipitate side products, [7] was isolated as a yellow oil in quantitative yield (2.36 g, 99%). LC-MS indicated that the purity was 93% and the structure was confirmed with $^1$H-NMR.

Repetition of the coupling with menthadienol on 10 g scale was performed. The formation of an unknown side product was found in the final stage of the reaction. After aqueous work-up and subsequent precipitation of side products in methanol, the isolated product (22.7 g, 90%) had a purity of only 63% according to LC-MS. The unknown side product was investigated was an intermediate that is formed as the reaction proceeds via a rearrangement mechanism. Treatment with p-toluenesulfonic acid was performed to facilitate the quantitative conversion of this intermediate towards [7]. A 100 mg sample of the batch was dissolved in DCM and treated with 0.25 equivalents of p-toluenesulfonic acid at 0° C. After stirring for 4 hours, no conversion was observed with LC-MS. The mixture was allowed to slowly warm to room temperature and stirred overnight. LC-MS showed no conversion. The experiment was stopped and the mixture was discarded.

To purify the material further, column chromatography over silica and with heptane/ethyl acetate as eluent was attempted. No separation was achieved and only baseline material was removed in this manner. All product containing fractions were collected again and concentrated to yield 17 g of a dark yellow oil.

A sample (0.5 g) was subjected to reversed phase column chromatography (40 g, C18 silica) using a Reveleris® system and MeCN/water (with 0.1% formic acid) as eluent. Sufficient separation of the two main components was achieved and the product containing fractions were collected and all volatiles evaporated to yield 0.15 g of [7] as a yellow oil. Subsequent analysis showed that the purity was 99%. The fractions containing the unknown side product were also combined and concentrated but during this operation, the material decomposed.

The entire batch of material was purified using reversed phase column chromatography in 1.5 g portions using a 120 g C18 silica column and MeCN/water (with 0.1% formic acid) as eluent. In this manner, 7.7 g (30%) of [7] was obtained as a yellow oil with a purity of 99% according to LC-MS.

The fractions containing the unknown side product were combined and then lyophilized to remove the solvents and to avoid decomposition. 2.14 g of an off-white solid was obtained. Subsequent analysis with LC-MS showed that this compound was 92% with about 7% of [7] as the main impurity. No mass was observed in the mass trace. Further analysis with $^1$H-NMR was inconclusive It is believed that this molecule is comprised of 1 molecule of the dibromo-n-propylresorcinol and 2 molecules of the menthadienol. After being exposed to air (after lyophylization), the solid turned dark purple within 1 hour.

Synthesis of (1'R,2'R)-3,5-dibromo-5'-methyl-2'-(prop-1-en-2-yl)-4-propyl-1',2',3',4'-tetrahydro-[1,1'-biphenyl]-2,6-diol [7]

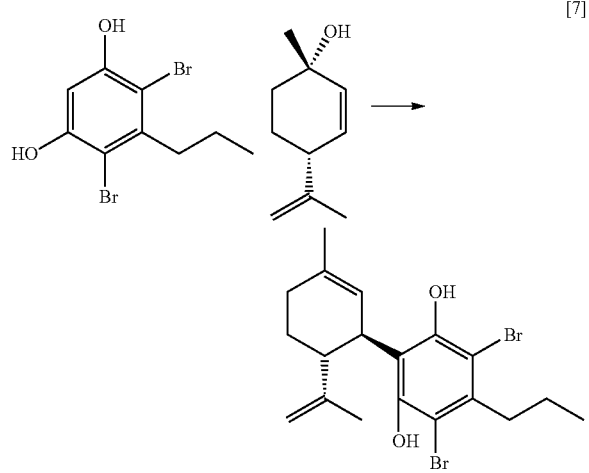

A mixture of 4,6-dibromo-5-propylbenzene-1,3-diol (1.67 g, 5.39 mmol), (1R,4R)-1-methyl-4-(prop-1-en-2-yl)cyclohex-2-enol (0.820 g, 5.39 mmol) and magnesium sulfate (1.621 g, 13.47 mmol) in dichloromethane (18 mL) was cooled to −35° C. Then, p-toluenesulfonic acid monohydrate (0.512 g, 2.69 mmol) was added in one portion and the resulting mixture was stirred at −35° C. The reaction was monitored with LC-MS and over the course of 5 hours, extra aliquots of (1R,4R)-1-methyl-4-(prop-1-en-2-yl)cyclohex-2-enol (0.205 g, 1.347 mmol and 0.103 g, 0.673 mmol respectively) were added before allowing the mixture to slowly warm to room temperature overnight. The reaction mixture was poured into a solution of dibasic potassium phosphate (0.845 g, 4.85 mmol) in water (18 mL) and the layers were separated. The aqueous phase was extracted with DCM (18 mL) and the combined organic layers were passed through a phase separator. Then, all volatiles were evaporated in vacuo using a rotary evaporator. Un-purified yield: 2.951 g of a yellow oil. The obtained oil was dissolved in methanol (10 mL) and then stirred for 1 hour at 0° C. The white solid was removed by filtration using a folded paper filter and was discarded. The clear filtrate was evaporated to dryness (in vacuo) using a rotary evaporator. Yield: 2.36 g yellow oil (99% yield). LC-MS: purity 93%, mass not detected due to poor ionization of the compound. $^1$H-NMR δ (400 MHz, DMSO-$d_6$): 8.87-8.21 (m, 2H), 5.15 (s, 1H), 4.45 (d, J=8.7 Hz, 2H), 4.03 (d, J=8.9 Hz, 1H), 3.05-2.93 (m, 1H), 2.88-2.76 (m, 2H), 2.29-2.16 (m, 1H), 2.12-2.08 (m, 1H), 1.99-1.95 (m, 1H), 1.77-1.55 (m, 6H), 1.55-1.42 (m, 3H), 0.96 (t, J=7.3 Hz, 3H).

Debromination of [7] towards (1'R,2'R)-5'-methyl-2'-(prop-1-en-2-yl)-4-propyl-1',2',3',4'-tetrahydro-[1,1'-biphenyl]-2,6-diol [8], or the desired C3-cannabidiol derivative, was performed on 0.5 g scale. A mixture of [7], L-ascorbic acid (0.15 eq.), sodium sulfite (2.65 eq) and triethylamine in methanol/water was heated to 75° C. for 18 hours. Analysis with LC-MS showed complete conversion but also showed the formation of several side products. After aqueous work-up, a brown oil was obtained in good yield (307 mg, 95%) but the purity was only 73%, according to LC-MS. The oil was purified by column chromatography using a Reveleris® system to yield a purified fraction (72 mg, 22%) as a light yellow brown oil. Analysis of this material with LC-MS indicated the purity was 96% and the structure was confirmed by analysis with $^1$H-NMR.

Repetition on 1.8 g scale initially yielded 0.46 g product (39%) as a yellow oil that spontaneously partially solidified. Analysis with LC-MS showed that the purity was 84%. Further investigations to the work-up procedure showed that a lot of product remained in the aqueous phase, which was therefore extracted with DCM instead of heptane. This treatment furnished a second amount of material (0.56 g, 48%) as a yellow oil, bringing the total yield up to 87%.

Both amounts of [8] were combined and attempts were made to crystallize the product from heptane, heptane/DCM, heptane/DIPE and methanol/water mixtures. None of the crystallizations worked. All material was collected again and purified by column chromatography using a Reveleris® system to yield 0.58 g (50%) of [8] as a light brown oil, which solidified spontaneously upon standing. Analysis with LC-MS confirmed the mass and showed the purity to be 97%. The structure was confirmed by $^1$H-NMR. Broad signals in the aromatic region were observed likely a result of hindered rotation around the benzylic C—C bond.

Repetition of the debromination on 7 g scale was carried out at 40° C. for 2 hours and the mixture was then analyzed with LC-MS. The partial removal of only 1 bromide group was observed at this stage. The temperature was increased to 75° C. for 1 hour, which resulted in a nearly complete conversion of the starting material and the formation of the mono-debrominated compound. The mixture was then stirred at 75° C. for a longer period and was monitored over time. After 16 hours, an almost complete debromination was achieved. The removal of the second bromine group was more difficult than the first group, but a full conversion was achieved.

Aqueous work-up and extraction with DCM yielded 5.1 g of product as a yellow oil that spontaneously partially solidified. This material was purified by column chromatography to yield [8] (3.5 g, 78%) as a slightly yellow oil that spontaneously solidified. Analysis with LC-MS showed the purity to be 99% and the correct mass was observed in the mass trace. Further analysis with ¹H-NMR confirmed the structure and showed the presence of 6 w/w % heptane. The analytical data of the prepared compound matched with the data obtained from a commercial reference sample.

Synthesis of (1'R,2'R)-5'-methyl-2'-(prop-1-en-2-yl)-4-propyl-1',2',3',4'-tetrahydro-[1,1'-biphenyl]-2,6-diol [8]

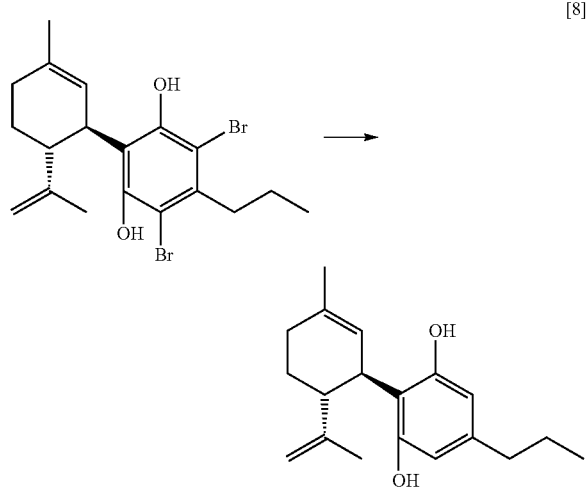

To a solution of (1'R,2'R)-3,5-dibromo-5'-methyl-2'-(prop-1-en-2-yl)-4-propyl-1',2',3',4'-tetrahydro-[1,1'-biphenyl]-2,6-diol (1.8 g, 4.05 mmol) in methanol (15 ml) was added a solution of sodium sulfite (1.353 g, 10.74 mmol) and L-ascorbic acid (0.107 g, 0.608 mmol) in water (15 mL). A suspension was formed that later formed a sticky oil that hindered proper stirring. To the suspension, triethylamine (1.476 g, 14.59 mmol, 2.028 ml) was added in one portion which caused the sticky oil to dissolve just enough to allow proper stirring. The resulting mixture was heated to 75° C. for 18 hours. After cooling to room temperature, the reaction mixture was partially concentrated in vacuo, using a rotary evaporator, to remove most of the methanol and volatiles. The pH of the remaining aqueous phase was adjusted to ~2 with concentrated hydrochloric acid. Heptane (25 mL) was added and the mixture was stirred for 30 minutes. The layers were separated, the organic phase was washed with brine (25 mL) and then evaporated in vacuo using a rotary evaporator. Un-purified yield: 0.46 g yellow oil. The oil partially solidified spontaneously. The remaining aqueous phase stirred with DCM (25 mL) for 30 minutes. The layers were separated, the organic phase was washed with brine (25 mL) and then evaporated in vacuo using a rotary evaporator. Un-purified yield: 0.56 g yellow oil. The oil partially solidified spontaneously. Both oils were combined and purified by column chromatography (silica, eluent: heptane/ethyl acetate). Yield: 0.58 g of a light brown oil (50% yield). The oil solidified upon standing. LC-MS: purity 97%, [M+H]=287. ¹H-NMR δ (400 MHz, CDCl₃): 6.27 (s, 1H), 6.17 (s, 1H), 5.98 (s, 1H), 5.57 (s, 1H), 4.70-4.50 (m, 3H), 3.82-3.86 (m, 1H), 2.47-2.34 (m, 3H), 1.87-1.72 (m, 5H), 1.70-1.63 (m, 4H), 1.62-1.52 (m, 3H), 0.90 (t, J=7.3 Hz, 3H).

The ring-closures of both [7] and [8] towards the C3-THC analogues [9] and [10], shown in FIG. 5, was performed. Both ring-closures were screened on 50 mg scale using both [7] and [8] as the substrate. Table 1 list the results of the screening as monitored with LC-MS.

TABLE 1

Overview of ring-closure reactions.

| # | Substrate | Conditions | Result |
|---|---|---|---|
| 1 | 7 | 1 eq. p-TosOH, DCM, rt, 18 h. | 17% of a new product with correct mass |
| 2 | 7 | 1 eq. p-TosOH, toluene, 100° C., 18 h | decomposition |
| 3 | 7 | 1.2 eq. BF₃ etherate, DCM, −10° C., 2 h. | near complete conversion into new product with correct mass, some decomposition |
| 4 | 8 | 1 eq. p-TosOH, toluene, 100° C., 18 h | decomposition |
| 5 | 8 | 1.2 eq. BF₃ OEt₂, DCM, −10° C., 2 h. | near complete conversion into new product with correct mass, no decomposition |

From these results, it was found that the use of p-toluenesulfonic acid in toluene at elevated temperature did not induce an effective ring-closure reaction. At a lower temperature, however, the use of p-toluenesulfonic acid did lead to the formation of a new product with the correct mass but only in 17% estimated yield. Using BF₃ etherate a complete conversion was achieved with both substrates. These reaction mixtures, e.g., 3 and 5, were subjected to an aqueous work-up and the products were isolated. In this manner, 28 mg (56% yield) and 39 mg (78% yield) of [9] and [10] respectively were obtained as yellowish oils.

Analysis with LC-MS showed the correct masses of [9] and [10], and purities of 90 and 97%, respectively. The oils were stored overnight at room temperature. In the case of experiment 3 for [9], the oil had turned dark brown/purple and analysis with LC-MS showed that the material had decomposed. In the case of experiment 5 for [10], the oil had partly solidified. Analysis with ¹H-NMR showed that the correct compound was formed but some impurities, that were not observed with LC-MS, still remained.

Experiment 5 for [10] was repeated on 1.3 g scale. After 90 minutes of reaction time (at −10° C.), a clean and near complete conversion was achieved. Aqueous work-up and extraction yielded the product as a yellow/brownish oil (1.43 g, 102% yield) with a purity of 96% according to LC-MS. The product was purified by Reveleris® column chromatography (using silica and heptane/ethyl acetate as eluent) to yield a slightly yellow oil (1.33 g, 95% yield). Analysis with LC-MS showed one main signal in 97% with the correct mass and the other peak originating from unreacted [8]. Analysis with ¹H-NMR showed several unexpected signals that indicate that a closely related compound was present in the obtained material, as well as some residual ethyl acetate. Further analysis with analytical HPLC revealed that a second product (22%) was present with a minute difference in retention time, again indicating that the impurity is closely related to the product.

It is known that Δ9-THC is capable of acid-catalyzed isomerization to the thermodynamically more stable Δ8-THC regio-isomer. The separation of Δ8- and Δ9-THC is also known to be challenging, requiring multiple chromatographic steps. It is believed that the unknown impurity is the Δ8-isomer of [10]. Despite the presence of the impurity, the formation of [10] via the sequence [7]-[8]-[10] was demonstrated.

Synthesis of (6aS,10aR)-6,6,9-trimethyl-3-propyl-6a,7,8,10a-tetrahydro-6H-benzo[c]chromen-1-ol [7]-[8]-[10]

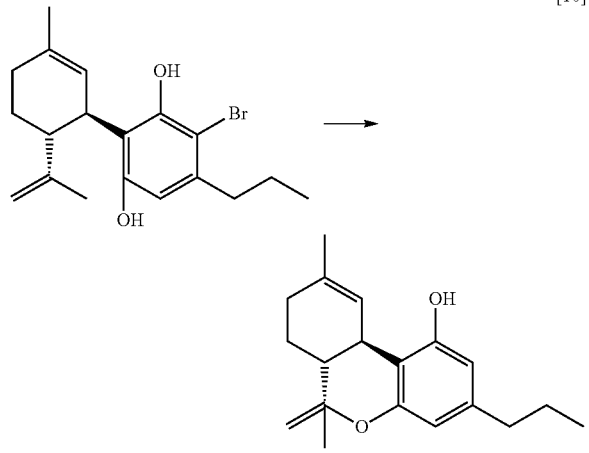

To a cold (−10° C.) solution of boron trifluoride etherate (ca. 48% $BF_3$, 0.833 g, 5.87 mmol, 0.743 mL) in dichloromethane (20 ml) was slowly added a solution of (1'R,2'R)-5'-methyl-2'-(prop-1-en-2-yl)-4-propyl-1',2',3',4'-tetrahydro-[1,1'-biphenyl]-2,6-diol (1.4 g, 4.89 mmol) in dichloromethane (10 ml) in 15 minutes. After stirring for 90 minutes, the reaction mixture was quenched by addition of water (20 mL). The formed slurry was diluted with extra DCM (25 mL) and the layers were separated. The aqueous phase was extracted once with fresh DCM (25 mL) and the combined organic layers were dried on $Na_2SO_4$ and all volatiles evaporated in vacuo using a rotary evaporator. Un-purified yield: 1.42 g yellow/brownish oil. The oil was purified by column chromatography (80 g silica; eluent: DCM (A)/10% methanol in DCM (B); gradient: t=0 min. 0% B, t=5 min. 5% B, t=20 min. 20% B). Yield: 1.33 g slightly yellow oil (95% yield). LC-MS: purity 97%, [M+H]=287. $^1$H-NMR δ (400 MHz, $CDCl_3$): 6.34-6.23 (m, 2H), 6.17-6.05 (m, 1H), 5.30 (s, 1H), 4.79 (s, 1H), 3.20 (d, J=10.9 Hz, 1H), 2.50-2.37 (m, 2H), 2.23-2.12 (m, 2H), 1.96-1.87 (m, 2H), 1.77-1.64 (m, 4H), 1.64-1.49 (m, 2H), 1.45-1.36 (m, 3H), 1.09 (s, 2H), 0.91 (t, J=7.3 Hz, 3H).

The ring-closure via compound [9] followed by removal of the two bromides to form compound [10] was performed. To avoid the observed stability issues, compound [9] was not isolated but used directly as a solution in DCM. A solution of compound [7] (200 mg) in DCM was treated with 1.2 equivalents of $BF_3$ etherate at −10° C. LC-MS showed the formation of a new product (the mass of compounds [7] and [9] are the same and thus gives no additional information about the conversion at this point). After a total reaction time of 45 minutes, the mixture was quenched with water and the layers were separated. The organic phase was used as such in the debromination-reaction.

After the addition of methanol, an aqueous solution of $Na_2SO_3$ (2.65 eq.) and L-ascorbic acid (0.15 eq.) was added, followed by triethylamine (3.6 eq.). The mixture was heated to 40° C. and the conversion was monitored by LC-MS. After 2 hours at this temperature, no conversion was observed. The temperature was increased to 75° C. and the mixture was stirred for 1 hour. Again, no significant conversion was detected. Stirring was continued overnight and subsequent analysis with LC-MS showed the formation of a new product with the correct retention time and mass of [10]. After aqueous work-up, 85 mg of a yellow oil was obtained (65% yield over two steps, not corrected for the purity) with a purity of 78%. The formation of [10] via the sequence [7]-[9]-[10] was demonstrated.

Synthesis of (6aS,10aR)-6,6,9-trimethyl-3-propyl-6a,7,8,10a-tetrahydro-6H-benzo[c]chromen-1-ol [10]

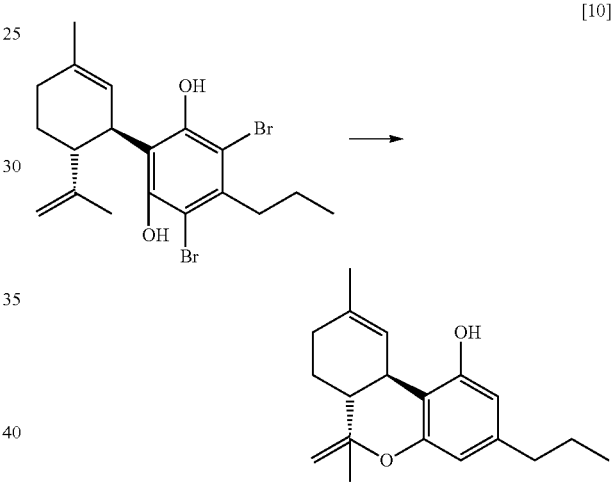

To a cold (−10° C.) solution of boron trifluoride etherate (ca. 48% $BF_3$, 77 mg, 0.540 mmol, 0.068 ml) in dichloromethane (2 mL) was slowly added a solution of (1'R,2'R)-3,5-dibromo-5'-methyl-2'-(prop-1-en-2-yl)-4-propyl-1',2',3',4'-tetrahydro-[1,1'-biphenyl]-2,6-diol (200 mg, 0.450 mmol) in dichloromethane (2 ml) in 15 minutes. After stirring for 60 minutes, the reaction was quenched by addition of water (2 mL). The formed slurry was diluted with extra DCM (2 mL) and the layers were separated using a phase separator. To the organic phase was added methanol (2 mL) and a solution of sodium sulfite (150 mg, 1.193 mmol) and L-ascorbic acid (11.89 mg, 0.068 mmol) in water (2 mL). At room temperature, added triethylamine (164 mg, 1.621 mmol, 0.225 ml) in one portion, heated the mixture to 75° C. and stirred overnight. After cooling to room temperature, the reaction mixture was partially concentrated in vacuo, using a rotary evaporator, to remove most of the methanol and volatiles. The pH of the remaining aqueous phase was adjusted to ~4 with 3M aq. hydrochloric acid. DCM (5 mL) was added and the mixture was stirred for 30 minutes. The layers were separated and remaining aqueous phase was extracted with DCM (5 mL). The layers were separated and the combined organic phases were dried with a phase separator. All volatiles were evaporated in vacuo using a rotary evaporator. Yield: 85 mg yellow oil (66% yield). LC-MS: purity 78%, [M+H]=287. $^{1}$H-NMR δ (400 MHz, CDCl$_3$): 6.34-6.23 (m, 2H), 6.17-6.05 (m, 1H), 5.30 (s, 1H), 4.79 (s, 1H), 3.20 (d, J=10.9 Hz, 1H), 2.50-2.37 (m, 2H), 2.23-2.12 (m, 2H), 1.96-1.87 (m, 2H), 1.77-1.64 (m, 4H), 1.64-1.49 (m, 2H), 1.45-1.36 (m, 3H), 1.09 (s, 2H), 0.91 (t, J=7.3 Hz, 3H).

Figure 6:
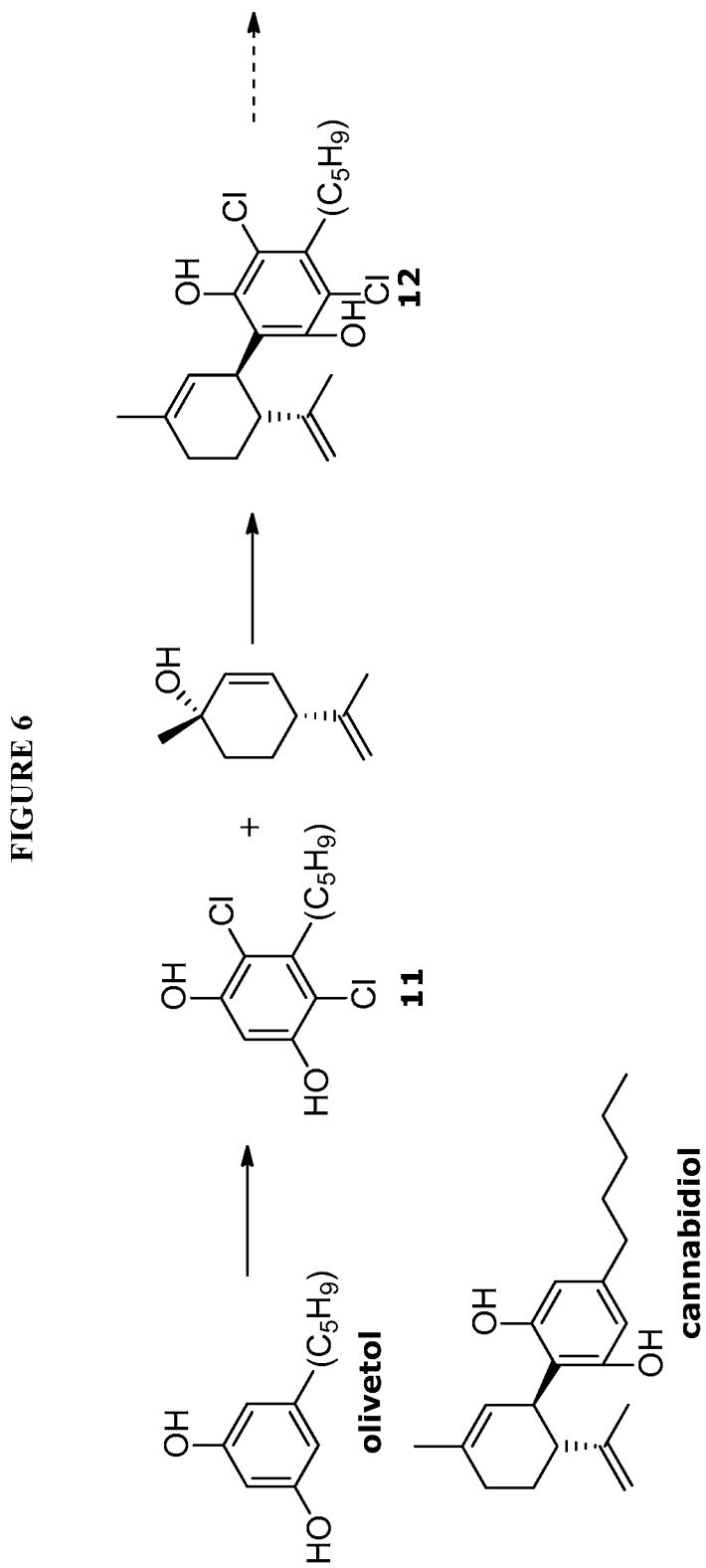
FIG. 6 shows an exemplary synthetic pathway for cannabidiol using chloride protective groups.

Adding Chloride as Protection Group:

The chlorination of olivetol towards cannabidiol was performed as shown in FIG. 6. A solution of olivetol (1 g) in DCM was treated with 2 equivalents of sulfuryl chloride using a dropping funnel at 0° C. After 1 hour, a new product with the correct mass was formed, as well as a large amount of mono-chlorinated material. The starting material was no longer detected by LC-MS. The reaction was continued in time and small aliquots of sulfuryl chloride were added to drive the reaction to completion. After the addition of 3 equivalents of sulfuryl chloride in total, a small amount of the tri-chloro compound was also formed. No work-up was performed in this experiment.

The reaction was repeated on 1 g scale. The sulfuryl chloride (2.25 equivalents) was slowly dosed into the reaction mixture in a controlled manner using a syringe pump. A second aliquot of sulfuryl chloride (0.5 equivalent) was added to drive the reaction to ca. 95% conversion. After aqueous work-up, a yellowish oil was obtained that spontaneously solidified. A quick purification by column chromatography resulted in the complete removal of the remaining 5% mono-chlorinated compound and [11] was obtained as a colorless oil (0.88 g, 64%) that spontaneously solidified. Analysis with LC-MS showed the purity to be >95% and confirmed the mass of the intended product. Analysis with 1H-NMR confirmed the structure.

The synthesis was repeated on 25 g scale and a complete conversion was achieved. After aqueous work-up, the obtained brown oil (31.1 g) was dissolved in heptane (100 mL) and stored at 4° C. overnight, which resulted in the formation of white crystals. These were filtered off and dried on the filter to yield [11] (22.4 g, 65% yield and 98% purity according to LC-MS). The structure was confirmed with $^{13}$C-APT-NMR spectroscopy.

Synthesis of 4,6-dichloro-5-pentylbenzene-1,3-diol [11]

To a cold (0° C.) solution of 5-pentylbenzene-1,3-diol (25 g, 139 mmol) in dichloromethane (250 ml) was slowly added sulfuryl chloride (46.8 g, 347 mmol, 28.1 ml) over a 30 minute period. The resulting mixture was stirred over night while slowly warming to room temperature. The reaction mixture was quenched with 1M aq. NaOH (150 mL) and subsequently stirred for 15 minutes. The formed slurry was diluted with extra DCM (100 mL) and then acidified to pH ~3 with 3M aq. HCl. The layers were separated and the aqueous phase was extracted once with DCM (150 mL). The combined organic layers were dried on Na$_2$SO$_4$ and all volatiles evaporated in vacuo using a rotary evaporator. Un-purified 31.1 g brown/yellow oil. The oil was dissolved in heptane (100 mL) and stored the solution at 4° C. The formed crystals were filtered off and then dried on filter by air stream. Yield: 22.4 g slightly yellow solid (65% yield). LC-MS: purity 98%, [M–H]=247. $^{1}$H-NMR δ (400 MHz, CDCl$_3$): 6.62 (s, 1H), 5.61 (s, 2H), 2.90-2.81 (m, 2H), 1.62-1.50 (m, 2H), 1.45-1.31 (m, 4H), 0.92 (t, J=7.0 Hz, 3H).

The coupling with menthadienol towards (1'R,2'R)-3,5-dichloro-5'-methyl-4-pentyl-2'-(prop-1-en-2-yl)-1',2',3',4'-tetrahydro-[1,1'-biphenyl]-2,6-diol [12] was investigated on 1 g scale. Using the same conditions as used for the bromide-analogue, [11] was coupled with menthadienol (1 equivalent) at –35° C. using p-toluenesulfonic acid (0.5 eq.). The reaction was monitored with LC-MS and two further aliquots of menthadienol were added (0.3 and 0.15 eq.) over the course of 4 hours. A mixture of starting material (22%), product (56%) and a possible intermediate (22%) was obtained. The reaction was then allowed to slowly warm to room temperature overnight. Upon warming, an unknown product (50%) was formed presumably the already ring-closed product, analogous to the bromide. The remainder of the mixture was mainly product (42%).

The experiment was repeated on 1 g scale and the reaction was monitored carefully over time. Again, several aliquots of menthadienol were added. After a total reaction time of 5 hours, the reaction was still incomplete. After aqueous work-up and subsequent purification by column chromatography to remove the unreacted material, 1.06 g of [11] was obtained as a colorless oil (66% yield) with a purity of >98% according to LC-MS.

Synthesis of (1'R,2'R)-3,5-dichloro-5'-methyl-4-pentyl-2'-(prop-1-en-2-yl)-1',2',3',4'-tetrahydro-[1,1'-biphenyl]-2,6-diol [12]

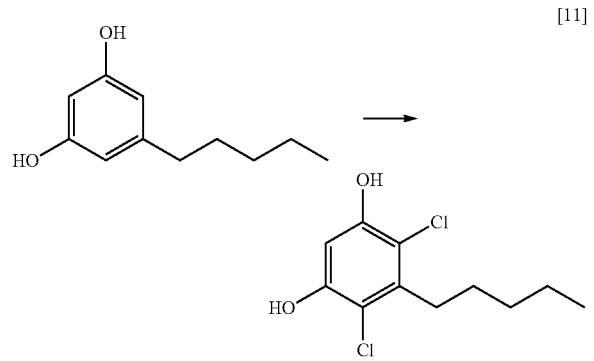

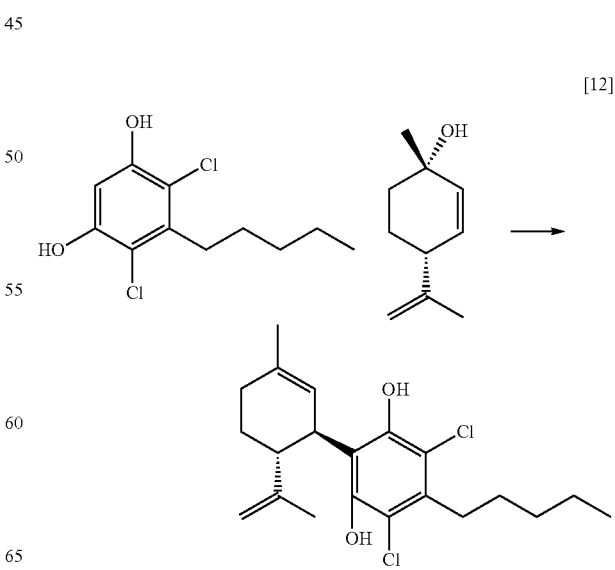

A mixture of 4,6-dichloro-5-propylbenzene-1,3-diol (1 g, 4.52 mmol), (1R,4R)-1-methyl-4-(prop-1-en-2-yl)cyclohex-2-enol (0.689 g, 4.52 mmol) and magnesium sulfate (1.361 g, 11.31 mmol) in dichloromethane (10 mL) was cooled to −35° C. Then, p-toluenesulfonic acid monohydrate (0.430 g, 2.262 mmol) was added in one portion and the mixture was stirred for 90 minutes. A second aliquot of (1R,4R)-1-methyl-4-(prop-1-en-2-yl)cyclohex-2-enol (0.207 g, 1.357 mmol) was added and the mixture was stirred for 90 minutes. A third aliquot of (1R,4R)-1-methyl-4-(prop-1-en-2-yl)cyclohex-2-enol (0.103 g, 0.678 mmol was added and the mixture was stirred for 5.5 hours. A fourth aliquot of (1R,4R)-1-methyl-4-(prop-1-en-2-yl)cyclohex-2-enol (0.103 g, 0.678 mmol) was added and the mixture was stirred for 90 minutes. The reaction mixture was quenched by pouring into a solution of dibasic potassium phosphate, (0.709 g, 4.07 mmol) in water (10.0 mL). The layers were separated with a phase separator and the organic phase was evaporated in vacuo using a rotary evaporator. The obtained oil was stirred in methanol (5 mL) at 0° C. for 1 hour, then all undissolved solids were filtered off using a folded paper filter. Un-purified yield: 1.06 g almost colorless oil. The oil was purified by column chromatography (120 g silica; eluent: heptane (A)/ethyl acetate (B); gradient: t=0 min. 0% B, t=25 min. 10% B). Yield: 0.44 g colorless oil (27% yield). LC-MS: purity 100%, [M−H]=381. $^1$H-NMR δ (400 MHz, CDCl$_3$): 6.39 (s, 1H), 5.60 (s, 1H), 5.46 (s, 1H), 4.53 (s, 1H), 4.42 (s, 1H), 4.08-3.98 (m, 1H), 2.90-2.75 (m, 2H), 2.62-2.51 (m, 1H), 2.31-2.16 (m, 1H), 2.14-2.03 (m, 1H), 1.87-1.72 (m, 5H), 1.68 (s, 3H), 1.60-1.46 (m, 2H), 1.44-1.29 (m, 4H), 0.91 (t, J=6.9 Hz, 3H).

For the dechlorination step, [11] was used as a model compound since only a limited amount of [12] was obtained. The same conditions for the debromination (Na$_2$SO$_3$ (2.65 eq.), L-ascorbic acid (0.15 eq.), triethylamine (3.6 eq.), a methanol/water mixture, 75° C.) were applied on [11] on 250 mg scale. After stirring for 1 hour, no conversion was observed. After stirring overnight, some decomposition was observed.

The dechlorination step was repeated using the same scale and conditions but using 2-propanol instead of methanol. The reaction temperature was increased to 100° C. No conversion was achieved after stirring overnight. No decomposition was detected after reacting overnight.

The dechlorination step was repeated using triethylsilane mediated, Pd$_2$(d-t-bppf)Cl$_2$ catalyzed reaction conditions as described in Tet. Lett., 2013, 54, 4518-4521. A degassed solution of [11] (250 mg) in dioxane was treated with triethylsilane (5 eq.), triethylamine (2 eq.) and Pd$_2$(d-t-bppf)Cl$_2$ (5 mol %). After stirring for 1 hour at 100° C., near complete conversion into a new product was observed with LC-MS. After aqueous work-up, the newly formed product could not be isolated nor detected in significant amounts in either the organic or aqueous phase.

[12] was used for the dechlorination step. A solution of compound [12] (100 mg) in dioxane was treated with triethylsilane (5 eq.), triethylamine (2 eq.) and Pd$_2$(d-t-bppf)Cl$_2$ (5 mol %). After stirring at 100° C. overnight, partial conversion into a new product was observed with LC-MS with 36% starting material remaining, 44% of a new and unknown product and only 6% of a product with the correct retention time of the fully dechlorinated cannabidiol. The compounds did not ionize properly on the LC-MS systems and no useful mass traces were obtained.

The removal of the chloride protection groups was tested by catalytic hydrogenation. A solution of [11] (60 mg) in methanol (1 mL) was treated with palladium on carbon (5 mg, 10% metal loading) under hydrogen atmosphere at ambient pressure. After stirring for 2 hours, partial conversion into a new product was observed with LC-MS but no mass was observed in the mass trace. After stirring overnight a complete conversion was achieved. Subsequent filtration to remove the catalyst and evaporation of the solvent yielded 40 mg of a yellowish oil. Analysis with $^1$H-NMR revealed that the characteristic protons of the double bond were no longer present and also no increase in the number of aromatic signals was found.

Figure 7:
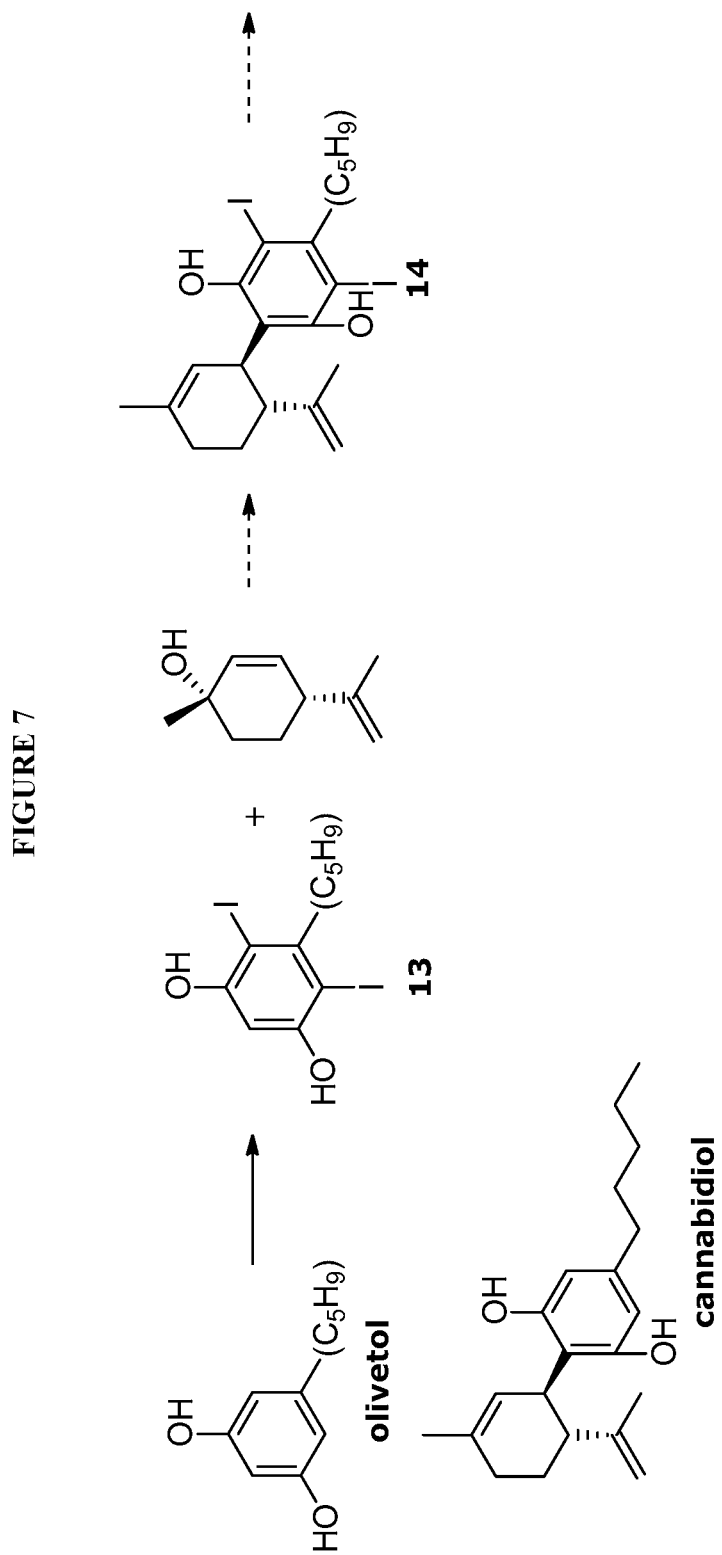
FIG. 7 shows an exemplary synthetic pathway for cannabidiol using iodide protective groups.

Adding Iodide as Protection Group:

The iodination of olivetol towards cannabidiol was performed as shown in FIG. 7. Olivetol (100 mg) was treated with N-iodosaccharin (2.1 equivalents) in MeCN at room temperature. After stirring overnight, a complete conversion was observed with LC-MS and the correct mass was found in the mass trace but several unknown other signals were observed as well, one of them presumably being the saccharine residue.

After evaporation of the solvent in vacuo and subsequent trituration in methanol to remove most of the solid saccharin residue, the obtained clear filtrate was evaporated in vacuo to yield 234 mg of an orange/red oil that still contained some solids. This material was further purified by Reveleris® column chromatography using silica and heptane/ethyl acetate as eluent to yield a colorless oil (108 mg, 45% yield) that solidified upon scratching with a spatula. Analysis with LC-MS showed the purity to be >98% and the structure was confirmed with $^1$H-NMR.

Repetition of the synthesis of 4,6-diiodo-5-pentylbenzene-1,3-diol [13] on 1.25 g scale was performed. After evaporation of the solvent in vacuo and subsequent trituration in methanol to remove most of the solid saccharin residue, the obtained clear filtrate was evaporated in vacuo and then further purified by Reveleris® column chromatography using silica and heptane/ethyl acetate as eluent to yield a colorless oil (1.70, 57% yield), which solidified spontaneously. Analysis with LC-MS showed the purity to be 97%.

Synthesis of 4,6-diiodo-5-pentylbenzene-1,3-diol [13]

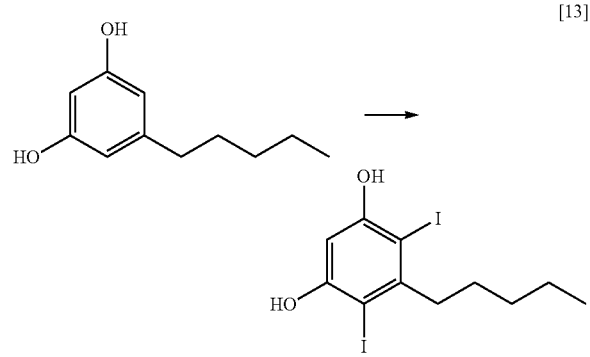

A mixture of 5-pentylbenzene-1,3-diol (1.25 g, 6.94 mmol) and N-iodosaccharin (4.50 g, 14.56 mmol) in acetonitrile (anhydrous, 12.5 mL) was stirred overnight (in darkness). All volatiles were evaporated in vacuo using a rotary evaporator and the obtained residue was stirred in a minimal amount of methanol overnight. The undissolved material was filtered off and the filtrate was evaporated in vacuo using a rotary evaporator. The oil was purified by column chromatography (120 g silica; eluent: heptane (A)/ ethyl acetate (B); gradient: t=0 min. 1% B, t=5 min. 1% B, t=30 min. 5% B). Yield: 1.70 g colorless oil (57% yield). The oil solidified spontaneously. LC-MS: purity 98%, [M−H]=430. $^1$H-NMR δ (400 MHz, CDCl$_3$): 6.56 (s, 1H), 5.94 (s, 1H), 5.39 (s, 1H), 2.71-2.57 (m, 2H), 1.64-1.47 (m, 2H), 1.46-1.23 (m, 4H), 1.00-0.81 (m, 3H).

The reaction of [13] with menthadienol was performed on 100 mg scale. After multiple additions of menthadienol, increasing the temperature to 40° C. and stirring overnight, a large amount of [13] was found by LC-MS and the mass of (1'R,2'R)-3,5-diiodo-5'-methyl-4-pentyl-2'-(prop-1-en-2-yl)-1',2',3',4'-tetrahydro-[1,1'-biphenyl]-2,6-diol [14] was not detected in the mass trace. The reaction was repeated with 1 equivalent of p-Tos-OH (compared to the normal 0.5 eq.) but no conversion was seen.

Different Lewis acids were screened on 50 mg scale. Glass vials were charged with iodide [13] (50 mg), magnesium sulfate (3 eq.) and the Lewis acid to be tested (1 eq.). The vials were placed in a pre-cooled reaction block at −35° C. A pre-cooled solution of menthadienol (2 eq.) in dichloromethane (1 mL) was added to each vial. The vials were stirred at −35° C. for 2 hours and samples (20 uL) were taken from each vial and subsequently analysed with HPLC. Table 2 lists the results. No conditions were found to couple [13] with menthadienol. Di-iodide is found to be not reactive toward menthadienol.

TABLE 2

Overview of Lewis acid screening

| Lewis acid | Results |
|---|---|
| Lithium chloride | No conversion |
| Nickel(II)chloride | No conversion |
| Copper(II)chloride | No conversion |
| Copper(I)chloride | No conversion |
| Zinc chloride | No conversion |
| Iron(II)chloride | No conversion |
| Iron(III)chloride | No conversion |
| Manganese(II)chloride | No conversion |
| Cerium(III)chloride | No conversion |
| Cobalt(II)chloride | No conversion |
| Indium(III)chloride | No conversion |
| Bismuth(III)chloride | No conversion |
| Samarium(III)chloride | No conversion |

Overall, 5-propylbenzene-1,3-diol (the C3-olivetol analogue) prepared in Example 2 was successfully di-halo protected using bromide protection groups. Using the bromide protection groups both (1'R,2'R)-5'-methyl-2'-(prop-1-en-2-yl)-4-propyl-1',2',3',4'-tetrahydro-[1,1'-biphenyl]-2,6-diol (the C3-cannabidiol-analogue) and (6aS,10aR)-6,6,9-trimethyl-3-propyl-6a,7,8,10a-tetrahydro-6H-benzo[c]chromen-1-ol (the C3-THC analogue) were prepared with two different synthetic pathways demonstrated for the C3-THC analogue. The syntheses proceeded similarly to the C5-isomer. The synthesis of dichloro-olivetol and diiodo-olivetol using the C5-isomer was also performed successfully. Subsequent coupling with menthadienol was successful for the dichloro-olivetol, but not for the diiodo-olivetol.

Example 4—Reaction of Dibromo-Olivetol with Other Olefins

Figure 8:
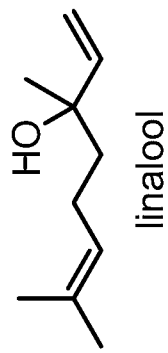
FIG. 8 shows exemplary olefins used in coupling reactions with dibromo-olivetol.

The coupling of dibromo-olivetol with other olefins was performed. Dibromo-olivetol was coupled with the compounds in FIG. 8, including cyclohexene, octane, cyclohex-2-enol and linalool. A mixture of dibromo-olivetol (250 mg), the olefin to be coupled (1 eq.), magnesium sulfate (2.5 eq.) in DCM (2.5 mL) was treated with p-Tos-OH (0.5 eq.) at room temperature. After stirring for 2 hours, no conversion was observed with LC-MS, except for the experiment in which cyclohex-2-enol was used as coupling partner.

Figure 9:
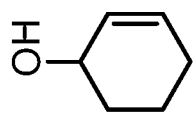
FIG. 9 shows the structure of dibromo-olivetol coupled with cyclohex-2-enol.
Figure 9:
Figure 9:
Figure 9:
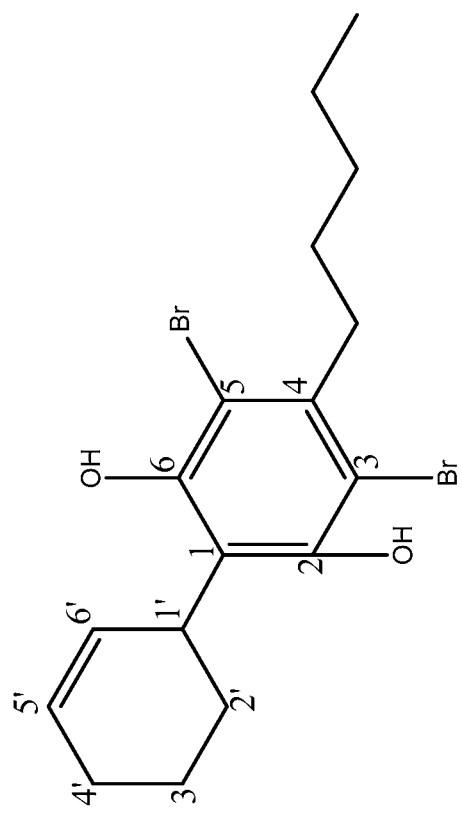

Using cyclohex-2-enol, full conversion into a new product was observed. After a simple aqueous work-up, the experiment with cyclohex-2-enol as coupling partner yielded 223 mg of a brownish oil with a purity of 94% according to LC-MS. In the mass trace, a mass of [M−H]=417 was found. Combined with the structural data obtained from the $^1$H-NMR spectrum it is believed that the formed compound is (S)-3,5-dibromo-4-pentyl-1',2',3',4'-tetrahydro-[1,1'-biphenyl]-2,6-diol, the structure of which is shown in FIG. 9.

The coupling of dibromo-olivetol with linalool was repeated using THF as solvent so that a higher reaction temperature could be achieved. The amount of p-Tos-OH was also reduced to 0.1 eq. to prevent potential side reactions and/or decomposition. LC-MS indicated formation of a new product with still 47% starting material remaining after reacting overnight at 65° C. After aqueous work-up, the starting material was recovered with a purity of 73% according to LC-MS.

The coupling of dibromo-olivetol (C5-analogue) with different olefins has proven feasible. The coupling of dibromo-olivetol, and related compounds, can be performed using a cyclic olefin containing a double bond and a hydroxy-group at a conjugated position. In some embodiments, the olefin can be any olefin as described herein, provided the olefin is not cyclohexene, octane, linalool or combinations thereof.

Synthesis of 3,5-dibromo-4-pentyl-1',2',3',4'-tetrahydro-[1,1'-biphenyl]-2,6-diol

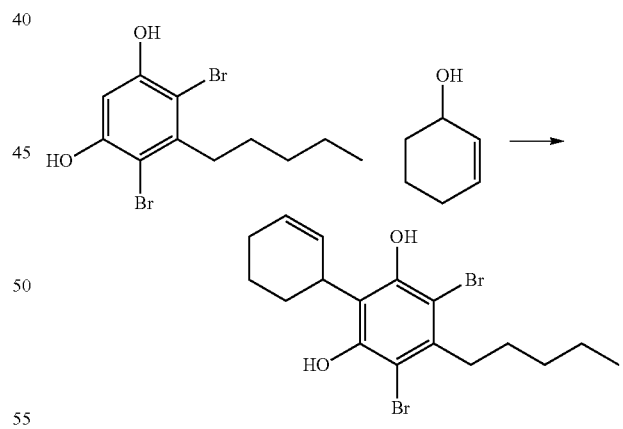

To a mixture of 4,6-dibromo-5-pentylbenzene-1,3-diol (0.25 g, 0.740 mmol), cyclohex-2-enol (0.073 g, 0.740 mmol) and magnesium sulfate (0.223 g, 1.849 mmol) in dichloromethane (2.5 ml) was added p-toluenesulfonic acid monohydrate (0.070 g, 0.370 mmol) in one portion at room temperature. The resulting mixture was stirred overnight and then quenched with a solution of dibasic potassium phosphate, (0.116 g, 0.666 mmol) in water (2.5 ml). The layers were separated with a phase separator and the organic phase was evaporated in vacuo using a rotary evaporator. Yield: 223 mg brownish oil (69% yield). LC-MS: purity 94%,

[M–H]=417. $^1$H-NMR δ (400 MHz, CDCl$_3$): 6.48-5.92 (m, 3H), 5.83 (d, J=10.0 Hz, 1H), 4.13-4.03 (m, 1H), 2.99-2.87 (m, 2H), 2.21-2.09 (m, 2H), 2.01-1.82 (m, 2H), 1.79-1.62 (m, 2H), 1.61-1.49 (m, 2H), 1.48-1.32 (m, 4H), 0.93 (t, J=7.0 Hz, 3H).

Example 5—Synthesis of (1R,2R,4S)-2-(dimethyl-amino)-1-methyl-4-(prop-1-en-2-yl)cyclohexan-1-ol

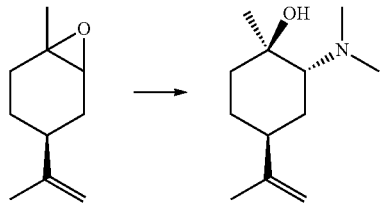

To a solution of (−)-limonene oxide (39.73 g, 261 mmol) in ethanol (70 mL) was added a 40% solution of dimethylamine in water (62.3 g, 553 mmol, 70 mL). The mixture was heated to 65° C. and stirred for 26 hours. A clear yellow solution was formed. The mixture was allowed to cool to room temperature and all volatiles evaporated in vacuo using a rotary evaporator. The mixture was taken up in MTBE (90 mL) and washed with water (30 mL). The solution was then dried over Na$_2$SO$_4$, filtered and the residue washed with MTBE (20 mL). To the resulting solution was slowly added a solution of oxalic acid (10.28 g, 114 mmol) in acetone (40 mL) forming a thick white precipitate which required mechanical stirring. The precipitate was heated to reflux for 30 min. After cooling to room temperature and stirring for 2 hours the precipitate was filtered and the residue washed with MTBE (100 mL). The resulting white hydroscopic solid was transferred back into the reaction vessel and suspended in 30 mL ethanol. The suspension was heated to reflux forming a yellow emulsion. MTBE (150 mL) was added dropwise forming a white precipitate. The suspension was allowed to cool to room temperature and stirred overnight. The suspension was filtered and washed twice with MTBE:ethanol (4:1, 50 mL). The resulting white solid was dissolved in water (71 mL) and MTBE (55 mL). Under vigorous stirring a 2N solution of KOH was added (130 mL). The phases were separated, the organic phase was dried over Na2SO4 and concentrated in vacuo. Yield: 20.96 g of a colourless oil (40.7% yield). GCMS: purity 98.9%, [M]=197.

Example 6—Synthesis of (1R,4S)-1-methyl-4-(prop-1-en-2-yl)cyclohex-2-en-1-ol (1R,4S-mentha-dienol)

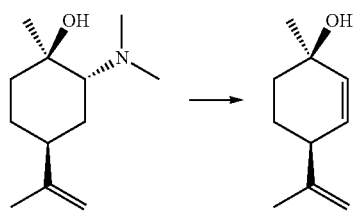

A solution of (1R,2R,4S)-2-(dimethylamino)-1-methyl-4-(prop-1-en-2-yl)cyclohexan-1-ol (24.68 g, 125 mmol) in ethanol (50 mL) was heated to reflux. Upon reaching reflux a solution of hydrogen peroxide (17.76 g, 157 mmol, 30%) was added dropwise. After complete addition the mixture was refluxed for 2.5 hours. After cooling to room temperature the reaction was quenched by addition of sodium sulfite (5.12 g, 40.6 mmol) in water (18 mL). After a peroxide teststrip revealed no peroxides were present the reaction mixture was diluted with acetone (60 mL) resulting in a white suspension. The precipitate was removed by filtration and the residue washed with acetone (60 mL). Concentration in vacuo using a rotary evaporator resulted in 30.05 g of the N-oxide as a yellow oil. The N-oxide was transferred to a Kugelrohl flask and subsequently pyrolyzed at 160 C at 15 mBar pressure. The clear oil slowly turned orange and after complete removal of solvents solidified to an orange solid which melted upon further heating. A clear oil was collected which was dissolved in MTBE (60 mL) and washed with water (16 mL) followed by washing with a cooled solution of 1% sulfuric acid (1×16 mL, 2×10 mL). The organic phase was then washed with satd. NaHCO$_3$ solution (2 mL), subsequently dried over Na$_2$SO$_4$ and concentrated in vacuo using a rotary evaporator. Yield: 15.15 g of a colourless oil (80% yield). GCMS: purity 95%, [M]=152. Chiral HPLC: enantiomeric excess 99%.

Example 7—Synthesis of (1'S,2'S)-3,5-dibromo-5'-methyl-4-pentyl-2'-(prop-1-en-2-yl)-1',2',3',4'-tetra-hydro-[1,1'-biphenyl]-2,6-diol

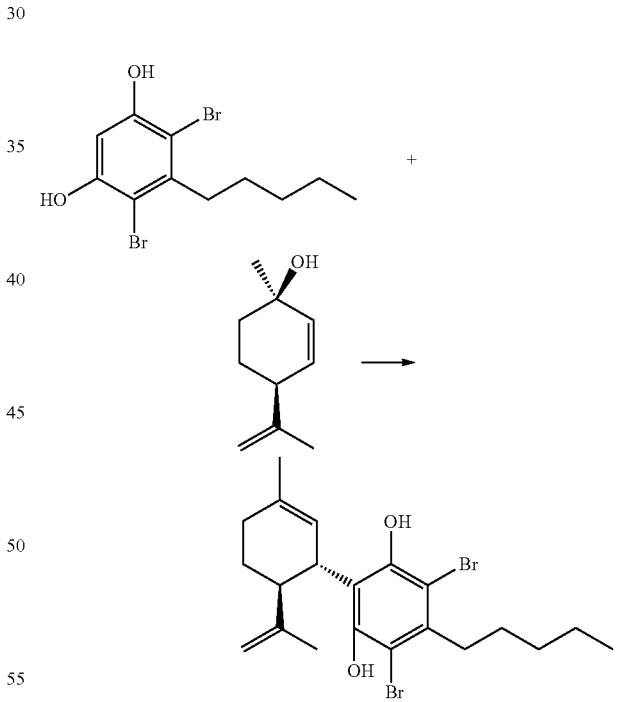

A mixture of 4,6-dibromo-5-pentylbenzene-1,3-diol (16.2 g, 43.6 mmol), (1R,4S)-1-methyl-4-(prop-1-en-2-yl)cyclohex-2-en-1-ol (4.35 g, 28.6 mmol) and magnesium sulfate (15 g, 125 mmol) in dichloromethane (100 mL) was cooled to −30° C. Then, p-toluenesulfonic acid monohydrate (4.19 g, 22.03 mmol) was added in one portion and the resulting mixture was stirred at −30° C. The reaction was monitored with LCMS and over the course of 5 hours, extra aliquots of (1R,4S)-1-methyl-4-(prop-1-en-2-yl)cyclohex-2-en-1-ol (4.26 g, 27.9 mmol and 1.95 g, 12.8 mmol respectively)

were added before stirring the mixture at −30° C. The reaction mixture was poured into a solution of dibasic potassium phosphate (7.60 g, 43.6 mmol) in water (150 mL) and the layers were separated. The aqueous phase was extracted with DCM (40 mL) and the combined organic layers were concentrated to dryness in vacuo using a rotary evaporator. The obtained oil was dissolved in methanol (150 mL) and then stirred for 1.5 hours at −15° C. A white solid was removed by filtration and was discarded. The filtrate containing the product was used as is in the next reaction step. LCMS: purity 77%, [M+H]=471.

Example 8—Synthesis of (1'S,2'S)-5'-methyl-4-pentyl-2'-(prop-1-en-2-yl)-1',2',3',4'-tetrahydro-[1,1'-biphenyl]-2,6-diol

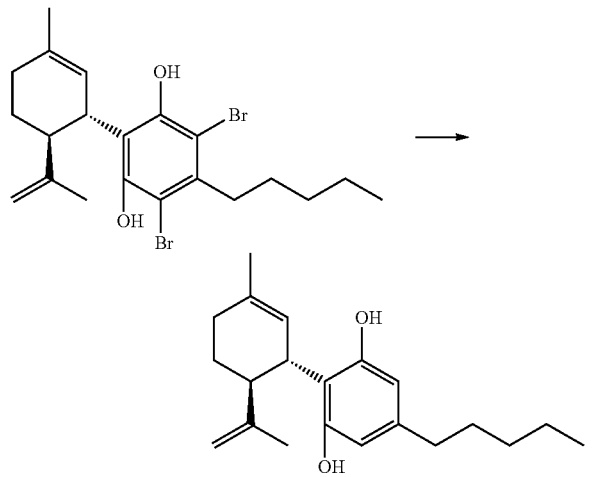

To a solution of (1'S,2'S)-3,5-dibromo-5'-methyl-4-pentyl-2'-(prop-1-en-2-yl)-1',2',3',4'-tetrahydro-[1,1'-biphenyl]-2,6-diol (assumed 20.59 g, 43.6 mmol) in methanol (180 ml) was added a solution of sodium sulfite (15.92 g, 126 mmol) and L-ascorbic acid (1.24 g, 0.608 mmol) in water (150 mL). A yellow suspension was formed, triethylamine (17.42 g, 172 mmol, 24 ml) was added in one portion. The resulting mixture was heated to 70° C. for 22 hours, subsequently 62 g of solvent were removed by disstillation at 90° C. After cooling to room temperature the pH of the remaining aqueous phase was adjusted to ~4 with concentrated hydrochloric acid. Heptane (40 mL) was added and the mixture was stirred for 30 minutes. The layers were separated, the organic phase was washed with brine (20 mL) and dried over $Na_2SO_4$. The resulting brown solution was cooled to −20° C. in attempts to crystallize the material. After several attempts at cooling, further concentration and recooling. A sample was cooled on dry ice under vigorous scratching, forming white crystals. These were used to seed the remaining solution which immediately crystallized. Yield: 7.65 g of off-white crystals (55% yield). LCMS: purity 99.3%, [M+H]=315. Chiral HPLC: enantiomeric excess 99%. $^1$H-NMR δ (400 MHz, $CDCl_3$): 6.40-6.10 (br, 2H), 6.00 (br, 1H), 5.57 (s, 1H), 4.79 (br, 1H), 4.65 (s, 1H), 4.55 (s, 1H), 3.90-3.10 (m, 1H), 2.46-2.36 (m, 3H), 2.29-2.17 (m, 1H), 2.14-2.05 (m, 1H), 1.87-1.71 (m, 5H), 1.66 (s, 3H), 1.55 (p, J=7.6 Hz, 2H), 1.37-1.22 (m, 4H), 0.87 (t, J=7.0 Hz, 3H).

While this disclosure has been particularly shown and described with reference to example embodiments thereof, it will be understood by those skilled in the art that various changes in form and details may be made therein without departing from the scope of the invention encompassed by the appended claims.

We claim:

1. A process for the preparation of a compound of formula (I)

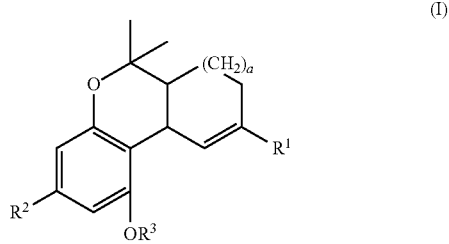

wherein a is 1;

$R^1$ and $R^2$ are each independently selected from the group consisting of H, OH, protected hydroxyl, alkyl, alkenyl, alkynyl, acyl, aryl, heteroaryl, cycloalkyl or heterocycle;

wherein the alkyl, alkenyl, alkynyl or acyl is optionally substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl or heterocycle; wherein $R^A$ and $R^B$ are each independently selected from hydrogen and $C_{1-4}$ alkyl;

wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl;

$R^3$ is selected from the group consisting of H, alkyl, acyl, —$SO_2$-alkyl, —$SO_2$-aryl and —$SO_2$— heteroaryl; wherein the alkyl is optionally substituted with one or more substituents independently selected from the group consisting of halogen, —OH, alkyl, —O-alkyl, $NR^ER^F$, —S— alkyl, —SO-alkyl, —$SO_2$-alkyl, aryl and heteroaryl; and wherein $R^E$ and $R^F$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, $NR^GR^H$, —S-alkyl, —SO-alkyl and —$SO_2$-alkyl; wherein $R^G$ and $R^H$ are each independently selected from hydrogen and $C_{1-4}$ alkyl;

or a pharmaceutically acceptable salt or ester thereof;

the process comprises reacting a compound of formula (II), wherein each X is independently selected from the group consisting of Br, F and Cl, with a compound of formula (III) wherein $R^0$ is OH, in the presence of a protic or first Lewis acid catalyst to form a compound of formula (IV);

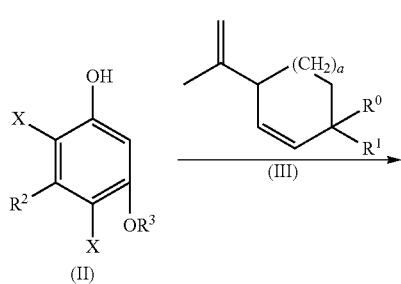

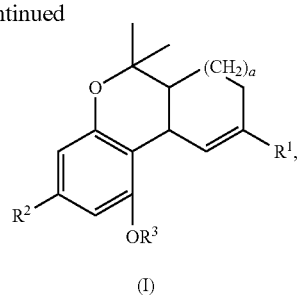

or (ii) reacting the compound of formula (IV) with a reducing agent to form a compound of formula (VI); and then

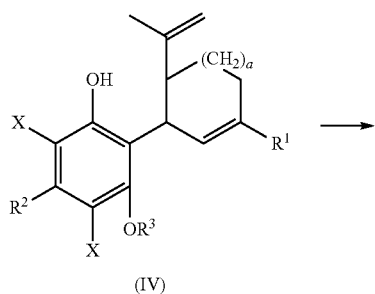

then either (i) cyclizing the compound of formula (IV) by reacting the compound of formula (IV) with a second Lewis acid catalyst to form a compound of formula (V); and then

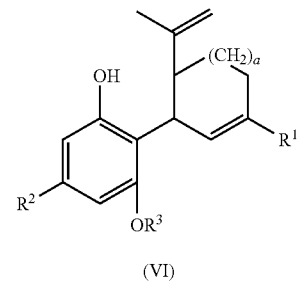

cyclizing the compound of formula (VI) by reacting the compound of formula (VI) with a second Lewis acid catalyst to form the compound of formula (I)

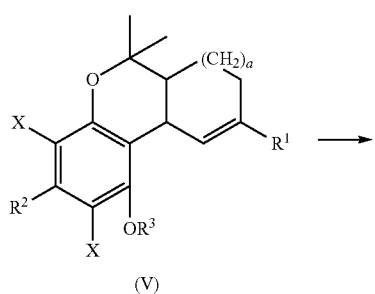

reacting the compound of formula (V) with a reducing agent to form the compound of formula (I)

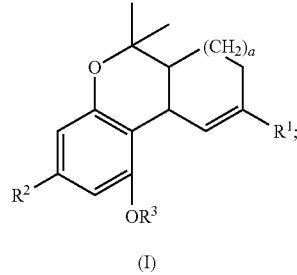

and optionally converting the compound of formula (I) into its pharmaceutically acceptable salt or ester thereof.

2. The process of claim 1 wherein the process comprises cyclizing the compound of formula (IV) by reacting the compound of formula (IV) with a second Lewis acid catalyst to form a compound of formula (V); and then

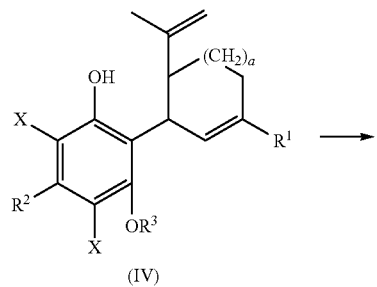

(IV)

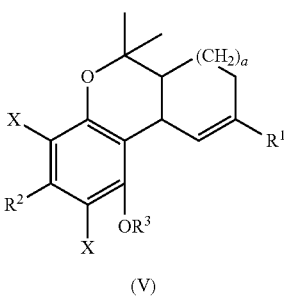

(V)

reacting the compound of formula (V) with a reducing agent to form the compound of formula (I)

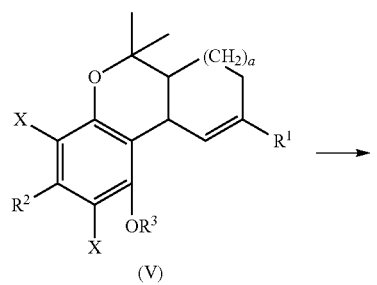

(V)

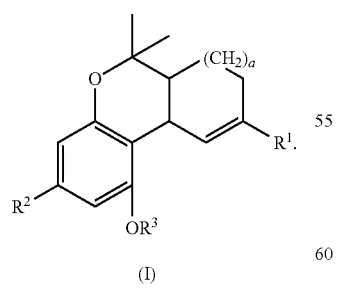

(I)

3. The process of claim 1 wherein the process comprises reacting the compound of formula (IV) with a reducing agent to form a compound of formula (VI); and then

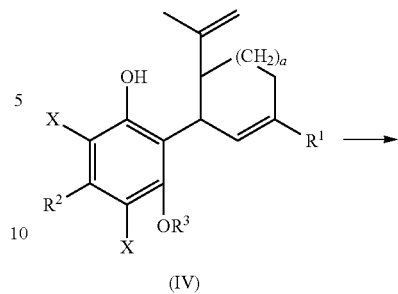

(IV)

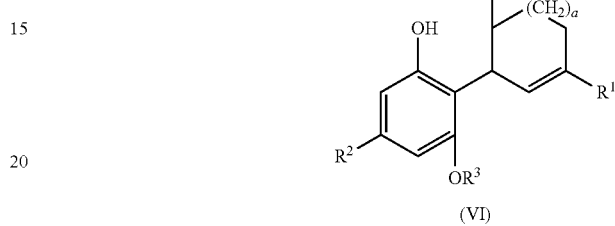

(VI)

cyclizing the compound of formula (VI) by reacting the compound of formula (VI) with a second Lewis acid catalyst to form the compound of formula (I)

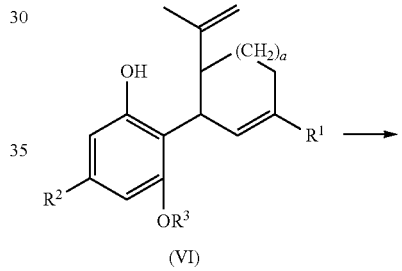

(VI)

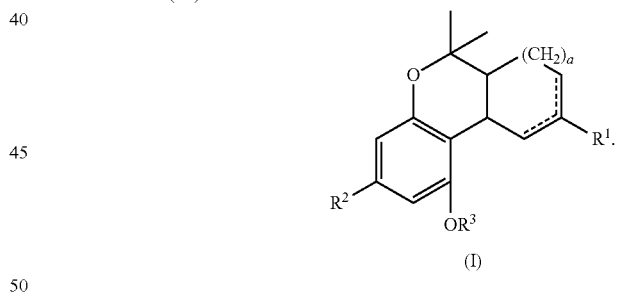

(I)

4. The process of claim 1, wherein the compound of formula (I) is a compound of formula (XI)

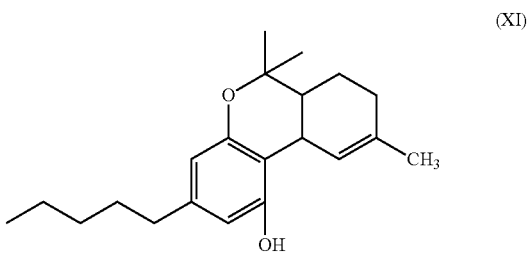 [SMILES: CCCCCc1cc(O)c2c(c1)OC(C)(C)C1CCC(C)=CC21]

(XI)

or a pharmaceutically acceptable salt or ester thereof;

wherein, the process comprises reacting a compound of formula (XII), wherein each X is independently selected from Br, F or Cl, with a compound of formula (XIII) in the presence of a protic or first Lewis acid catalyst to form a compound of formula (XIV);

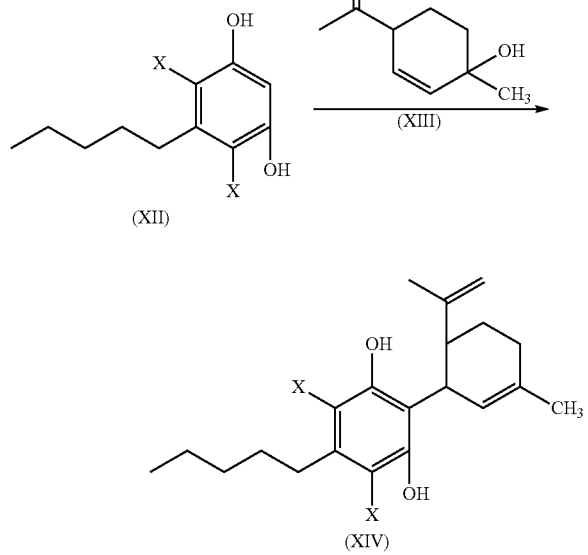

(XII) (XIII)

(XIV)

cyclizing the compound of formula (XIV) by reacting the compound of formula (XIV) with a second Lewis acid catalyst to form a compound of formula (XV); and then

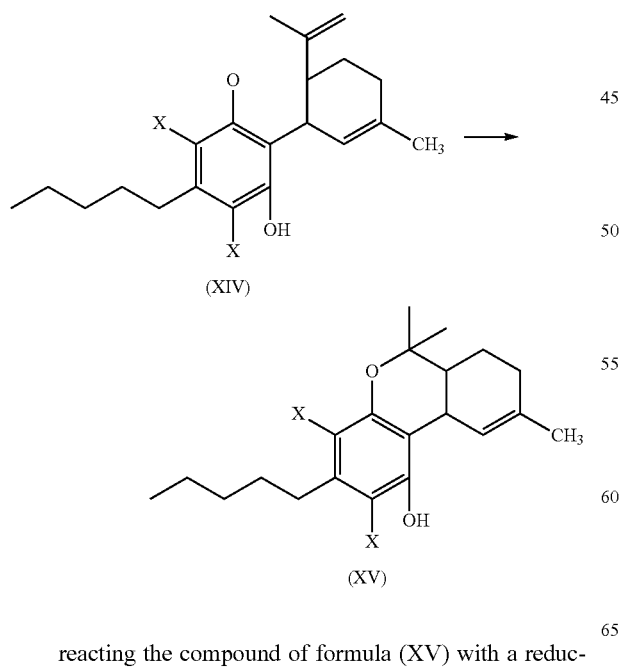

(XIV)

(XV)

reacting the compound of formula (XV) with a reducing agent to form the compound of formula (XI)

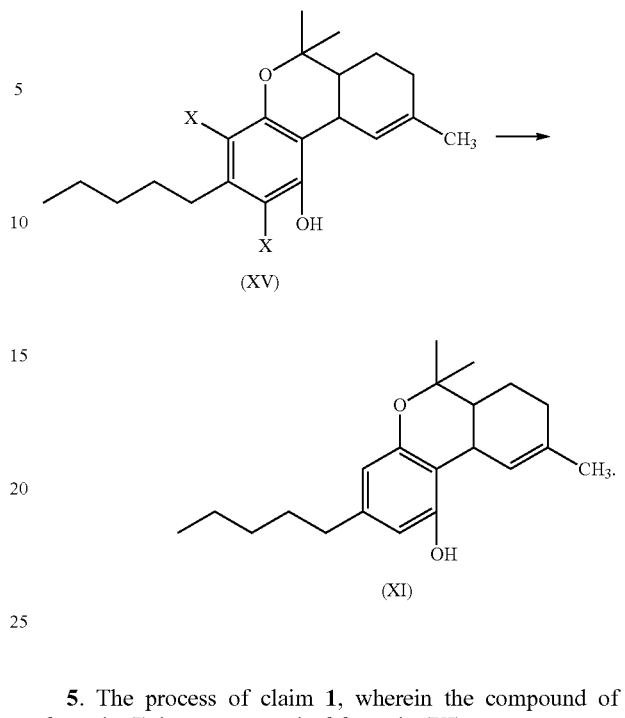

(XV)

(XI)

5. The process of claim 1, wherein the compound of formula (I) is a compound of formula (XI)

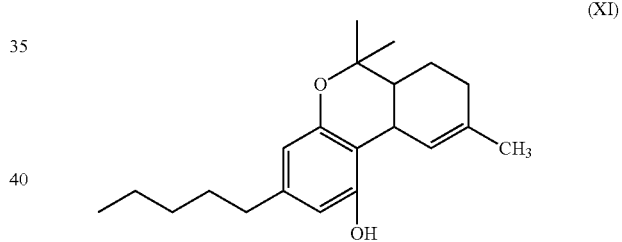

(XI)

or a pharmaceutically acceptable salt or ester thereof;

wherein, the process comprises reacting a compound of formula (XII), wherein each X is independently selected from Br, F or Cl, with a compound of formula (XIII) in the presence of a protic or first Lewis acid catalyst to for a compound of formula (XIV)

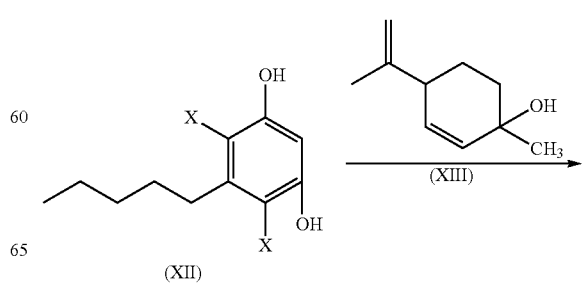

(XII)

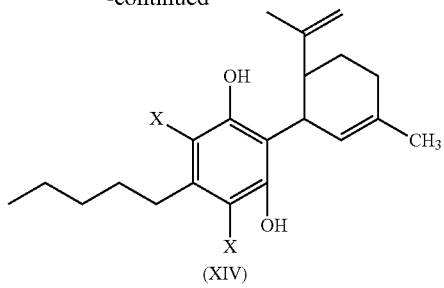

(XIV)

reacting the compound of formula (XIV) with a reducing agent to form a compound of formula (XVI); and then

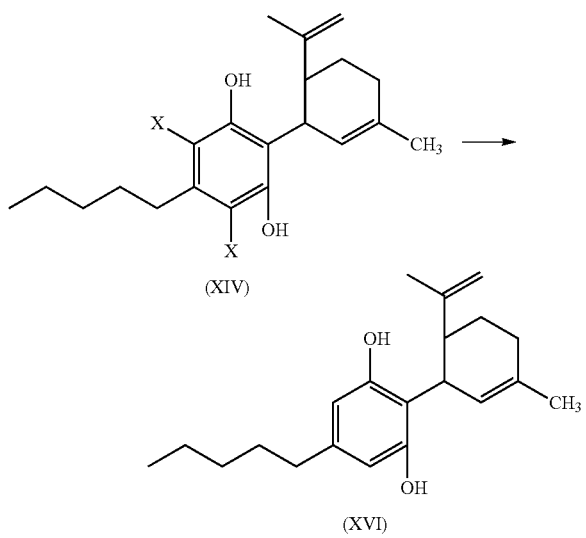

cyclizing the compound of formula (XVI) by reacting the compound of formula (XVI) with a second Lewis acid catalyst to form the compound of formula (XI)

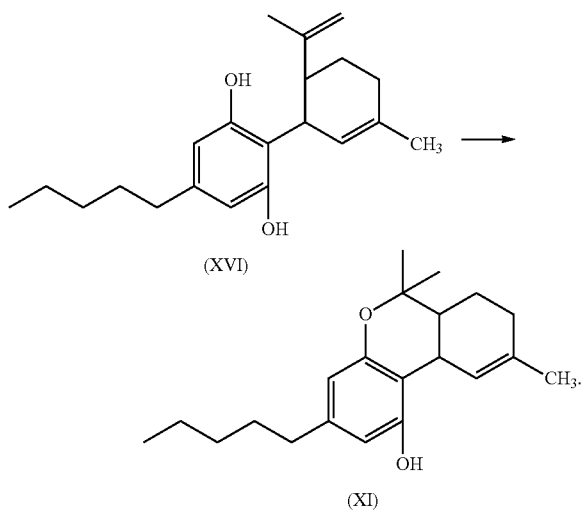

6. The process of claim 1 wherein the compound of formula (I) is selected from the group consisting of delta-9-tetrahydrocannabinol and delta-8-tetrahydrocannabinol.

7. The process of claim 1 wherein the protic or first Lewis acid catalyst is selected from the group consisting of p-toluene sulfonic acid, trifluoromethanesulfonic acid, trifluoroacetic acid, acetic acid, sulfuric acid, iron(II) chloride, scandium(III) triflate, zinc chloride, aluminum chloride and combinations thereof.

8. The process of claim 1 wherein the second Lewis acid catalyst is selected from the group consisting of p-toluene sulfonic acid, $BF_3$, diethyl etherate, $BF_3$*AcOH, tri-isobutyl aluminum, and combinations thereof.

9. The process of claim 1 wherein the reducing agent is a sulfur-containing compound.

10. The process of claim 1 wherein the reduction occurs in a polar solvent.

11. The process of claim 1 wherein the reduction occurs in the presence of an organic or weak inorganic base.

12. A process for the preparation of a compound of formula (VI)

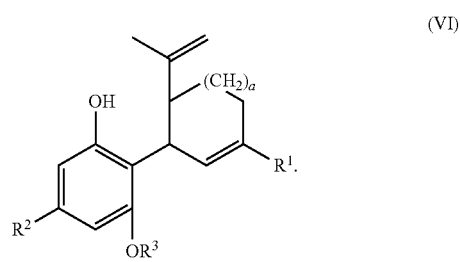

wherein a is 1;

$R^1$ and $R^2$ are each independently selected from the group consisting of H, OH, protected hydroxyl, alkyl, alkenyl, alkynyl, acyl, aryl, heteroaryl, cycloalkyl or heterocycle;

wherein the alkyl, alkenyl, alkynyl or acyl is optionally substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl or heterocycle; wherein $R^A$ and $R^B$ are each independently selected from hydrogen and $C_{1-4}$ alkyl;

wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl;

$R^3$ is selected from the group consisting of H, alkyl, acyl, —$SO_2$-alkyl, —$SO_2$-aryl and —$SO_2$— heteroaryl; wherein the alkyl is optionally substituted with one or more substituents independently selected from the group consisting of halogen, —OH, alkyl, —O-alkyl, $NR^ER^F$, —S— alkyl, —SO-alkyl, —$SO_2$-alkyl, aryl and heteroaryl; and wherein $R^E$ and $R^F$ are each independently selected from hydrogen and $C_{1-4}$ alkyl;

wherein the aryl or heteroaryl, whether alone or as part of a substituent group, is optionally substituted with one or more substituents independently selected from the group consisting of halogen, —OH, alkyl, —O-alkyl, $NR^GR^H$, —S-alkyl, —SO-alkyl and —$SO_2$-alkyl; wherein $R^G$ and $R^H$ are each independently selected from hydrogen and $C_{1-4}$ alkyl;

or a pharmaceutically acceptable salt or ester thereof;

the process comprises reacting a compound of formula (II), wherein each X is independently selected from the group consisting of Br, F and Cl, with a compound of formula (III) wherein $R^0$ is OH, in the presence of a protic or first Lewis acid catalyst to form a compound of formula (IV);

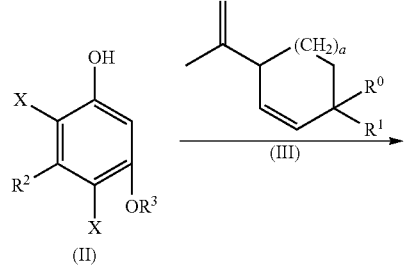

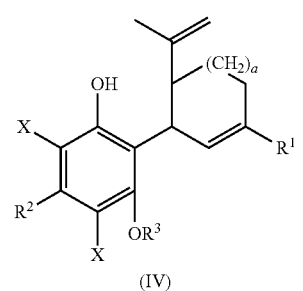

reacting the compound of formula (IV) with a reducing agent to form the compound of formula (VI);

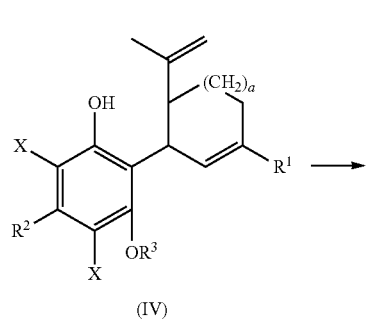

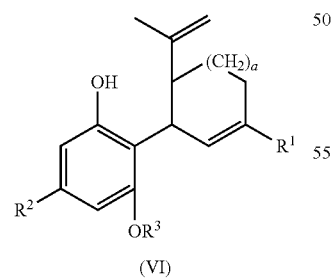

and
optionally converting the compound of formula (VI) into its pharmaceutically acceptable salt or ester thereof.

13. The process of claim 12, wherein the compound of formula (VI) is a compound of formula (XVI)

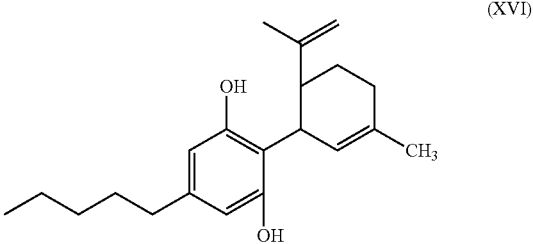 [SMILES: C=C(C)C1CCC(C)=CC1c1c(O)cc(CCCCC)cc1O]

or a pharmaceutically acceptable salt or ester thereof;

wherein, the process comprises reacting a compound of formula (XII), wherein each X is independently selected from Br, F or Cl, with a compound of formula (XIII) in the presence of a protic or first Lewis acid catalyst to form a compound of formula (XIV); and

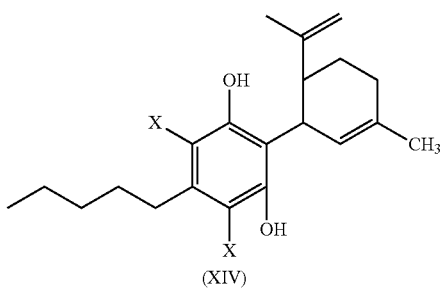

reacting the compound of formula (XIV) with a reducing agent to form the compound of formula (XVI)

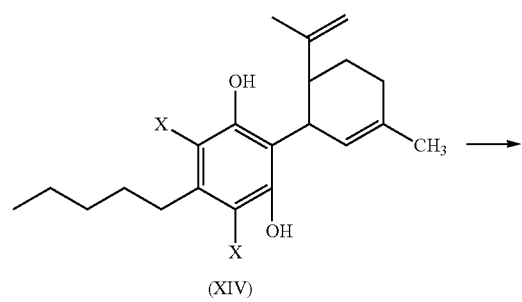

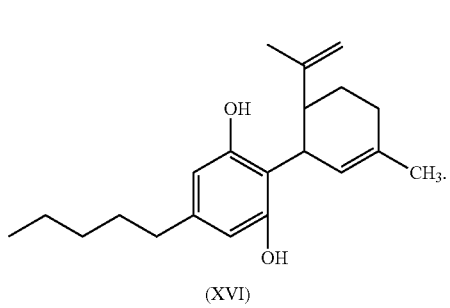

(XVI)

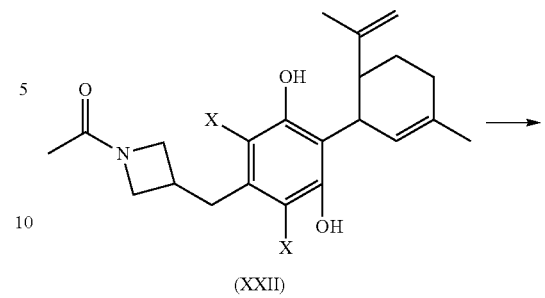

(XXII)

14. The process of claim 12, wherein the compound of formula (VI) is a compound of formula (XX)

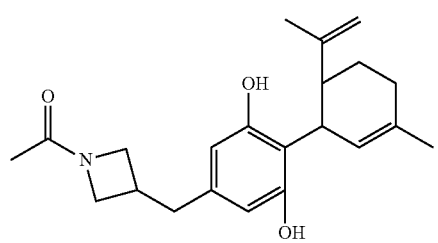

(XX)

or a pharmaceutically acceptable salt or ester thereof;
wherein, the process comprises reacting a compound of formula (XXI), wherein each X is independently selected from Br, F or Cl, with a compound of formula (XIII) in the presence of a protic or first Lewis acid catalyst to form a compound of formula (XXII); and

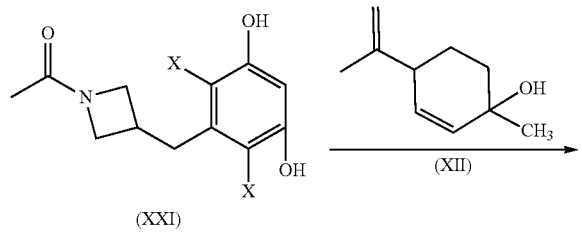

(XXI) (XII)

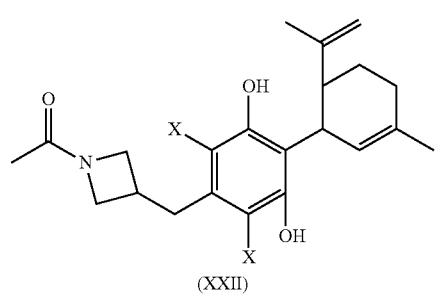

(XXII)

reacting the compound of formula (XXII) with a reducing agent to form the compound of formula (XX)

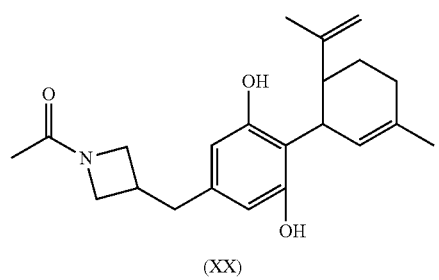

(XX)

15. The process of claim 12 wherein the compound of formula (VI) is selected from the group consisting of cannabidiol, cannabidivarin or

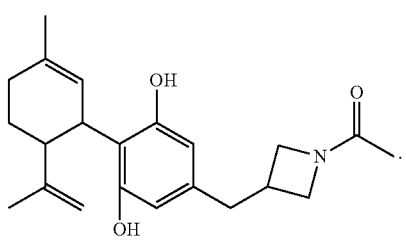

(XX)

16. The process of claim 12 wherein the protic or first Lewis acid catalyst is selected from the group consisting of p-toluene sulfonic acid, trifluoromethanesulfonic acid, trifluoroacetic acid, acetic acid, sulfuric acid, iron(II) chloride, scandium(III) triflate, zinc chloride, aluminum chloride and combinations thereof.

17. The process of claim 12 wherein the reducing agent is a sulfur-containing compound.

18. The process of claim 12 wherein the reduction occurs in a polar solvent.

19. The process of claim 12 wherein the reduction occurs in the presence of an organic or weak inorganic base.

20. The process of claim 12, further comprising
cyclizine the compound of formula (VI) by reacting the compound of formula (VI) with a second Lewis acid catalyst to form the compound of formula (I)

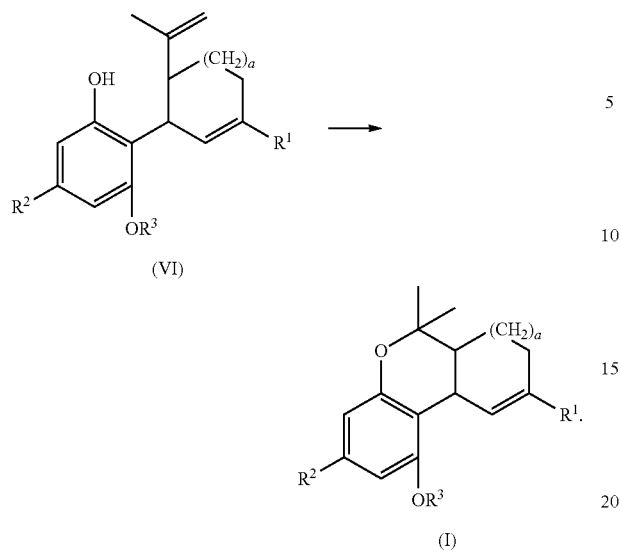
21. The process of claim 20 wherein the second Lewis acid catalyst is selected from the group consisting of p-toluene sulfonic acid, $BF_3$, diethyl etherate, $BF_3*AcOH$, tri-isobutyl aluminum, and combinations thereof.
* * * * *

UNITED STATES PATENT AND TRADEMARK OFFICE
CERTIFICATE OF CORRECTION

PATENT NO.         : 10,059,683 B2
APPLICATION NO.    : 15/199528
DATED              : August 28, 2018
INVENTOR(S)        : Dialer et al.

It is certified that error appears in the above-identified patent and that said Letters Patent is hereby corrected as shown below:

In the Claims

Column 74, Claim 20, Line 65:
Delete "cyclizine" and insert --cyclizing--

Signed and Sealed this
Eleventh Day of December, 2018

Andrei Iancu
*Director of the United States Patent and Trademark Office*